United States Patent
Kaur et al.

(10) Patent No.: US 8,679,767 B2
(45) Date of Patent: Mar. 25, 2014

(54) MULTIPLE REACTION MONITORING LC-MS/MS METHOD TO DETECT THERAPEUTIC ANTIBODIES IN ANIMAL SAMPLES USING FRAMEWORK SIGNATURE PEPTIDES

(75) Inventors: Surinder Kaur, Lafayette, CA (US); Ola Saad, Walnut Creek, CA (US); Keyang Xu, Belmont, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 13/469,332

(22) Filed: May 11, 2012

(65) Prior Publication Data

US 2012/0315645 A1 Dec. 13, 2012

Related U.S. Application Data

(60) Provisional application No. 61/485,249, filed on May 12, 2011.

(51) Int. Cl.
*G01N 33/53* (2006.01)
(52) U.S. Cl.
USPC ........................................... 435/7.1; 436/518
(58) Field of Classification Search
None
See application file for complete search history.

(56) References Cited

U.S. PATENT DOCUMENTS

| | | | |
|---|---|---|---|
| 2009/0286258 A1 | 11/2009 | Kaur | |
| 2010/0015652 A1 | 1/2010 | Granda | |

FOREIGN PATENT DOCUMENTS

| | | |
|---|---|---|
| WO | 2005/101017 | 10/2005 |
| WO | 2010/002911 A2 | 1/2010 |
| WO | 2011/042027 A2 | 4/2011 |

OTHER PUBLICATIONS

Anderson et al., "Quantitative mass spectrometric multiple reaction monitoring assays for major plasma proteins" Mol Cell Proteomics 5(4):573-88 ( 2006).
Boushaba et al., "Kinetics of whole serum and prepurified IgG digestion by pepsin for F(ab')2 manufacture" Biotechnol Prog. 19(4):1176-82 ( 2003).
Carr et al., "Protein quantitation through targeted mass spectrometry: the way out of biomarker purgatory?" Clin Chem. 54(11):1749-52 ( 2008).
Dere et al., "PK assays for antibody-drug conjugates: case study with ado-trastuzumab emtansine" Bioanalysis 5(9):1025-40 ( 2013).
Hagman et al., "Absolute quantification of monoclonal antibodies in biofluids by liquid chromatography-tandem mass spectrometry" Anal Chem. 80(4):1290-6 ( 2008).
Heudi et al., "Towards absolute quantification of therapeutic monoclonal antibody in serum by LC-MS/MS using isotope-labeled antibody standard and protein cleavage isotope dilution mass spectrometry" Anal Chem. 80(11):4200-7 ( 2008).
Ji et al., "A universal strategy for development of a method for absolute quantification of therapeutic monclonal antibodies in biological matrices using differential dimethyl labeling coupled with ultra performance liquid chromatography-tandem mass spectrometry" Anal Chem. 81(22):9321-8 ( 2009).
Jones et al., "A protocol for 'enhanced pepsin digestion': a step by step method for obtaining pure antibody fragments in high yield from serum" J Immunol Methods 275(1-2):239-50 ( 2003).
Kaur et al., "Bioanalytical assay strategies for the development of antibody-drug conjugate biotherapeutics" Bioanalysis 5(2):201-26 ( 2013).
Kuhn et al., "Developing multiplexed assays for troponin I and interleukin-33 in plasma by peptide immunoaffinity enrichment and targeted mass spectrometry" Clin Chem. 55(6):1108-1117, year 2009.
Liu et al., "Quantitation of a recombinant monoclonal antibody in monkey serum by liquid chromatography-mass spectrometry" Anal Biochem. 414(1):147-53 ( 2011).
PCT ISR PCT/US2012/037455.
X Yu et al. 'immunoglobulin heavy chain [*Homo sapiens*]' Retrived from the Internet http://www.ncbi.nlm.nih.gov.protein/ABY48864. 2, year 2013.
Xu et al., "Characterization of intact antibody-drug conjugates from plasma/serum in vivo by affinity capture capillary liquid chromatography-mass spectrometry" Analytical Biochemistry 412:56-66 ( 2011).
Xu et al., "Characterization of the drug-to-antibody ratio distribution for antibody-drug conjugates in plasma/serum" Bioanalysis 5(9):1057-71 (2013).

*Primary Examiner* — Jacob Cheu
(74) *Attorney, Agent, or Firm* — Alex Andrus; Genentech, Inc.

(57) ABSTRACT

Methods are disclosed to detect, characterize, measure, and quantitate human and humanized antibodies, and their conjugates, present in pre-clinical animal biological samples, including plasma/serum and tissue samples.

12 Claims, 23 Drawing Sheets

| | | | |
|---|---|---|---|
| CynoHC 1a D3 1 | 1 | ----------------------------------ASTKGPSVFPLAPSSR | STSESTAALGCL | 28 |
| CynoHC 1b E5 1 | 1 | ----------------------------------ASTKGPSVFPLAPSSR | STSESTAALGCL | 28 |
| Cyno HC 2a | 1 | ----------------------------------ASTKGPSVFPLAPSSR | STSQSTAALGCL | 28 |
| CynoHC 2b E6 1 | 1 | ----------------------------------ASTKGPSVFPLAPSSR | STSQSTAALGCL | 28 |
| Cyno HC 3 | 1 | ----------------------------------ASTKGPSVFPLAPSSR | STSESTAALGCL | 28 |
| Hu2H7 HC | 101 | YYSNSYWYFDVWGQGTLVTVSSASTKGPSVFPLAPSSK | STSGGTAALGCL | 150 |
|  |  | (CDR) | *FSP1*      *FSP2* |  |
| CynoHC 1a D3 1 | 29 | VKDYFPEPVTVSWNSGSLTSGVHTFPAVLQSSGLYSLSSVVTVPSSSLGT | | 78 |
| CynoHC 1b E5 1 | 29 | VKDYFPEPVTVSWNSGSLTSGVHTFPAVLQSSGLYSLSSVVTVPSSSLGT | | 78 |
| Cyno HC 2a | 29 | VKDYFPEPVTVSWNSGALTSGVHTFPAVLQSSGLYSLSSVVTVPSSSLGT | | 78 |
| CynoHC 2b E6 1 | 29 | VKDYFPEPVTVSWNSGALTSGVHTFPAVLQSSGLYSLSSVVTVPSSSLGT | | 78 |
| Cyno HC 3 | 29 | VKDYFPEPVTVSWNSGALTSGVHTFPAVLQSSGLYSLSSVVTVPSSSLGT | | 78 |
| Hu2H7 HC | 151 | VKDYFPEPVTVSWNSGALTSGVHTFPAVLQSSGLYSLSSVVTVPSSSLGT | | 200 |
| | | *FSP2*    (UPPER HINGE) | | |
| CynoHC 1a D3 1 | 79 | QTYVCNVNHKPSNTKVDKRVEIKTCGGGSKPPTCPPCPAPELLGGPSVFL | | 128 |
| CynoHC 1b E5 1 | 79 | QTYVCNVNHKPSNTKVDKRVEIKTCGGGSKPPTCPPCPAPELLGGPSVFL | | 128 |
| Cyno HC 2a | 79 | QTYVCNVVHEPSNTKVDKTVGLPCR------STCCPCAPELLGGPSVFL | | 121 |
| CynoHC 2b E6 1 | 79 | QTYVCNVVHEPSNTKVDKTVGLPCR------STCCPCAPELLGGPSVFL | | 121 |
| Cyno HC 3 | 79 | QTYVCNVVHEPSNTKVDKRVEFTPP------CPPCPAPELLGGPSVFL | | 120 |
| Hu2H7 HC | 201 | QTYICNVNHKPSNTKVDKKVEFKTCDKT---HTCPPCPAPELLGGPSVFL | | 247 |
| | | *FSP3* | | |
| CynoHC 1a D3 1 | 129 | FPPKPKDTLMISRTPEVTCVVVDVSQEDPDVK | FNWYVNGAEVHHAQTKPR | 178 |
| CynoHC 1b E5 1 | 129 | FPPKPKDTLMISRTPEVTCVVVDVSQEEPDVK | FNWYVNGAEVHHAQTKPR | 178 |
| Cyno HC 2a | 122 | FPPKPKDTLMISRTPEVTCVVVDVSQEDPDVK | FNWYVDGVEVHNAQTKPR | 171 |
| CynoHC 2b E6 1 | 122 | FPPKPKDTLMISRTPEVTCVVVDVSQEEPDVK | FNWYVNGAEVHHAQTKPR | 171 |
| Cyno HC 3 | 121 | FPPKPKDTLMISRTPEVTCVVVDVSQEDPDVK | FNWYVDGVEVHNAQTKPR | 170 |
| Hu2H7 HC | 248 | FPPKPKDTLMISRTPEVTCVVVDVSHEDPEVK | FNWYVDGVEVHNAKTKPR | 297 |
| | | | *FSP4* | |

Figure 1

| | | | |
|---|---|---|---|
| CynoHC 1a D3 1 | 179 | ETQYNSTYRVVSVLTVTHQDWLNGKEYTCKVSNKALPAPRQKTVSKTKGQ | 228 |
| CynoHC 1b E5 1 | 179 | EEQFNSTYRVVSVLTVTHQDWLNGKEYTCKVSNKALPAPRQKTVSKTKGQ | 228 |
| Cyno HC 2a | 172 | ETQYNSTYRVVSVLTVTHQDWLNGKEYTCKVSNKALPAPIQKTVSKDKGQ | 221 |
| CynoHC 2b E6 1 | 172 | EEQFNSTYRVVSVLTVTHQDWLNGKEYTCKVSNKALPAPIQKTVSKDKGQ | 221 |
| CynoHC 3 | 171 | EEQFNSTYRVVSVLTVTHQDWLNGKEYTCKVSNKALPAPRQKTVSKTKGQ | 220 |
| Hu2H7 HC | 298 | EEQYNSTYRVVSVLTVLHQDWLNGKEYKCKVSNKALPAPIEKTVSKAKGQ | 347 |

*FSP5*            *FSP6*

| | | | |
|---|---|---|---|
| CynoHC 1a D3 1 | 229 | PREPQVYTLPPPREELTKNQVSLTCLIKGFYPSDIVVEWASNGQPENTYK | 278 |
| CynoHC 1b E5 1 | 229 | PREPQVYTLPPPREELTKNQVSLTCLIKGFYPSDIVVEWASNGQPENTYK | 278 |
| Cyno HC 2a | 222 | PREPQVYTLPPSREELTKNQVSLTCLIKGFYPSDIVVEWESSGQPENTYK | 271 |
| CynoHC 2b E6 1 | 222 | PREPQVYTLPPSREELTKNQVSLTCLIKGFYPSDIVVEWESSGQPENTYK | 271 |
| CynoHC 3 | 221 | PREPQVYTLPPPREELTKNQVSLTCLIKGFYPSDIVVEWASNGQPENTYK | 270 |
| Hu2H7 HC | 348 | PREPQVYTLPPSREEMTKNQVSLTCLIKGFYPSDIAVEWESNGQPENNYK | 397 |

*FSP7*

| | | | |
|---|---|---|---|
| CynoHC 1a D3 1 | 279 | TTPPVLDSDGSYFLYSKLTVDKSRWQQGNVFSCSVMHEALHNHYTQKSLS | 328 |
| CynoHC 1b E5 1 | 279 | TTPPVLDSDGSYFLYSKLTVDKSRWQQGNVFSCSVMHEALHNHYTQKSLS | 328 |
| Cyno HC 2a | 272 | TTPPVLDSDGSYFLYSKLTVDKSRWQQGNVFSCSVMHEALHNHYTQKSLS | 321 |
| CynoHC 2b E6 1 | 272 | TTPPVLDSDGSYFLYSKLTVDKSRWQQGNVFSCSVMHEALHNHYTQKSLS | 321 |
| CynoHC 3 | 271 | TTPPVLDSDGSYFLYSKLTVDKSRWQQGNTFSCSVMHEALHNHYTQKSLS | 320 |
| Hu2H7 HC | 398 | TTPPVLDSDGSFFLYSKLTVDKSRWQQGNVFSCSVMHEALHNHYTQKSLS | 447 |

*FSP8*

Figure 1 (cont.)

rhuMAbHER2, recombinant, humanized trastuzumab
Heavy Chain

EVQLVESGGGLVQPGGSLRLSCAASGFNIKDTYIHWVRQAPGKGLEWVARIYPTNGYTRYADSV

/
KGRFTISADTSKNTAYLQMNSLRAEDTAVYYCSRWGGDGFYAMDYWGQGTLVTVSSASTK<u>GPS</u>

FSP1   /    FSP2     /
<u>VFPLAPSSKSTSGGTAALGCLVK</u>DYFPEPVTVSWNSGALTSGVHTFPAVLQSSGLYSLSSVVTVPSS

/
SLGTQTYICNVNHKPSNTKVDKKVEPKSCDKTHTCPPCPAPELLGGPSVFLFPPKPKDTLMISR<u>TPE</u>

FSP3     /       FSP4   /            /     FSP5     /
<u>VTCVVVDVSHEDPEVKFNWYVDGVEVHNAKTKPREEQYNSTYRVVSVLTVLHQDWLNGKEYK</u>

/  FSP6  /                                                               /    FSP7
CKVSNK<u>ALPAPIEKTISKAKGQPREPQVYTLPPSREEMTKNQVSLTCLVK</u><u>GFYPSDIAVEWESNGQ</u>

/     FSP8     /
<u>PENNYKTTPPVLDSDGSFFLYSK</u>LTVDKSRWQQGNVFSCSVMHEALHNHYTQKSLSLSPGK

Light Chain

DIQMTQSPSSLSASVGDRVTITCRASQDVNTAVAWYQQKPGKAPKLLIYSASFLYSGVPSRFSGSR

SGTDFTLTISSLQPEDFATYYCQQHYTTPPTFGQGTKVEIKRTVAAPSVFIFPPSDEQLKSGTASVVC

LLNNFYPREAKVQWKVDNALQSGNSQESVTEQDSKDSTYSLSSTLTLSKADYEKHKVYACEVTH

QGLSSPVTKSFNRGEC

Figure 2 rhuMAb 2H7, 2H7, ocrelizumab
Heavy Chain

EVQLVESGGGLVQPGGSLRLSCAASGYTFTSYNMHWVRQAPGKGLEWVGAIYPGNGDTSYNQK

/
FKGRFTISVDKSKNTLYLQMNSLRAEDTAVYYCARVVYYSNSYWYFDVWGQGTLVTVSSASTKG

FSP1   /    FSP2      /
PSVFPLAPSSKSTSGGTAALGCLVKDYFPEPVTVSWNSGALTSGVHTFPAVLQSSGLYSLSSVVTVP

/
SSSLGTQTYICNVNHKPSNTKVDKKVEPKSCDKTHTCPPCPAPELLGGPSVFLFPPKPKDTLMISRT

FSP3    /    FSP4    /        /   FSP5........./
PEVTCVVVDVSHEDPEVKFNWYVDGVEVHNAKTKPREEQYNSTYRVVSVLTVLHQDWLNGKEY

/ FSP6 /                                  /  FSP7....
KCKVSNKALPAPIEKTISKAKGQPREPQVYTLPPSREEMTKNQVSLTCLVKGFYPSDIAVEWESNG

/    FSP8    /
QPENNYKTTPPVLDSDGSFFLYSKLTVDKSRWQQGNVFSCSVMHEALHNHYTQKSLSLSPGK

Light Chain

DIQMTQSPSSLSASVGDRVTITCRASSSVSYMHWYQQKPGKAPKPLIYAPSNLASGVPSRFSGSGS

GTDFTLTISSLQPEDFATYYCQQWSFNPPTFGQGTKVEIKRTVAAPSVFIFPPSDEQLKSGTASVVCL

LNNFYPREAKVQWKVDNALQSGNSQESVTEQDSKDSTYSLSSTLTLSKADYEKHKVYACEVTHQ

GLSSPVTKSFNRGEC

Figure 3

Pertuzumab, rhuMAb 2C4, 2C4

Heavy Chain

EVQLVESGGGLVQPGGSLRLSCAASGFTFTDYTMDWVRQAPGKGLEWVADVNPNSGGSIYNQRFKG
RFTLSVDRSKNTLYLQMNSLRAEDTAVYYCARNLGPSFYFDYWGQGTLVTVSSASTKGPSVFPLAP
SSKSTSGGTAALGCLVKDYFPEPVTVSWNSGALTSGVHTFPAVLQSSGLYSLSSVVTVPSSSLGTQ
TYICNVNHKPSNTKVDKKVEPKSCDKTHTCPPCPAPELLGGPSVFLFPPKPKDTLMISRTPEVTCV
VVDVSHEDPEVKFNWYVDGVEVHNAKTKPREEQYNSTYRVVSVLTVLHQDWLNGKEYKCKVSNKAL
PAPIEKTISKAKGQPREPQVYTLPPSREEMTKNQVSLTCLVKGFYPSDIAVEWESNGQPENNYKTT
PPVLDSDGSFFLYSKLTVDKSRWQQGNVFSCSVMHEALHNHYTQKSLSLSPG (SEQ ID NO:20)

Light Chain

DIQMTQSPSSLSASVGDRVTITCKASQDVSIGVAWYQQKPGKAPKLLIYSASYRYTGVPSRFSGSG
SGTDFTLTISSLQPEDFATYYCQQYYIYPYTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC (SEQ ID NO:21)

Figure 4

Anti-PDL1

Heavy Chain

EVQLVESGGGLVQPGGSLRLSCAASGFTFSDSWIHWVRQAPGKGLEWVAWISPYGGSTYYADSVKG
RFTISADTSKNTAYLQMNSLRAEDTAVYYCARRHWPGGFDYWGQGTLVTVSSASTKGPSVFPLAPS
SKSTSGGTAALGCLVKDYFPEPVTVSWNSGALTSGVHTFPAVLQSSGLYSLSSVVTVPSSSLGTQT
YICNVNHKPSNTKVDKKVEPKSCDKTHTCPPCPAPELLGGPSVFLFPPKPKDTLMISRTPEVTCVV
VDVSHEDPEVKFNWYVDGVEVHNAKTKPREEQYASTYRVVSVLTVLHQDWLNGKEYKCKVSNKALP
APIEKTISKAKGQPREPQVYTLPPSREEMTKNQVSLTCLVKGFYPSDIAVEWESNGQPENNYKTTP
PVLDSDGSFFLYSKLTVDKSRWQQGNVFSCSVMHEALHNHYTQKSLSLSPGK (SEQ ID NO:22)

Light Chain

DIQMTQSPSSLSASVGDRVTITCRASQDVSTAVAWYQQKPGKAPKLLIYSASFLYSGVPSRFSGSG
SGTDFTLTISSLQPEDFATYYCQQYLYHPATFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC (SEQ ID NO:23)

Figure 5

Anti_Neuropilin-a (anti-NRP1, MNRP1685A

Heavy Chain

EVQLVESGGGLVQPGGSLRLSCAASGFTFSSYAMSWVRQAPGKGLEWVSQISPAGGYTNYADSVKG
RFTISADTSKNTAYLQMNSLRAEDTAVYYCARGELPYYRMSKVMDVWGQGTLVTVSSASTKGPSVF
PLAPSSKSTSGGTAALGCLVKDYFPEPVTVSWNSGALTSGVHTFPAVLQSSGLYSLSSVVTVPSSS
LGTQTYICNVNHKPSNTKVDKKVEPKSCDKTHTCPPCPAPELLGGPSVFLFPPKPKDTLMISRTPE
VTCVVVDVSHEDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPGK (SEQ ID NO:24)

Light Chain

DIQMTQSPSSLSASVGDRVTITCRASQYFSSYLAWYQQKPGKAPKLLIYGASSRASGVPSRFSGSG
SGTDFTLTISSLQPEDFATYYCQQYLGSPPTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC (SEQ ID NO:25)

Figure 6

3A5 anti-MUC16

Heavy Chain

EVQLVESGGGLVQPGGSLRLSCAASGYSITNDYAWNWVRQAPGKGLEWVGYISYSGYTTYNPSLKS
RFTISRDTSKNTLYLQMNSLRAEDTAVYYCARWTSGLDYWGQGTLVTVSSCSTKGPSVFPLAPSSK
STSGGTAALGCLVKDYFPEPVTVSWNSGALTSGVHTFPAVLQSSGLYSLSSVVTVPSSSLGTQTYI
CNVNHKPSNTKVDKKVEPKSCDKTHTCPPCPAPELLGGPSVFLFPPKPKDTLMISRTPEVTCVVVD
VSHEDPEVKFNWYVDGVEVHNAKTKPREEQYNSTYRVVSVLTVLHQDWLNGKEYKCKVSNKALPAP
IEKTISKAKGQPREPQVYTLPPSREEMTKNQVSLTCLVKGFYPSDIAVEWESNGQPENNYKTTPPV
LDSDGSFFLYSKLTVDKSRWQQGNVFSCSVMHEALHNHYTQKSLSLSPGK (SEQ ID NO:26)

Light Chain

DIQMTQSPSSLSASVGDRVTITCKASDLIHNWLAWYQQKPGKAPKLLIYGATSLETGVPSRFSGSG
SGTDFTLTISSLQPEDFATYYCQQYWTTPFTFGQGTKVEIKRTVAAPSVFIFPPSDEQLKSGTASV
VCLLNNFYPREAKVQWKVDNALQSGNSQESVTEQDSKDSTYSLSSTLTLSKADYEKHKVYACEVTH
QGLSSPVTKSFNRGEC (SEQ ID NO:27)

Figure 7

C2B8, anti-CD20, rituximab

Heavy Chain

```
QVQLQQPGAELVKPGASVKMSCKASGYTFTSYNMHWVKQTPGRGLEWIGAIYPGNGDTSYNQKFKG
KATLTADKSSSTAYMQLSSLTSEDSAVYYCARSTYYGGDWYFNVWGAGTTVTVSAASTKGPSVFPL
APSSKSTSGGTAALGCLVKDYFPEPVTVSWNSGALTSGVHTFPAVLQSSGLYSLSSVVTVPSSSLG
TQTYICNVNHKPSNTKVDKKAEPKSCDKTHTCPPCPAPELLGGPSVFLFPPKPKDTLMISRTPEVT
CVVVDVSHEDPEVKFNWYVDGVEVHNAKTKPREEQYNSTYRVVSVLTVLHQDWLNGKEYKCKVSNK
ALPAPIEKTISKAKGQPREPQVYTLPPSRDELTKNQVSLTCLVKGFYPSDIAVEWESNGQPENNYK
TTPPVLDSDGSFFLYSKLTVDKSRWQQGNVFSCSVMHEALHNHYTQKSLSLSPGK (SEQ ID NO:28)
```

Light Chain

```
QIVLSQSPAILSASPGEKVTMTCRASSSVSYIHWFQQKPGSSPKPWIYATSNLASGVPVRFSGSGS
GTSYSLTISRVEAEDAATYYCQQWTSNPPTFGGGTKLEIKRTVAAPSVFIFPPSDEQLKSGTASVV
CLLNNFYPREAKVQWKVDNALQSGNSQESVTEQDSKDSTYSLSSTLTLSKADYEKHKVYACEVTHQ
GLSSPVTKSFNRGEC (SEQ ID NO:29)
```

Figure 8

Figure 13. Trastuzumab in cynomolgus monkey plasma

Generic Capture
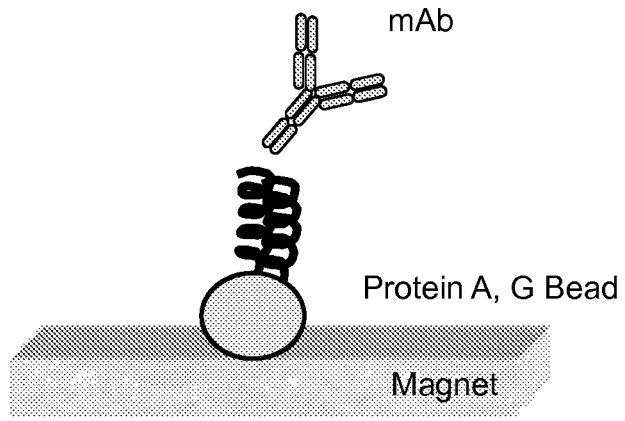
Specific Capture
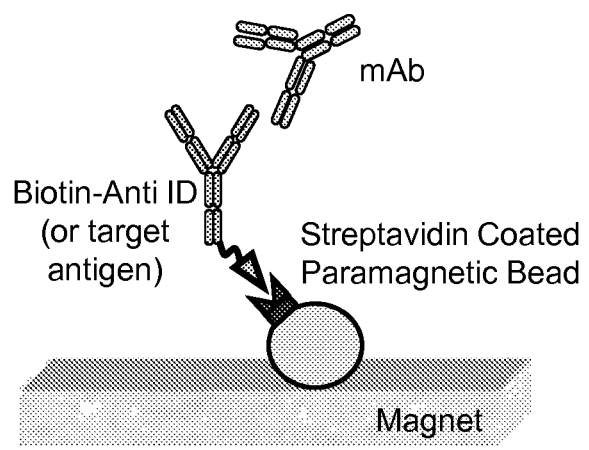
Figure 16

ELISA

Protein A bead capture / Trypsin digestion

Framework signature peptide (FSP8):
TTPPVLDSDGSFFLYSK

MRM transition:
938.0 (M, 2+) ⟶ 836.7 (y15, 2+)

LC-MS/MS

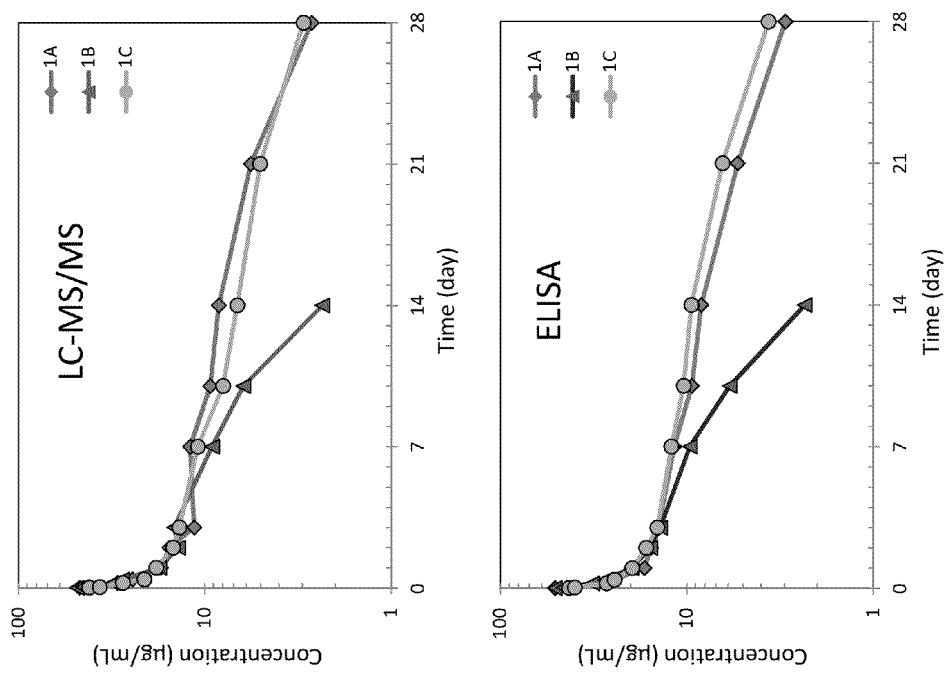
Figure 20. Anti-HER2 (trastuzumab)

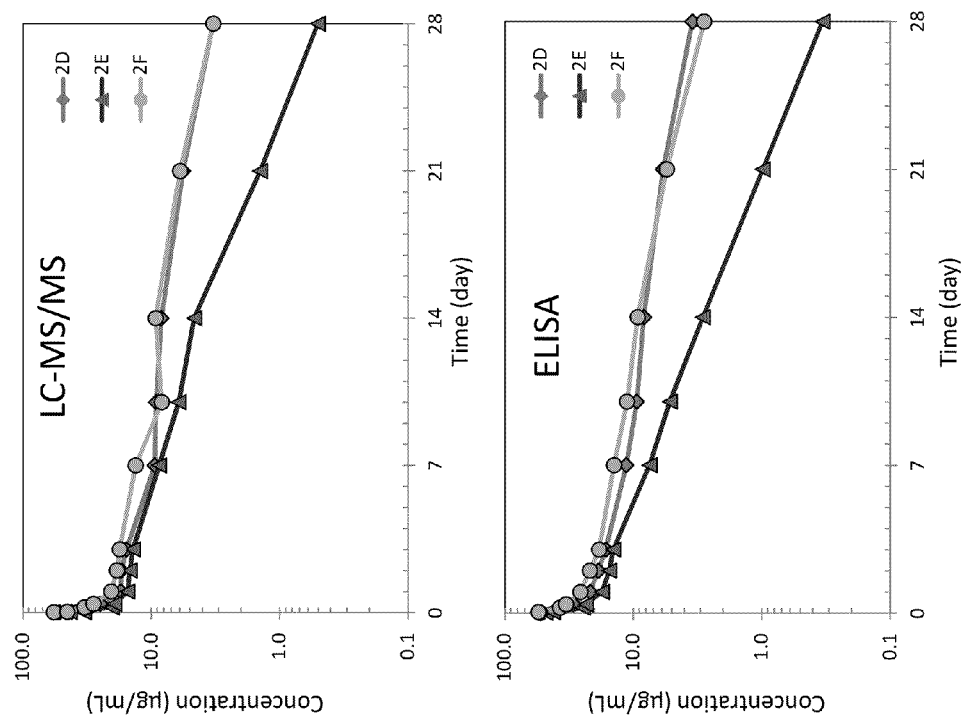
Figure 21. Anti-MUC16

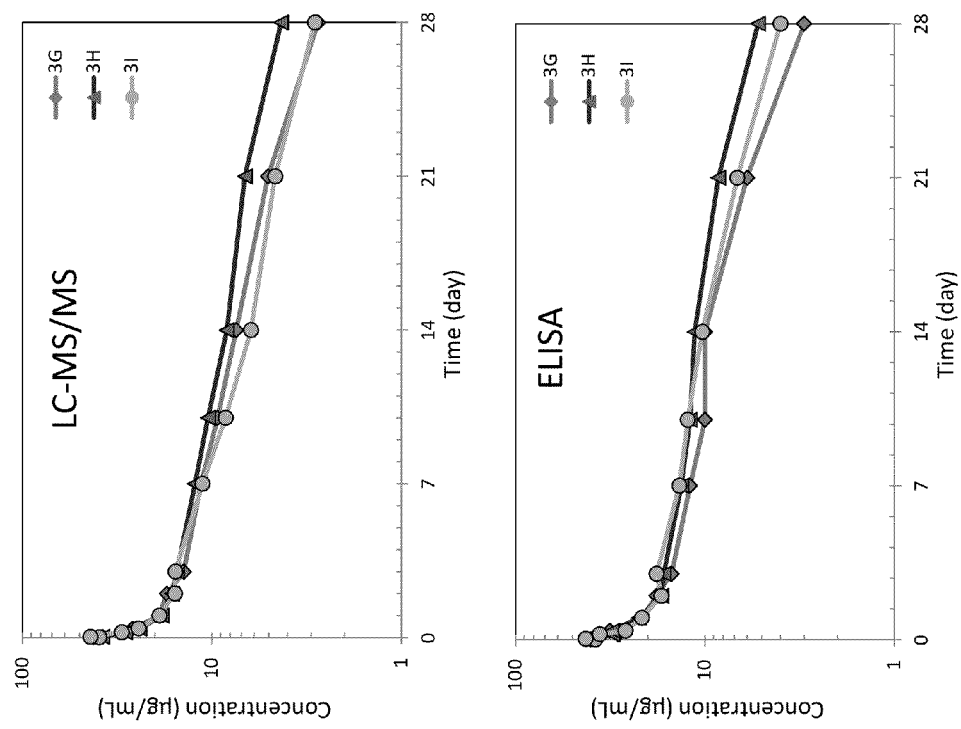
Figure 22. Anti-Mesothelin

MULTIPLE REACTION MONITORING LC-MS/MS METHOD TO DETECT THERAPEUTIC ANTIBODIES IN ANIMAL SAMPLES USING FRAMEWORK SIGNATURE PEPTIDES

CROSS REFERENCE TO RELATED APPLICATIONS

This non-provisional application filed under 37 CFR §1.53(b), claims the benefit under 35 USC §119(e) of U.S. Provisional Application Ser. No. 61/485,249 filed on 12 Mar. 2011, which is incorporated by reference in entirety.

FIELD OF THE INVENTION

The present invention relates to methods of detecting and determining the amount of a human or humanized antibody of interest from an animal sample such as tissue, plasma or serum. The methods include affinity enrichment and protease digestion of the sample to produce one or more peptides unique and conserved to the framework region of a human or humanized antibody detected and quantified by mass spectrometry.

BACKGROUND

The analysis of plasma/serum samples generated from in vivo studies of therapeutic proteins is of interest in the biopharmaceutical industry. The conventional ELISA approach has been used for over 25 years and has several limitations. The ELISA require high quality custom reagents that can take several months to generate and the assay optimization can take an additional number of months. Thus, ELISA has a long assay development time which is a limitation in both the early discovery stage and the development stage of protein-based drugs (Murray et al (2001) J. Imm. Methods 255:41-56; Kirchner et al (2004) Clin. Pharmacokinetics 43(2):83-95). Suitable ELISA reagents and assay conditions may not be possible in some cases due to the highly custom binding requirements for each protein therapeutic. Another limitation of ELISA is that reagents may bind non-specifically with plasma/serum proteins; matrix interference is a common phenomenon. Protein quantification by mass spectrometry on the other hand is highly specific and therefore matrix interference is rare compared to ELISA. Development of ELISA assays can be labor-intensive and require complex, specific reagents. ELISA is also sensitive to matrix interferences and cross-reactivity of antibodies. ELISA measures analyte concentration indirectly using binding properties. These many variables make ELISA methods of protein quantification challenging to develop and transfer to other laboratories with robust performance. On the basis of these differences, mass spectrometry is an orthogonal method to ELISA. Mass spectrometry methods of protein quantification, LC-MS/MS in particular, do not require custom reagents and generally yields faster assay development. In addition, Mass spectrometry is less subject to matrix interferences and provides generic assay conditions which are highly specific and can be multiplexed and automated. The high specificity of mass spectrometry measures analyte concentration using intrinsic physical chemical properties of the analyte, i.e. mass and fragmentation pattern. The robust format allows ready lab-to-lab transfer, a significant advantage for approved antibody therapies. A general methodology for quantifying proteins by mass spectrometry is trypsin digestion of the intact protein. The resulting peptides are analyzed by mass spectrometry by introducing corresponding stable isotope labeled internal standards at a fixed concentration.

Recent advances in peptide and protein analysis by mass spectrometry (MS) are due to the developments in front-end gas phase ionization and introduction techniques such as electrospray ionization (ESI), and matrix-assisted laser desorption ionization (MALDI, US 2003/0027216), as well as improvements in instrument sensitivity, resolution, mass accuracy, bioinformatics, and software data deconvolution algorithms ("Electrospray Ionization Mass Spectrometry: Fundamentals, Instrumentation, and Applications", Cole, R. B., Ed. (1997) Wiley, New York; "Modern Protein Chemistry: Practical Aspects", Howard, G. C. and Brown, W. E., Eds. (2002) CRC Press, Boca Raton, Fla., p. 71-102; Martin et al (1997) Cancer Chemother. Pharmacol. 40:189-201; WO 03/046571; WO 03/046572).

Liquid chromatography-tandem mass spectrometry is a powerful tool for protein analysis and quantitation in very complex matrices like plasma/serum samples. Since peptides resulting from the digestion of the protein of interest and other plasma/serum proteins may have the same or similar nominal mass, the second dimension of MS fragmentation often provides a unique fragment of a peptide of interest. The combination of the specific parent peptide and the unique fragment ion is used to selectively monitor for the molecule to be quantified. Such approach is termed "Multiple reaction monitoring" (MRM), also referred to as Selected Reaction Monitoring (SRM), which is a commonly used mode for protein quantitation.

Electrospray ionization (ESI) provides for the atmospheric pressure ionization (API) of a liquid sample. The electrospray process creates highly-charged droplets that, under evaporation, create ions representative of the species contained in the solution. An ion-sampling orifice of a mass spectrometer may be used to sample these gas phase ions for mass analysis. The response for an analyte measured by the mass spectrometer detector is dependent on the concentration of the analyte in the fluid and independent of the fluid flow rate.

SUMMARY

The invention provides a method of detecting human or humanized antibodies comprising the steps of:

(a) treating a biological sample with a digestive enzyme to form a digested antibody sample, wherein the biological sample is serum, plasma, tissue, or cells from an animal that has been treated with a human or humanized antibody; and (b) analyzing the digested antibody sample by mass spectrometry to detect one or more human framework peptides.

In an exemplary embodiment, human framework peptides comprise one or more sequences selected from SEQ ID NOS. 1-8.

In an exemplary embodiment, the digestive enzyme is trypsin.

In an exemplary embodiment, the biological sample is contacted with an affinity capture media or chromatography adsorbent. An enriched biological sample is eluted then treated with the digestive enzyme.

In an exemplary embodiment, the concentration of digested antibody sample is measured.

An aspect of the invention are methods of protease digestion of the sample or immunoaffinity capture followed by protease digestion to produce one or more peptides unique to the framework region of a human or humanized antibody, i.e., not present in animal biological samples, detected and quantified by mass spectrometry (LC-MS/MS).

An embodiment of the invention is human or humanized antibodies conjugated to drug moieties where antibody-drug conjugates are measured by the methods of the invention.

BRIEF DESCRIPTION OF THE FIGURES

FIG. 1 shows the alignment of heavy chain amino acid sequences of a human 2H7 antibody ocrelizumab, Hu2H7 (SEQ ID NO:11) starting at residue 101, and five cynomolgus monkey anti-CD20 antibodies: CynoHC 1a D3 1 (SEQ ID NO:12), CynoHC 1b E5 1 (SEQ ID NO:13), Cyno HC 2a (SEQ ID NO:14), CynoHC 2b E6 1 (SEQ ID NO:15), CynoHC 3 (SEQ ID NO:16). Framework signature peptides are identified (FSP 1-8) as underlined which are unique to human 2H7 (hu 2H7) Mab and are not present in cynomolgus monkey IgG heavy chain, each bearing at least one amino acid difference in the sequences.

FIG. 2 shows the heavy chain (SEQ ID NO:17) and light chain (SEQ ID NO:18) of trastuzumab (Herceptin®, Genentech Inc.; rhuMAbHER2, Anti p185HER2), a recombinant derived humanized monoclonal antibody, CAS Registry No. 180288-69-1.

FIG. 3 shows the heavy chain (SEQ ID NO:11) and light chain (SEQ ID NO:19) of ocrelizumab, rhuMAb 2H7, PRO70769, a humanized anti-CD20 antibody, CAS Registry No. 637334-45-3.

FIG. 4 shows the heavy chain (SEQ ID NO:20) and light chain (SEQ ID NO:21) of pertuzumab, rhuMAb 2C4, CAS Registry No. 380610-27-5. FSP2, FSP3, FSP8 are identified as underlined in heavy chain (SEQ ID NO:20).

FIG. 5 shows the heavy chain (SEQ ID NO:22) and light chain (SEQ ID NO:23) of anti-PDL1, member of the extended CD28/CTLA-4 family of T cell regulators. FSP2, FSP4, FSP8 are identified as underlined in heavy chain (SEQ ID NO:22).

FIG. 6 shows the heavy chain (SEQ ID NO:24) and light chain (SEQ ID NO:25) of anti-neuropilin-1, anti-NRP1, MNRP1685A. FSP2, FSP4, FSP8 are identified as underlined in heavy chain (SEQ ID NO:24).

FIG. 7 shows the heavy chain (SEQ ID NO:26) and light chain (SEQ ID NO:27) of anti-MUC16, MMUC3333A/DMUC4064A. FSP2, FSP4, FSP8 are identified as underlined in heavy chain (SEQ ID NO:26).

FIG. 8 shows the (SEQ ID NO:28) and light chain (SEQ ID NO:29) of rituximab, C2B8, MabThera, (Rituxan®, Genentech Inc., Biogen/Idec), CAS Registry No. 174722-31-7. FSP2, FSP4, FSP8 are identified as underlined in heavy chain (SEQ ID NO:28).

FIG. 16 shows embodiments of Protein A, G coated magnetic bead (top) for generic capture of antibody and streptavidin coated magnetic beads bound to a biotinylated capture probe (bottom) for specific capture of antibody.

FIG. 20 shows the concordance between the LC-MS/MS assay shown in FIG. 19b and the ELISA assay of FIG. 19a based on individual pharmacokinetics (PK) of plasma/serum samples from rats dosed with trastuzumab, an anti-HER2 mAb.

FIG. 21 shows the concordance between the LC-MS/MS assay shown in FIG. 19b and the ELISA assay of FIG. 19a based on individual pharmacokinetics (PK) of plasma/serum samples from rats dosed with 3A5, an anti-MUC 16 mAb.

FIG. 22 shows the concordance between the LC-MS/MS assay shown in FIG. 19b and the ELISA assay of FIG. 19a based on individual pharmacokinetics (PK) of plasma/serum samples from rats dosed with an anti-mesothelin (Msln) mAb.

DETAILED DESCRIPTION OF EMBODIMENTS OF THE INVENTION

Figure 9:
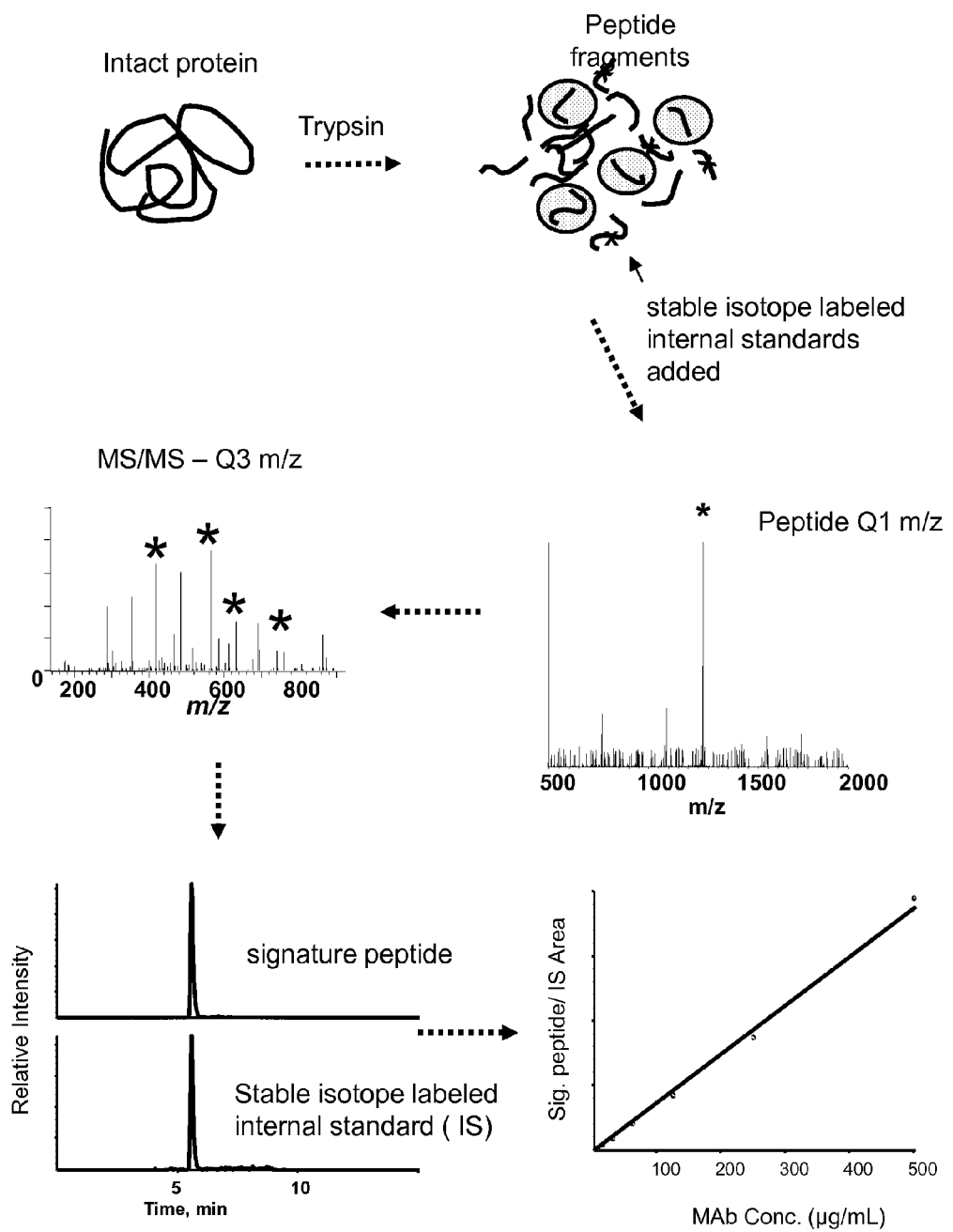
FIG. 9 shows the generic steps for LC-MS/MS method to quantify a therapeutic antibody in animal plasma/serum using one or more framework signature peptides (FSP).

Unless defined otherwise, technical and scientific terms used herein have the same meaning as commonly understood by one of ordinary skill in the art to which this invention belongs, and are consistent with: Singleton et al, (1994) "Dictionary of Microbiology and Molecular Biology", 2nd Ed., J. Wiley & Sons, New York, N.Y.; and Janeway, et al (2001) "Immunobiology", 5th Ed., Garland Publishing, New York. When trade names are used herein, the trade name product formulation, the generic drug, and the active pharmaceutical ingredient(s) of the trade name product are also included.

DEFINITIONS

The term "biological sample" is any component derived or separated from an animal and includes blood, plasma, serum, cells, urine, cerebrospinal fluid (CSF), milk, bronchial lavage, bone marrow, amniotic fluid, saliva, bile, vitreous, tears, or tissue.

The term "digestive enzyme" is an enzyme capable of cleaving or hydrolyzing peptides or proteins into fragments in either a specific or generic, random manner. A digestive enzyme can form a digested antibody sample from an antibody where the antibody is a component of a biological sample. Digestive enzymes include proteases such as trypsin, papain, endoproteinase LysC, endoproteinase ArgC, *staph aureus* V8, chymotrypsin, Asp-N, Asn-C, pepsin, and endoproteinase GluC.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Pluckthün, in *The Pharmacology of Monoclonal Antibodies*, vol. 113, Rosenburg and Moore eds., (Springer-Verlag, New York), pp. 269-315 (1994); WO 93/16185; U.S. Pat. No. 5,571,894; U.S. Pat. No. 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific (EP 404097; WO 1993/01161; Hudson et al. (2003) *Nat. Med.* 9:129-134; Hollinger et al. (1993) *Proc. Natl. Acad. Sci. USA* 90: 6444-6448). Triabodies and tetrabodies are also described in Hudson et al. (2003) *Nat. Med.* 9:129-134.

Single-domain antibodies are antibody fragments comprising all or a portion of the heavy chain variable domain or all or a portion of the light chain variable domain of an antibody. In certain embodiments, a single-domain antibody is a human single-domain antibody (U.S. Pat. No. 6,248,516).

Antibody fragments can be made by various techniques, including but not limited to proteolytic digestion of an intact antibody as well as production by recombinant host cells (e.g. *E. coli* or phage), as described herein.

The term "chimeric" antibody refers to an antibody in which a portion of the heavy and/or light chain is derived from a particular source or species, while the remainder of the heavy and/or light chain is derived from a different source or species.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to constant domain residues other than hypervariable region (HVR) residues. The FR of a constant domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework region of an antibody which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al. *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

A "chimeric" antibody comprises a non-human variable region (e.g., a variable region derived from a mouse, rat, hamster, rabbit, or non-human primate, such as a monkey) and a human constant region (U.S. Pat. No. 4,816,567; Morrison et al. (1984) *Proc. Natl. Acad. Sci. USA*, 81:6851-6855). In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. No. 5,821,337; U.S. Pat. No. 7,527,791; U.S. Pat. No. 6,982,321; U.S. Pat. No. 7,087,409; Kashmiri et al. (2005) Methods 36:25-34 (describing SDR (a-CDR) grafting); Padlan, (1991) Mol. Immunol. 28:489-498 (describing "resurfacing"); Dall'Acqua et al. (2005) Methods 36:43-60 (describing "FR shuffling"); and Osbourn et al, (2005) Methods 36:61-68; Klimka et al. (2000) Br. J. Cancer 83:252-260 (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (Carter et al. (1992) Proc. Natl. Acad. Sci. USA, 89:4285; Presta et al. (1993) J. Immunol., 151:2623); human mature (somatically mutated) framework regions or human germline framework regions (Almagro and Fransson, (2008) Front. Biosci. 13:1619-1633); and framework regions derived from screening FR libraries (see, e.g., Baca et al. (1997) J. Biol. Chem. 272:10678-10684; and Rosok et al. (1996) J. Biol. Chem. 271:22611-22618).

Human antibodies can be produced using various techniques known in the art. Human antibodies are described generally in van Dijk and van de Winkel, (2001) *Curr. Opin. Pharmacol.* 5: 368-74; Lonberg, *Curr. Opin. Immunol.* 20:450-459 (2008).

Human antibodies may be prepared by administering an immunogen to a transgenic animal that has been modified to produce intact human antibodies or intact antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, *Nat. Biotech.* 23:1117-1125 (2005). See also, e.g., U.S. Pat. Nos. 6,075,181 and 6,150,584 describing XENOMOUSE™ technology; U.S. Pat. No. 5,770,429 describing HuMAB® technology; U.S. Pat. No. 7,041,870 describing K-M MOUSE® technology, and US 2007/0061900, describing VELOCIMOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor *J. Immunol.*, 133: 3001 (1984); Brodeur et al., *Monoclonal Antibody Production Techniques and Applications*, pp. 51-63 (Marcel Dekker, Inc., New York, 1987); and Boerner et al., (1991) *J. Immunol.*, 147: 86) Human antibodies generated via human B-cell hybridoma technology are also described in Li et al., *Proc. Natl. Acad. Sci. USA*, 103:3557-3502 (2006). Additional methods include those described, for example, in U.S. Pat. No. 7,189,826 (describing production of monoclonal human IgM antibodies from hybridoma cell lines); Ni, (2006) *Xiandai Mianyixue*, 26(4):265-268 (describing human-human hybridomas). Human hybridoma technology (Trioma technology) is also described in Vollmers and Brandlein, (2005) *Histology and Histopathology*, 20(3):927-937 and Vollmers and Brandlein, (2005) *Methods and Findings in Experimental and Clinical Pharmacology*, 27(3):185-91.

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in *Methods in Molecular Biology* 178:1-37 (O'Brien et al., ed., Human Press, Totowa, N.J., 2001) and further described, e.g., in the McCafferty et al., *Nature* 348: 552-554; Clackson et al., *Nature* 352: 624-628 (1991); Marks et al. (1992) *J. Mol. Biol.* 222: 581-597; Marks and Bradbury, in *Methods in Molecular Biology* 248:161-175 (Lo, ed., Human Press, Totowa, N.J., 2003); Sidhu et al. (2004) *J. Mol. Biol.* 338(2): 299-310; Lee et al. (2004) *J. Mol. Biol.* 340(5): 1073-1093; Fellouse, (2004) *Proc. Natl. Acad. Sci. USA* 101 (34): 12467-12472; and Lee et al. (2004) *J. Immunol. Methods* 284(1-2): 119-132.

In certain phage display methods, repertoires of VH and VL genes are separately cloned by polymerase chain reaction (PCR) and recombined randomly in phage libraries, which can then be screened for antigen-binding phage as described in Winter et al., *Ann. Rev. Immunol.*, 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., *EMBO J,* 12:

725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, *J. Mol. Biol.*, 227: 381-388 (1992). Human antibody phage libraries are described in U.S. Pat. No. 5,750, 373; US 2005/0079574; US 2005/0119455; US 2005/0266000; US 2007/0117126; US 2007/0160598; US 2007/0237764; US 2007/0292936; US 2009/0002360. Antibodies or antibody fragments isolated from human antibody libraries are considered human antibodies or human antibody fragments herein.

In certain embodiments, an antibody is a multispecific antibody, e.g. a bispecific antibody. Multispecific antibodies are monoclonal antibodies that have binding specificities for at least two different sites. In certain embodiments, one of the binding specificities is for one antigen and the other is for a second antigen. In certain embodiments, bispecific antibodies may bind to two different epitopes of the same antigen. Bispecific antibodies may also be used to localize cytotoxic agents to cells which express an antigen. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, *Nature* 305: 537 (1983)), WO 93/08829, and Traunecker et al., *EMBO J.* 10: 3655 (1991)), and "knob-in-hole" engineering (U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., *Science*, 229: 81 (1985)); using leucine zippers to produce bi-specific antibodies (see, e.g., Kostelny et al., *J. Immunol.*, 148(5):1547-1553 (1992)); using "diabody" technology for making bispecific antibody fragments (see, e.g., Hollinger et al., *Proc. Natl. Acad. Sci. USA*, 90:6444-6448 (1993)); and using single-chain Fv (sFv) dimers (Gruber et al., *J. Immunol.*, 152:5368 (1994)); and preparing trispecific antibodies (Tutt et al. (1991) *J. Immunol.* 147: 60).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to an antigen as well as another, different antigen (see, US 2008/0069820, for example).

Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

Antibodies include fusion proteins comprising an antibody and a protein, drug moiety, label, or some other group. Fusion proteins may be made by recombinant techniques, conjugation, or peptide synthesis, to optimize properties such as pharmacokinetics. The human or humanized antibody of the invention may also be a fusion protein comprising an albumin-binding peptide (ABP) sequence (Dennis et al. (2002) "Albumin Binding As A General Strategy For Improving The Pharmacokinetics Of Proteins" *J Biol. Chem.* 277:35035-35043; WO 01/45746). Antibodies of the invention include fusion proteins with ABP sequences taught by: (i) Dennis et al (2002) *J Biol. Chem.* 277:35035-35043 at Tables III and IV, page 35038; (ii) US 2004/0001827 at [0076]; and (iii) WO 01/45746 at pages 12-13, and all of which are incorporated herein by reference.

Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "conservative substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or SDRs (a-CDRs), with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may be outside of HVR "hotspots" or SDRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region (Wright et al. (1997) *TIBTECH* 15:26-32). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function (US 2003/0157108; US 2004/0093621). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. (2004) *Biotech. Bioeng.* 87:614. Examples of cell lines capable of producing defucosylated antibodies include Lec13 CHO cells deficient in protein fucosylation (Ripka et al. *Arch. Biochem. Biophys.* 249:533-545 (1986); US 2003/0157108, Presta, L; and WO 2004/056312, Adams et al., especially at Example 11), and knockout cell lines, such as alpha-1,6-fucosyltransferase gene, FUT8, knockout CHO cells (Yamane-Ohnuki et al (2004) *Biotech. Bioeng.* 87:614; Kanda, Y. et al. (2006) *Biotechnol. Bioeng.*, 94(4):680-688; WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described (WO 1997/30087; WO 1998/58964; WO 1999/22764).

Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express FcγRIII only, whereas monocytes express FcγRI, FcγRII and FcγRIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362; Hellstrom, I. et al. (1986) *Proc. Nat'l Acad. Sci. USA* 83:7059-7063); Hellstrom, I et al. (1985) *Proc. Nat'l Acad. Sci. USA* 82:1499-1502; U.S. Pat. No. 5,821,337; Bruggemann, M. et al. (1987) *J. Exp. Med.* 166:1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. (1998) *Proc. Nat'l Acad. Sci. USA* 95:652-656. C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (Gazzano-Santoro et al. (1996), *J. Immunol. Methods* 202: 163; Cragg, M. S. et al. (2003) *Blood* 101:1045-1052; Cragg, M. S, and M. J. Glennie, (2004) *Blood* 103:2738-2743). FcRn binding and in vivo clearance/half life determinations can also be performed using methods known in the art (Petkova, S. B. et al. (2006) *Int'l. Immunol.* 18(12):1759-1769).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (U.S. Pat. No. 6,737,056; WO 2004/056312; Shields et al. (2001) *J. Biol. Chem.* 9(2): 6591-6604).

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. (2000) *J. Immunol.* 164: 4178-4184.

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan & Winter, *Nature* 322:738-40 (1988); U.S. Pat. No. 5,648,260; U.S. Pat. No. 5,624,821; and WO 94/29351 concerning other examples of Fc region variants.

Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an antibody-drug conjugate (ADC), also referred to as an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propylene glycol homopolymers, polypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al. (2005) *Proc. Natl. Acad. Sci. USA* 102:11600-11605). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

The term "hypervariable region" or "HVR," as used herein, refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3) (Chothia and Lesk, (1987) *J. Mol. Biol.* 196:901-917). Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3 (Kabat et al., *Sequences of Proteins of Immunological Interest,* 5th Ed. Public Health Service, National Institutes of Health, Bethesda, Md. (1991). With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3 (Almagro and Fransson, (2008) *Front. Biosci.* 13:1619-1633). Unless otherwise indicated, HVR residues and other residues in the variable domain (e.g., FR residues) are numbered herein according to Kabat et al., supra.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al. (2007) *J. Chromatogr. B* 848:79-87.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows: 100 times the fraction X/Y, where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). See for example, Kindt et al. Kuby Immunology, 6$^{th}$ ed., W.H. Freeman and Co., page 91 (2007). A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (Portolano et al. (1993) J. Immunol. 150:880-887; Clarkson et al. (1991) Nature 352:624-628).

"Tumor-associated antigens" (TAA) are known in the art, and can prepared for use in generating human or humanized antibodies using methods and information which are well known in the art. In attempts to discover effective cellular targets for cancer diagnosis and therapy, researchers have sought to identify transmembrane or otherwise tumor-associated polypeptides that are specifically expressed on the surface of one or more particular type(s) of cancer cell as compared to on one or more normal non-cancerous cell(s). Often, such tumor-associated polypeptides are more abundantly expressed on the surface of the cancer cells as compared to on the surface of the non-cancerous cells. The identification of such tumor-associated cell surface antigen polypeptides has given rise to the ability to specifically target cancer cells for destruction via antibody-based therapies.

Examples of TAA include, but are not limited to, TAA (1)-(36) listed below. For convenience, information relating to these antigens, all of which are known in the art, is listed below and includes names, alternative names, Genbank accession numbers and primary reference(s), following nucleic acid and protein sequence identification conventions of the National Center for Biotechnology Information (NCBI). Nucleic acid and protein sequences corresponding to TAA (1)-(36) are available in public databases such as GenBank. Tumor-associated antigens targeted by antibodies include all amino acid sequence variants and isoforms possessing at least about 70%, 80%, 85%, 90%, or 95% sequence identity relative to the sequences identified in the cited references, or which exhibit substantially the same biological properties or characteristics as a TAA having a sequence found in the cited references. For example, a TAA having a variant sequence generally is able to bind specifically to an antibody that binds specifically to the TAA with the corresponding sequence listed. The sequences and disclosure in the reference specifically recited herein are expressly incorporated by reference.

Tumor-Associated Antigens (1)-(36):

(1) BMPR1B (bone morphogenetic protein receptor-type IB, Genbank accession no. NM_001203) ten Dijke, P., et al Science 264 (5155):101-104 (1994), Oncogene 14 (11):1377-1382 (1997)); WO2004/063362 (claim 2); WO2003/042661 (claim 12); US2003/134790-A1 (Page 38-39); WO2002/102235 (claim 13; Page 296); WO2003/055443 (Page 91-92); WO2002/99122 (Example 2; Page 528-530); WO2003/029421 (claim 6); WO2003/024392 (claim 2; FIG. 112); WO2002/98358 (claim 1; Page 183); WO2002/54940 (Page 100-101); WO2002/59377 (Page 349-350); WO2002/30268 (claim 27; Page 376); WO2001/48204 (Example; FIG. 4); NP_001194 bone morphogenetic protein receptor, type IB/pid=NP_001194.1. Cross-references: MIM:603248; NP_001194.1; AY065994

(2) E16 (LAT1, SLC7A5, Genbank accession no. NM_003486) Biochem. Biophys. Res. Commun. 255 (2), 283-288 (1999), Nature 395 (6699):288-291 (1998), Gaugitsch, H. W., et al (1992) J. Biol. Chem. 267 (16):11267-11273); WO2004/048938 (Example 2); WO2004/032842 (Example IV); WO2003/042661 (claim 12); WO2003/016475 (claim 1); WO2002/78524 (Example 2); WO2002/99074 (claim 19; Page 127-129); WO2002/86443 (claim 27; Pages 222, 393); WO2003/003906 (claim 10; Page 293); WO2002/64798 (claim 33; Page 93-95); WO2000/14228 (claim 5; Page 133-136); US2003/224454 (FIG. 3); WO2003/025138 (claim 12; Page 150); NP_003477 solute carrier family 7 (cationic amino acid transporter, y+system), member 5/pid=NP_003477.3-Homo sapiens; Cross-references: MIM:600182; NP_003477.3; NM_015923; NM_003486_1

(3) STEAP1 (six transmembrane epithelial antigen of prostate, Genbank accession no. NM_012449); Cancer Res. 61 (15), 5857-5860 (2001), Hubert, R. S., et al (1999) Proc. Natl. Acad. Sci. U.S.A. 96 (25):14523-14528); WO2004/065577 (claim 6); WO2004/027049 (FIG. 1L); EP1394274 (Example 11); WO2004/016225 (claim 2); WO2003/042661 (claim 12); US2003/157089 (Example 5); US2003/185830 (Example 5); US2003/064397 (FIG. 2); WO2002/89747 (Example 5; Page 618-619); WO2003/022995 (Example 9; FIG. 13A, Example 53; Page 173, Example 2; FIG. 2A); NP_036581 six transmembrane epithelial antigen of the prostate; Cross-references: MIM:604415; NP_036581.1; NM_012449_1

Figure 12:
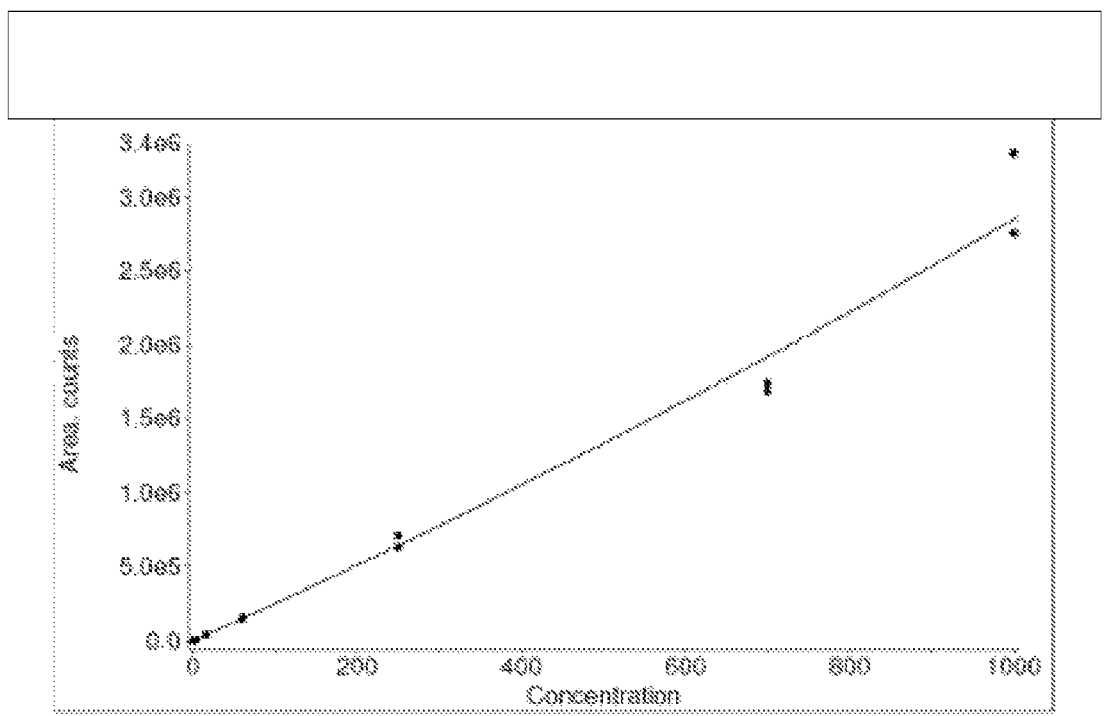
FIG. 12 shows a calibration curve of FSP8 spiked at various concentrations from 1-1000 μg/mL into lithium Heparinised Cynomolgus monkey plasma prepared by the whole plasma digest/SPE approach.

(4) 0772P (CA125, MUC16, Genbank accession no. AF361486); J. Biol. Chem. 276 (29):27371-27375 (2001)); WO2004/045553 (claim 14); WO2002/92836 (claim 6; FIG. 12); WO2002/83866 (claim 15; Page 116-121); US2003/124140 (Example 16); Cross-references: GI:34501467; AAK74120.3; AF361486_1

(5) MPF (MPF, MSLN, SMR, megakaryocyte potentiating factor, mesothelin, Genbank accession no. NM_005823) Yamaguchi, N., et al Biol. Chem. 269 (2), 805-808 (1994), Proc. Natl. Acad. Sci. U.S.A. 96 (20):11531-11536 (1999), Proc. Natl. Acad. Sci. U.S.A. 93 (1):136-140 (1996), J. Biol. Chem. 270 (37):21984-21990 (1995)); WO2003/101283 (claim 14); (WO2002/102235 (claim 13; Page 287-288); WO2002/101075 (claim 4; Page 308-309); WO2002/71928 (Page 320-321); WO94/10312 (Page 52-57); Cross-references: MIM:601051; NP_005814.2; NM_005823_1

(6) Napi3b (NAPI-3B, NPTIIb, SLC34A2, solute carrier family 34 (sodium phosphate), member 2, type II sodium-dependent phosphate transporter 3b, Genbank accession no. NM_006424) J. Biol. Chem. 277 (22):19665-19672 (2002), Genomics 62 (2):281-284 (1999), Feild, J. A., et al (1999) Biochem. Biophys. Res. Commun. 258 (3):578-582); WO2004/022778 (claim 2); EP1394274 (Example 11); WO2002/102235 (claim 13; Page 326); EP0875569 (claim 1; Page 17-19); WO2001/57188 (claim 20; Page 329); WO2004/032842 (Example IV); WO2001/75177 (claim 24; Page 139-140); Cross-references: MIM:604217; NP_006415.1; NM_006424_1

(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane domain (TM) and short cytoplasmic domain, (semaphorin) 5B, Genbank accession no. AB040878); Nagase T., et al (2000) *DNA Res.* 7 (2):143-150); WO2004/000997 (claim 1); WO2003/003984 (claim 1); WO2002/06339 (claim 1; Page 50); WO2001/88133 (claim 1; Page 41-43, 48-58); WO2003/054152 (claim 20); WO2003/101400 (claim 11); Accession: Q9P283; EMBL; AB040878; BAA95969.1. Genew; HGNC:10737

(8) PSCA hlg (2700050C12Rik, C530008O16Rik, RIKEN cDNA 2700050C12, RIKEN cDNA 2700050C12 gene, Genbank accession no. AY358628); Ross et al (2002) *Cancer Res.* 62:2546-2553; US2003/129192 (claim 2); US2004/044180 (claim 12); US2004/044179 (claim 11); US2003/096961 (claim 11); US2003/232056 (Example 5); WO2003/105758 (claim 12); US2003/206918 (Example 5); EP1347046 (claim 1); WO2003/025148 (claim 20); Cross-references: GI:37182378; AAQ88991.1; AY358628_1

(9) ETBR (Endothelin type B receptor, Genbank accession no. AY275463); Nakamuta M., et al *Biochem. Biophys. Res. Commun.* 177, 34-39, 1991; Ogawa Y., et al *Biochem. Biophys. Res. Commun.* 178, 248-255, 1991; Arai H., et al *Jpn. Circ. J.* 56, 1303-1307, 1992; Arai H., et al *J. Biol. Chem.* 268, 3463-3470, 1993; Sakamoto A., Yanagisawa M., et al *Biochem. Biophys. Res. Commun.* 178, 656-663, 1991; Elshourbagy N. A., et al *J. Biol. Chem.* 268, 3873-3879, 1993; Haendler B., et al *J. Cardiovasc. Pharmacol.* 20, s1-S4, 1992; Tsutsumi M., et al *Gene* 228, 43-49, 1999; Strausberg R. L., et al *Proc. Natl. Acad. Sci. U.S.A.* 99, 16899-16903, 2002; Bourgeois C., et al *J. Clin. Endocrinol. Metab.* 82, 3116-3123, 1997; Okamoto Y., et al *Biol. Chem.* 272, 21589-21596, 1997; Verheij J. B., et al *Am. J. Med. Genet.* 108, 223-225, 2002; Hofstra R. M. W., et al *Eur. J. Hum. Genet.* 5, 180-185, 1997; Puffenberger E. G., et al *Cell* 79, 1257-1266, 1994; Attie T., et al, *Hum. Mol. Genet.* 4, 2407-2409, 1995; Auricchio A., et al *Hum. Mol. Genet.* 5:351-354, 1996; Amiel J., et al *Hum. Mol. Genet.* 5, 355-357, 1996; Hofstra R. M. W., et al *Nat. Genet.* 12, 445-447, 1996; Svensson P. J., et al *Hum. Genet.* 103, 145-148, 1998; Fuchs S., et al *Mol. Med.* 7, 115-124, 2001; Pingault V., et al (2002) *Hum. Genet.* 111, 198-206; WO2004/045516 (claim 1); WO2004/048938 (Example 2); WO2004/040000 (claim 151); WO2003/087768 (claim 1); WO2003/016475 (claim 1); WO2003/016475 (claim 1); WO2002/61087 (FIG. 1); WO2003/016494 (FIG. 6); WO2003/025138 (claim 12; Page 144); WO2001/98351 (claim 1; Page 124-125); EP0522868 (claim 8; FIG. 2); WO2001/77172 (claim 1; Page 297-299); US2003/109676; U.S. Pat. No. 6,518,404 (FIG. 3); U.S. Pat. No. 5,773,223 (Claim 1a; Col 31-34); WO2004/001004

(10) MSG783 (RNF124, hypothetical protein F1120315, Genbank accession no. NM_017763); WO2003/104275 (claim 1); WO2004/046342 (Example 2); WO2003/042661 (claim 12); WO2003/083074 (claim 14; Page 61); WO2003/018621 (claim 1); WO2003/024392 (claim 2; FIG. 93); WO2001/66689 (Example 6); Cross-references: LocusID: 54894; NP_060233.2; NM 017763_1

Figure 10:
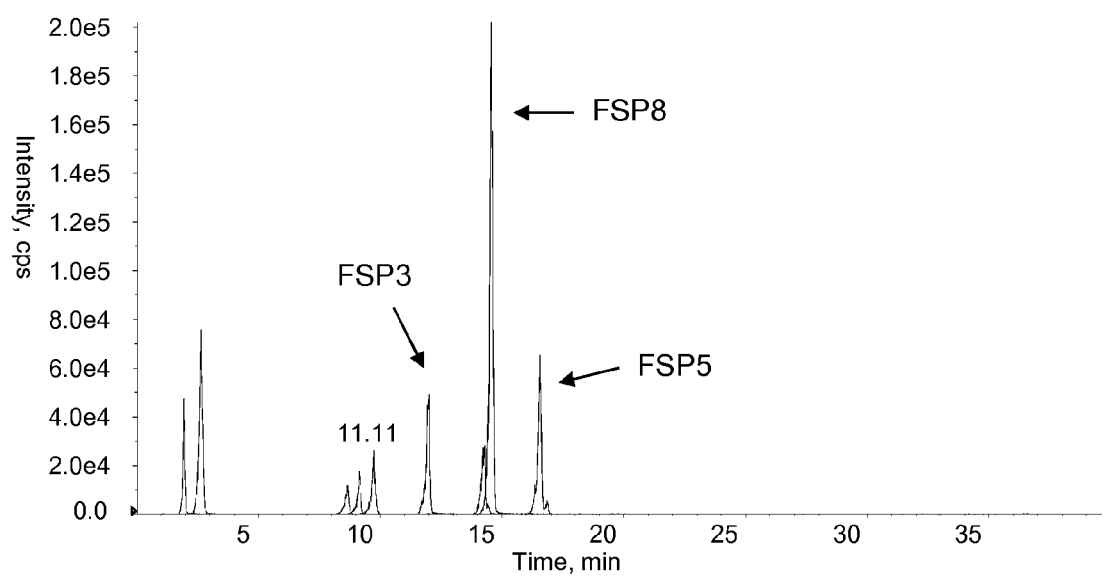
FIG. 10 shows multiple reaction monitoring of trastuzumab digested by trypsin. Framework signature peptides FSP3 (12.5 mins), FSP8 (15 mins) and FSP5 (17 mins) are baseline separated and quantitated.
Figure 11:
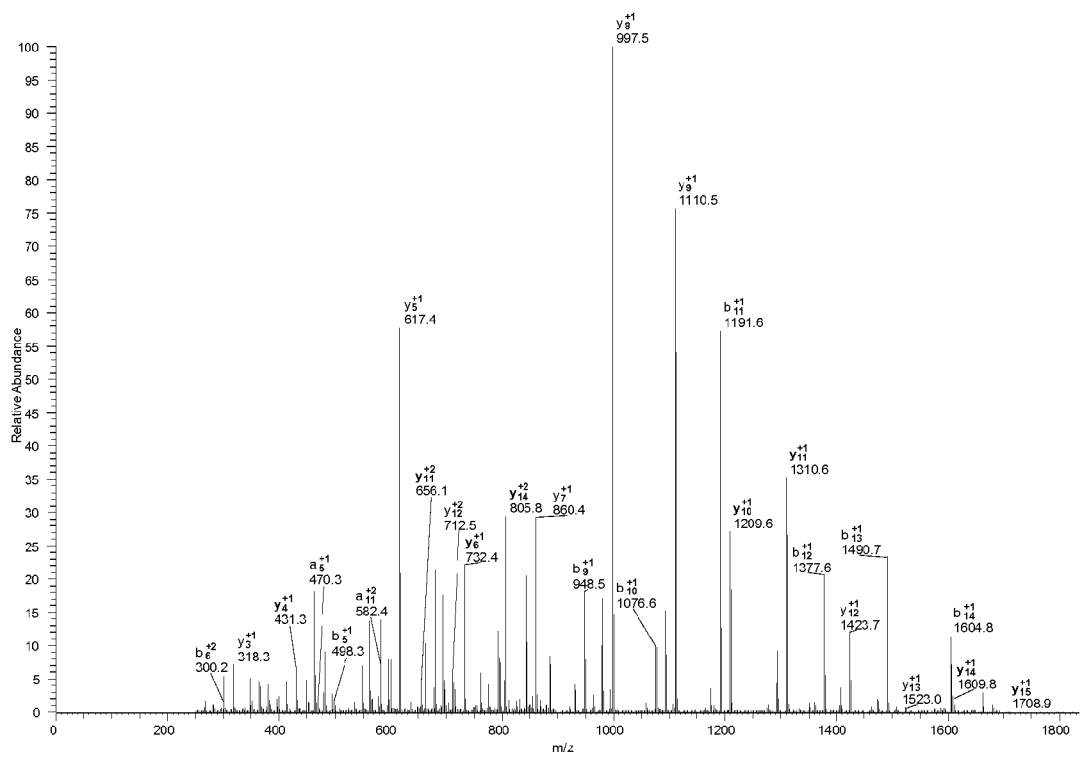
FIG. 11 shows the MS/MS spectrum of FSP5 from affinity-captured then digested anti-MUC16 antibody-drug conjugate that had been spiked into plasma.

(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein, Genbank accession no. AF455138); Lab. Invest. 82 (11):1573-1582 (2002)); WO2003/087306; US2003/064397 (claim 1; FIG. 1); WO2002/72596 (claim 13; Page 54-55); WO2001/72962 (claim 1 FIG. 4B); WO2003/104270 (claim 11); WO2003/104270 (claim 16); US2004/005598 (claim 22); WO2003/042661 (claim 12); US2003/060612 (claim 12; FIG. 10); WO2002/26822 (claim 23; FIG. 2); WO2002/16429 (claim 12; FIG. 10); Cross-references: GI:22655488; AAN04080.1; AF455138_1

(12) TrpM4 (BR22450, FLJ20041, TRPM4, TRPM4B, transient receptor potential cation channel, subfamily M, member 4, Genbank accession no. NM_017636); Xu, X. Z., et al *Proc. Natl. Acad. Sci. U.S.A.* 98 (19):10692-10697 (2001), *Cell* 109 (3):397-407 (2002), *J. Biol. Chem.* 278 (33):30813-30820 (2003)); US2003/143557 (claim 4); WO2000/40614 (claim 14; Page 100-103); WO2002/10382 (claim 1; FIG. 9A); WO2003/042661 (claim 12); WO2002/30268 (claim 27; Page 391); US2003/219806 (claim 4); WO2001/62794 (claim 14; FIG. 1A-D); Cross-references: MIM:606936; NP_060106.2; NM_017636_1

(13) CRIPTO (CR, CR1, CRGF, CRIPTO, TDGF1, teratocarcinoma-derived growth factor, Genbank accession no. NP_003203 or NM_003212); Ciccodicola, A., et al *EMBO J.* 8 (7):1987-1991 (1989), *Am. J. Hum. Genet.* 49 (3):555-565 (1991)); US2003/224411 (Claim 1); WO2003/083041 (Example 1); WO2003/034984 (claim 12); WO2002/88170 (claim 2; Page 52-53); WO2003/024392 (claim 2; FIG. 58); WO2002/16413 (claim 1; Page 94-95, 105); WO2002/22808 (claim 2; FIG. 1); U.S. Pat. No. 5,854,399 (Example 2; Col 17-18); U.S. Pat. No. 5,792,616 (FIG. 2); Cross-references: MIM:187395; NP_003203.1; NM_003212_1

(14) CD21 (CR2 (Complement receptor 2) or C3DR (C3d/Epstein Barr virus receptor) or Hs.73792 Genbank accession no. M26004); Fujisaku et al (1989) *J. Biol. Chem.* 264 (4): 2118-2125); Weis J. J., et al *J. Exp. Med.* 167, 1047-1066, 1988; Moore M., et al *Proc. Natl. Acad. Sci. U.S.A.* 84, 9194-9198, 1987; Barel M., et al *Mol. Immunol.* 35, 1025-1031, 1998; Weis J. J., et al *Proc. Natl. Acad. Sci. U.S.A.* 83, 5639-5643, 1986; Sinha S. K., et al (1993) *J. Immunol.* 150, 5311-5320; WO2004/045520 (Example 4); US2004/005538 (Example 1); WO2003/062401 (claim 9); WO2004/045520 (Example 4); WO91/02536 (FIG. 9.1-9.9); WO2004/020595 (claim 1); Accession: P20023; Q13866; Q14212; EMBL; M26004; AAA35786.1.

(15) CD79b (CD79B, CD79β, IGb (immunoglobulin-associated beta), B29, Genbank accession no. NM_000626 or 11038674); *Proc. Natl. Acad. Sci. U.S.A.* (2003) 100 (7): 4126-4131, *Blood* (2002) 100 (9):3068-3076, Muller et al (1992) *Eur. J. Immunol.* 22 (6):1621-1625); WO2004/016225 (claim 2, FIG. 140); WO2003/087768, US2004/101874 (claim 1, page 102); WO2003/062401 (claim 9); WO2002/78524 (Example 2); US2002/150573 (claim 5, page 15); U.S. Pat. No. 5,644,033; WO2003/048202 (claim 1, pages 306 and 309); WO 99/58658, U.S. Pat. No. 6,534,482 (claim 13, FIG. 17A/B); WO2000/55351 (claim 11, pages 1145-1146); Cross-references: MIM:147245; NP_000617.1; NM_000626_1

Figure 18:
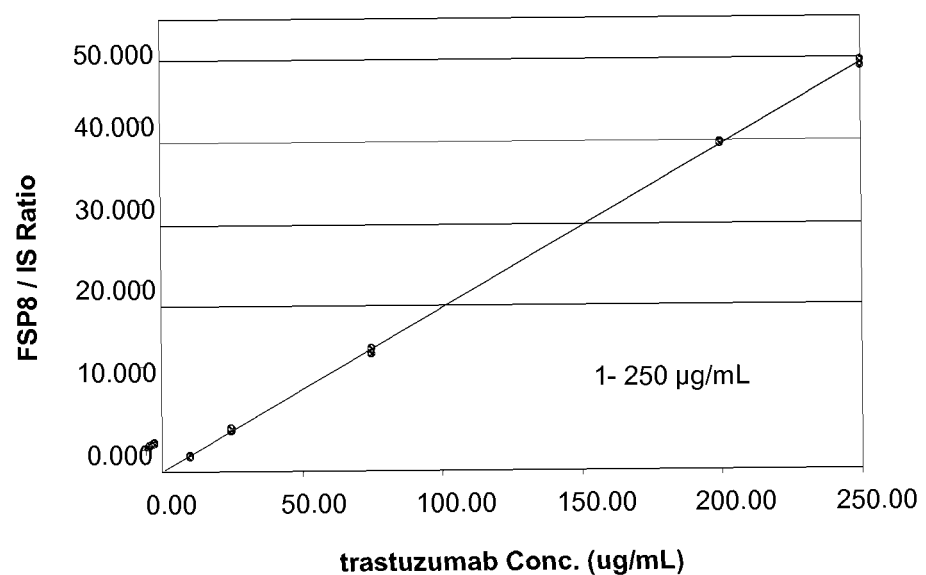
FIG. 18 shows the linearity of detection, plotting the ratio of FSP8 to stable-isotope labelled FSP8 internal standard versus concentration of trastuzumab (HERCEPTIN®) from 1-250 μg/mL in rat plasma.

(16) FcRH2 (IFGP4, IRTA4, SPAP1A (SH2 domain containing phosphatase anchor protein 1a), SPAP1B, SPAP1C, Genbank accession no. NM_030764, AY358130); *Genome Res.* 13 (10):2265-2270 (2003), *Immunogenetics* 54 (2):87-95 (2002), *Blood* 99 (8):2662-2669 (2002), *Proc. Natl. Acad. Sci. U.S.A.* 98 (17):9772-9777 (2001), Xu, M. J., et al (2001) *Biochem. Biophys. Res. Commun.* 280 (3):768-775; WO2004/016225 (claim 2); WO2003/077836; WO2001/38490 (claim 5; FIG. 18D-1-18D-2); WO2003/097803 (claim 12); WO2003/089624 (claim 25); Cross-references: MIM:606509; NP_110391.2; NM_03076_4_1

(17) HER2 (ErbB2, Genbank accession no. M11730); Coussens L., et al *Science* (1985) 230(4730):1132-1139); Yamamoto T., et al *Nature* 319, 230-234, 1986; Semba K., et al *Proc. Natl. Acad. Sci. U.S.A.* 82, 6497-6501, 1985; Swiercz J. M., et al *J. Cell Biol.* 165, 869-880, 2004; Kuhns J. J., et al *J. Biol. Chem.* 274, 36422-36427, 1999; Cho H.-S., et al *Nature* 421, 756-760, 2003; Ehsani A., et al (1993) *Genomics* 15, 426-429; WO2004/048938 (Example 2); WO2004/027049 (FIG. 1I); WO2004/009622; WO2003/081210; WO2003/089904 (claim 9); WO2003/016475 (claim 1); US2003/118592; WO2003/008537 (claim 1); WO2003/055439 (claim 29; FIG. 1A-B); WO2003/025228 (claim 37; FIG. 5C); WO2002/22636 (Example 13; Page 95-107); WO2002/12341 (claim 68; FIG. 7); WO2002/13847 (Page 71-74); WO2002/14503 (Page 114-117); WO2001/53463 (claim 2; Page 41-46); WO2001/41787 (Page 15); WO2000/44899 (claim 52; FIG. 7); WO2000/20579 (claim 3; FIG. 2); U.S. Pat. No. 5,869,445 (claim 3; Col 31-38); WO9630514 (claim 2; Page 56-61); EP1439393 (claim 7); WO2004/043361 (claim 7); WO2004/022709; WO2001/00244 (Example 3; FIG. 4); Accession: P04626; EMBL; M11767; AAA35808.1. EMBL; M11761; AAA35808.1

(18) NCA (CEACAM6, Genbank accession no. M18728); Barnett T., et al *Genomics* 3, 59-66, 1988; Tawaragi Y., et al *Biochem. Biophys. Res. Commun.* 150, 89-96, 1988; Strausberg R. L., et al *Proc. Natl. Acad. Sci. U.S.A.* 99:16899-16903, 2002; WO2004/063709; EP1439393 (claim 7); WO2004/044178 (Example 4); WO2004/031238; WO2003/042661 (claim 12); WO2002/78524 (Example 2); WO2002/86443 (claim 27; Page 427); WO2002/60317 (claim 2); Accession: P40199; Q14920; EMBL; M29541; AAA59915.1. EMBL; M18728

(19) MDP (DPEP1, Genbank accession no. BC017023); *Proc. Natl. Acad. Sci. U.S.A.* 99 (26):16899-16903 (2002)); WO2003/016475 (claim 1); WO2002/64798 (claim 33; Page 85-87); JP05003790 (FIG. 6-8); WO99/46284 (FIG. 9); Cross-references: MIM:179780; AAH17023.1; BC017023_1

(20) IL20Rα (IL20Ra, ZCYTOR7, Genbank accession no. AF184971); Clark H. F., et al *Genome Res.* 13, 2265-2270, 2003; Mungall A. J., et al *Nature* 425, 805-811, 2003; Blumberg H., et al *Cell* 104, 9-19, 2001; Dumoutier L., et al *J. Immunol.* 167, 3545-3549, 2001; Parrish-Novak J., et al *J. Biol. Chem.* 277, 47517-47523, 2002; Pletnev S., et al (2003) *Biochemistry* 42:12617-12624; Sheikh F., et al (2004) *J. Immunol.* 172, 2006-2010; EP1394274 (Example 11); US2004/005320 (Example 5); WO2003/029262 (Page 74-75); WO2003/002717 (claim 2; Page 63); WO2002/22153 (Page 45-47); US2002/042366 (Page 20-21); WO2001/46261 (Page 57-59); WO2001/46232 (Page 63-65); WO98/37193 (claim 1; Page 55-59); Accession: Q9UHF4; Q6UWA9; Q96SH8; EMBL; AF184971; AAF01320.1.

(21) Brevican (BCAN, BEHAB, Genbank accession no. AF229053); Gary S. C., et al *Gene* 256, 139-147, 2000; Clark H. F., et al *Genome Res.* 13, 2265-2270, 2003; Strausberg R. L., et al *Proc. Natl. Acad. Sci. U.S.A.* 99, 16899-16903, 2002; US2003/186372 (claim 11); US2003/186373 (claim 11); US2003/119131 (claim 1; FIG. 52); US2003/119122 (claim 1; FIG. 52); US2003/119126 (claim 1); US2003/119121 (claim 1; FIG. 52); US2003/119129 (claim 1); US2003/119130 (claim 1); US2003/119128 (claim 1; FIG. 52); US2003/119125 (claim 1); WO2003/016475 (claim 1); WO2002/02634 (claim 1)

(22) EphB2R (DRT, ERK, Hek5, EPHT3, Tyro5, Genbank accession no. NM_004442); Chan, J. and Watt, V. M., Oncogene 6 (6), 1057-1061 (1991) Oncogene 10 (5):897-905 (1995), Annu Rev. Neurosci. 21:309-345 (1998), Int. Rev. Cytol. 196:177-244 (2000)); WO2003042661 (claim 12); WO200053216 (claim 1; Page 41); WO2004065576 (claim 1); WO2004020583 (claim 9); WO2003004529 (Page 128-132); WO200053216 (claim 1; Page 42); Cross-references: MIM:600997; NP_004433.2; NM_004442_1

(23) ASLG659 (B7h, Genbank accession no. AX092328); US2004/0101899 (claim 2); WO2003104399 (claim 11); WO2004000221 (FIG. 3); US2003/165504 (claim 1); US2003/124140 (Example 2); US2003/065143 (FIG. 60); WO2002/102235 (claim 13; Page 299); US2003/091580 (Example 2); WO2002/10187 (claim 6; FIG. 10); WO2001/94641 (claim 12; FIG. 7b); WO2002/02624 (claim 13; FIG. 1A-1B); US2002/034749 (claim 54; Page 45-46); WO2002/06317 (Example 2; Page 320-321, claim 34; Page 321-322); WO2002/71928 (Page 468-469); WO2002/02587 (Example 1; FIG. 1); WO2001/40269 (Example 3; Pages 190-192); WO2000/36107 (Example 2; Page 205-207); WO2004/053079 (claim 12); WO2003/004989 (claim 1); WO2002/71928 (Page 233-234, 452-453); WO 01/16318

(24) PSCA (Prostate stem cell antigen precursor, Genbank accession no. AJ297436); Reiter R. E., et al *Proc. Natl. Acad. Sci. U.S.A.* 95, 1735-1740, 1998; Gu Z., et al *Oncogene* 19, 1288-1296, 2000; *Biochem. Biophys. Res. Commun.* (2000) 275(3):783-788; WO2004/022709; EP1394274 (Example 11); US2004/018553 (claim 17); WO2003/008537 (claim 1); WO2002/81646 (claim 1; Page 164); WO2003/003906 (claim 10; Page 288); WO2001/40309 (Example 1; FIG. 17); US2001/055751 (Example 1; FIG. 1b); WO2000/32752 (claim 18; FIG. 1); WO98/51805 (claim 17; Page 97); WO98/51824 (claim 10; Page 94); WO98/40403 (claim 2; FIG. 1B); Accession: 043653; EMBL; AF043498; AAC39607.1

(25) GEDA (Genbank accession No. AY260763); AAP14954 lipoma HMGIC fusion-partner-like protein/pid=AAP14954.1-*Homo sapiens* (human); WO2003/054152 (claim 20); WO2003/000842 (claim 1); WO2003/023013 (Example 3, claim 20); US2003/194704 (claim 45); Cross-references: GI:30102449; AAP14954.1; AY260763_1

(26) BAFF-R (B cell-activating factor receptor, BLyS receptor 3, BR3, Genbank accession No. AF116456); BAFF receptor/pid=NP_443177.1-*Homo sapiens*: Thompson, J. S., et al *Science* 293 (5537), 2108-2111 (2001); WO2004/058309; WO2004/011611; WO2003/045422 (Example; Page 32-33); WO2003/014294 (claim 35; FIG. 6B); WO2003/035846 (claim 70; Page 615-616); WO2002/94852 (Col 136-137); WO2002/38766 (claim 3; Page 133); WO2002/24909 (Example 3; FIG. 3); Cross-references: MIM:606269; NP_443177.1; NM_052945_1; AF132600

(27) CD22 (B-cell receptor CD22-B isoform, BL-CAM, Lyb-8, Lyb8, SIGLEC-2, FLJ22814, Genbank accession No. AK026467); Wilson et al (1991) *J. Exp. Med.* 173:137-146; WO2003/072036 (claim 1; FIG. 1); Cross-references: MIM: 107266; NP_001762.1; NM_001771_1

(28) CD79a (CD79A, CD79α, immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2, Genbank accession No. NP_001774.10); WO2003/088808, US2003/0228319; WO2003/062401 (claim 9); US2002/150573 (claim 4, pages 13-14); WO99/58658 (claim 13, FIG. 16); WO92/07574 (FIG. 1); U.S. Pat. No. 5,644,033; Ha et al (1992) *J. Immunol.* 148(5):1526-1531; Müller et al (1992) *Eur. J. Immunol.* 22:1621-1625; Hashimoto et al (1994) *Immunogenetics* 40(4):287-295; Preud'homme et al (1992) *Clin. Exp. Immunol.* 90(1):141-146; Yu et al (1992) *J. Immunol.* 148(2) 633-637; Sakaguchi et al (1988) *EMBO J.* 7(11):3457-3464

(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3, Genbank accession No. NP_001707.1); WO2004/040000; WO2004/015426; US2003/105292 (Example 2); U.S. Pat. No. 6,555,339 (Example 2); WO2002/61087 (FIG. 1); WO2001/57188 (claim 20, page 269); WO2001/72830 (pages 12-13); WO2000/22129 (Example 1, pages 152-153, Example 2, pages 254-256); WO99/28468 (claim 1, page 38); U.S. Pat. No. 5,440,021 (Example 2, col 49-52); WO94/28931 (pages 56-58); WO92/17497 (claim 7, FIG. 5); Dobner et al (1992) *Eur. J. Immunol.* 22:2795-2799; Barella et al (1995) *Biochem. J.* 309:773-779

(30) HLA-DOB (Beta subunit of MHC class II molecule (Ia antigen) that binds peptides and presents them to CD4+ T lymphocytes); 273 aa, pI: 6.56, MW: 30820.TM: 1 [P] Gene Chromosome: 6p21.3, Genbank accession No. NP_002111.1); Tonnelle et al (1985) *EMBO J.* 4(11):2839-2847; Jonsson et al (1989) *Immunogenetics* 29(6):411-413; Beck et al (1992) *J. Mol. Biol.* 228:433-441; Strausberg et al (2002) *Proc. Natl. Acad. Sci. USA* 99:16899-16903; Servenius et al (1987) *J. Biol. Chem.* 262:8759-8766; Beck et al (1996) *J. Mol. Biol.* 255:1-13; Naruse et al (2002) *Tissue Antigens* 59:512-519; WO99/58658 (claim 13, FIG. 15); U.S. Pat. No. 6,153,408 (Col 35-38); U.S. Pat. No. 5,976,551 (col 168-170); US6011146 (col 145-146); Kasahara et al (1989) *Immunogenetics* 30(1):66-68; Larhammar et al (1985) *J. Biol. Chem.* 260(26):14111-14119

(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3, Genbank accession No. NP_002552.2); Le et al (1997) *FEBS Lett.* 418 (1-2):195-199; WO2004/047749; WO2003/072035 (claim 10); Touchman et al (2000) *Genome Res.* 10:165-173; WO2002/22660 (claim 20); WO2003/093444 (claim 1); WO2003/087768 (claim 1); WO2003/029277 (page 82)

(32) CD72 (B-cell differentiation antigen CD72, Lyb-2); 359 aa, pI: 8.66, MW: 40225, TM: 1 [P] Gene Chromosome: 9p13.3, Genbank accession No. NP_001773.1); WO2004042346 (claim 65); WO2003/026493 (pages 51-52, 57-58); WO2000/75655 (pages 105-106); Von Hoegen et al (1990) J. Immunol. 144(12):4870-4877; Strausberg et al (2002) Proc. Natl. Acad. Sci. USA 99:16899-16903.

(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.2, MW: 74147 TM: 1 [P] Gene Chromosome: 5q12, Genbank accession No. NP_005573.1); US2002/193567; WO97/07198 (claim 11, pages 39-42); Miura et al (1996) *Genomics* 38(3):299-304; Miura et al (1998) *Blood* 92:2815-2822; WO2003/083047; WO97/44452 (claim 8, pages 57-61); WO2000/12130 (pages 24-26)

(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22, Genbank accession No. NP_443170.1); WO2003/077836; WO2001/38490 (claim 6, FIG. 18E-1-18-E-2); Davis et al (2001) *Proc. Natl. Acad. Sci. USA* 98(17):9772-9777; WO2003/089624 (claim 8); EP1347046 (claim 1); WO2003/089624 (claim 7)

(35) IRTA2 (FcRH5, Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21, Genbank accession No. Human:AF343662, AF343663, AF343664, AF343665, AF369794, AF397453, AK090423, AK090475, AL834187, AY358085; Mouse:AK089756, AY158090, AY506558; NP_112571.1; WO2003/024392 (claim 2, FIG. 97); Nakayama et al (2000) *Biochem. Biophys. Res. Commun.* 277(1):124-127; WO2003/077836; WO2001/38490 (claim 3, FIG. 18B-1-18B-2)

(36) TENB2 (TMEFF2, tomoregulin, TPEF, HPP1, TR, putative transmembrane proteoglycan, related to the EGF/heregulin family of growth factors and follistatin); 374 aa, NCBI Accession: AAD55776, AAF91397, AAG49451, NCBI RefSeq: NP_057276; NCBI Gene: 23671; OMIM: 605734; SwissProt Q9UIK5; Genbank accession No. AF179274; AY358907, CAF85723, CQ782436; WO2004/074320; JP2004113151; WO2003/042661; WO2003/009814; EP1295944 (pages 69-70); WO2002/30268 (page 329); WO2001/90304; US2004/249130; US2004/022727; WO2004/063355; US2004/197325; US2003/232350; US2004/005563; US2003/124579; Horie et al (2000) *Genomics* 67:146-152; Uchida et al (1999) *Biochem. Biophys. Res. Commun.* 266:593-602; Liang et al (2000) *Cancer Res.* 60:4907-12; Glynne-Jones et al (2001) *Int J. Cancer.* October 15; 94(2):178-84.

Recombinant Methods and Compositions

Antibodies may be produced using recombinant methods and compositions, e.g., as described in U.S. Pat. No. 4,816,567. In one embodiment, isolated nucleic acid encoding an antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. No. 5,648,237; U.S. Pat. No. 5,789,199; U.S. Pat. No. 5,840,523; Charlton, Methods in *Molecular Biology, Vol.* 248 (B. K. C. Lo, ed., Humana Press, Totowa, N.J., (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern (Gerngross, (2004) *Nat. Biotech.* 22:1409-1414; Li et al. (2006) *Nat. Biotech.* 24:210-215).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts (U.S. Pat. No. 5,959,177; U.S. Pat. No. 6,040,498; U.S. Pat. No. 6,420, 548; U.S. Pat. No. 7,125,978; U.S. Pat. No. 6,417,429, describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al. (1977, *J. Gen Virol.* 36:59); baby hamster kidney cells (BHK); mouse sertoli cells (TM4 cells as described, e.g., in Mather, (1980) *Biol. Reprod.* 23:243-251); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TR1 cells, as described, e.g., in Mather et al. (1982) *Annals N.Y. Acad. Sci.* 383:44-68; MRC 5 cells; and FS4 cells. Other useful mammalian host cell lines include Chinese hamster ovary (CHO) cells, including DHFR$^-$ CHO cells (Urlaub et al. (1980) *Proc. Natl. Acad. Sci. USA* 77:4216); and myeloma cell lines such as Y0, NS0 and Sp2/0. For a review of certain mammalian host cell lines suitable for antibody production, see, e.g., Yazaki and Wu, *Methods in Molecular Biology, Vol.* 248 (B. K. C. Lo, ed., Humana Press, Totowa, N.J.), pp. 255-268 (2003).

Assays

Antibodies may be identified, screened for, or characterized for their physical/chemical properties and/or biological activities by various assays known in the art. In one aspect, an antibody of the invention is tested for its antigen binding activity, e.g., by known methods such as ELISA, Western blot, etc. In another aspect, competition assays may be used to identify an antibody that competes with another known antibody for binding to antigen. In certain embodiments, such a competing antibody binds to the same epitope (e.g., a linear or a conformational epitope) that is bound by the known antibody. Detailed exemplary methods for mapping an epitope to which an antibody binds are provided in Morris (1996) "Epitope Mapping Protocols," in *Methods in Molecular Biology*, Vol. 66 (Humana Press, Totowa, N.J.).

In an exemplary competition assay, immobilized antigen is incubated in a solution comprising a first labeled antibody that binds to antigen (e.g., HER2 or CD20) and a second unlabeled antibody that is being tested for its ability to compete with the first antibody for binding to antigen. The second antibody may be present in a hybridoma supernatant. As a control, immobilized antigen is incubated in a solution comprising the first labeled antibody but not the second unlabeled antibody. After incubation under conditions permissive for binding of the first antibody to antigen, excess unbound antibody is removed, and the amount of label associated with immobilized antigen is measured. If the amount of label associated with immobilized antigen is substantially reduced in the test sample relative to the control sample, then that indicates that the second antibody is competing with the first antibody for binding to antigen. See Harlow and Lane (1988) *Antibodies: A Laboratory Manual* ch. 14 (Cold Spring Harbor Laboratory, Cold Spring Harbor, N.Y.).

In one aspect, assays are provided for identifying antibodies thereof having biological activity. Biological activity may include, e.g., tumor inhibition.

In certain embodiments, antibodies of the methods of the invention are useful for detecting the presence of an antigen in a biological sample. The term "detecting" as used herein encompasses quantitative or qualitative detection. In certain embodiments, a biological sample comprises blood, plasma, serum, cells, urine, vitreous, tears, or tissue. In certain embodiments, the method comprises contacting the biological sample with an antibody as described herein under conditions permissive for binding of the antibody to the antigen, and detecting whether a complex is formed between the antibody and antigen. Such method may be an in vitro or in vivo method. In one embodiment, an antibody is used to select subjects eligible for therapy with an antibody, e.g. where the expressed antigen protein is a biomarker for selection of patients. Exemplary disorders that may be diagnosed using an antibody of the invention include cancer and immune disorders.

Labeled and conjugated antibodies are utilized in certain embodiments of the methods of the invention. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}$P, $^{14}$C, $^{125}$I, $^{3}$H, and $^{131}$I, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737, 456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

Drug moieties which effect cell-killing may be covalently attached to antibodies through a linker unit to form antibody-drug conjugates for targeted cell-killing therapeutic effects. An exemplary embodiment of an antibody-drug conjugate (ADC) compound comprises an antibody (Ab) which targets a tumor cell, and cytotoxic or cytostatic drug moiety (D), and a linker moiety (L) that attaches Ab to D. The antibody is attached through the one or more amino acid residues, such as lysine and cysteine, by the linker moiety (L) to D; the composition having Formula I:

where p is 1 to about 20, or from about 2 to about 5. The number of drug moieties which may be conjugated via a reactive linker moiety to an antibody molecule may be limited by the number of free cysteine residues, which are introduced by the methods described herein.

The drug moiety (D) of an antibody-drug conjugate (ADC) includes any compound, moiety or group that has a cytotoxic or cytostatic effect. Drug moieties may impart their cytotoxic and cytostatic effects by mechanisms including but not limited to tubulin binding, DNA binding or intercalation, and inhibition of RNA polymerase, protein synthesis, and topoisomerase. Some cytotoxic drugs tend to be inactive or less active when conjugated to large antibodies or protein receptor ligands. Exemplary drug moieties include, but are not limited to, a maytansinoid, dolastatin, auristatin, calicheamicin, pyrrolobenzodiazepine (PBD), PNU-159682, anthracycline, duocarmycin, vinca alkaloid, taxane, trichothecene, CC1065, duocarmycin, camptothecin, elinafide, and stereoisomers, isosteres, analogs or derivatives thereof, and including the derivatives of these drugs that have cytotoxic activity.

Antibody-drug conjugates (ADC) are targeted anti-cancer therapeutics designed to reduce nonspecific toxicities and increase efficacy relative to conventional small molecule and antibody cancer chemotherapy. They employ the powerful targeting ability of monoclonal antibodies to specifically deliver highly potent, conjugated small molecule therapeutics to a cancer cell. To evaluate properties such as pharmacokinetics and toxicity of these antibody-drug conjugates, it is useful to be able to characterize and quantitate them from plasma, urine, and other biological samples. Methods to detect and screen antibody-drug conjugates by Immunoaffinity membrane (IAM) capture and mass spectrometry have been disclosed (US 2005/0232929), including bead-based affinity capture methods (US 2009/0286258).

Methods of Measuring Human and Humanized Antibodies in Biological Samples

One aspect of the invention is a reproducible, efficient and economic generic LC-MS/MS-based method for quantification of various human and humanized monoclonal antibody (MAb) therapeutics with a common antibody scaffold structure in cynomolgus monkey and rat plasma and tissue samples, and potentially other non-human species, from preclinical studies. Digestion of antibodies gives peptides from the conserved framework region which are unique to administered human or humanized therapeutic antibodies, and not found in endogenous monkey and rat proteins.

FIG. 9 shows the generic LC-MS/MS method to quantify a therapeutic antibody in animal plasma/serum using one or more framework signature peptides (FSP).

Methods of the invention include a generic approach of quantifying human or humanized antibodies comprising the steps of:
(a) treating a biological sample with a digestive enzyme to form a digested antibody sample, wherein the serum or plasma sample is from an animal that has been treated with a human or humanized antibody; and
(b) analyzing the digested antibody sample by mass spectrometry to detect and measure the concentration of one or more common human framework peptides, wherein the human framework peptides comprise one or more sequences selected from SEQ ID NOS. 1-8.

In one exemplary embodiment, the digestive enzyme is trypsin. Alternative proteases may generate additional framework peptides besides those having SEQ ID NOS. 1-8. Any specific enzyme could be used, such as endoproteinase LysC, endoproteinase ArgC, *staph aureus* V8, and endoproteinase GluC. Non-specific proteases such as papain may be used. The peptides generated for quantitation may have different sequences than with trypsin, but the concept of using a generic framework peptide present in human and not present in animal antibodies is the same.

In another embodiment, the method further comprises contacting the digested antibody sample with an affinity capture media or solid-phase extraction (SPE) sample cleanup and eluting an enriched digested antibody sample.

In another embodiment, the method includes affinity capture the antibody comprising one or more human framework peptides having sequences selected from SEQ ID NOS. 1-8, followed by digestion. The affinity capture method may be achieved by ECD (extra-cellular domain antigen binding), anti-ID capture or Protein A or G.

In another embodiment, the biological sample is serum, plasma, tissue or cell line derived from a non-human mammal.

In an exemplary demonstration of the method, the antibody is anti-HER2 trastuzumab (HERCEPTIN®, Genentech, Inc.). Other antibodies were subjected to the methods of the invention. Antibodies which have been trypsin digested from non-clinical plasma and analyzed include anti-MUC16, anti-MSLN (mesothelin), anti-Steap1, anti-CD20 (2H7 and rituximab), anti-HER3 (2C4, pertuzumab), anti-NRP1, anti-PDLL, anti-LRP6, anti-B7-H4, anti-GFRA1 7C9, anti-NRG1, and anti-LY6E.

In another embodiment, the antibody sample was analyzed with an immunoprecipitation (IP) affinity capture by bead-supported Protein A/G, followed by on-bead digestion and analysis.

Framework Signature Peptides

The framework regions of human antibodies are largely conserved. FIG. 1 shows the sequence alignment of heavy chain amino acid sequences of a human 2H7 antibody ocrelizumab (SEQ ID NO: 11) and five cynomolgus monkey anti-CD20 antibodies: CynoHC 1a D3 1 (SEQ ID NO:12), CynoHC 1b E5 1 (SEQ ID NO:13), Cyno HC 2a (SEQ ID NO:14), CynoHC 2b E6 1 (SEQ ID NO:15), CynoHC 3 (SEQ ID NO:16). Framework signature peptides are identified (FSP 1-8) which are unique to human 2H7 (hu 2H7) Mab and are not present in cynomolgus monkey IgG heavy chain, each bearing at least one amino acid difference in the sequences. Based on the available sequence information, framework signature peptides (FSP1-8) are unique only to the human antibody and not to the cynomolgus IgG variants. The framework signature peptides (FSP 1-8) of Table 2 are also present in endogenous IgG1 and in some cases in IgG2, IgG3, and IgG4. These peptides are also common among other human or humanized therapeutic antibodies and human IgGs.

TABLE 2

| Heavy chain Framework Signature Peptides (FSP 1-8) from Hu MAb | | | |
|---|---|---|---|
| FSP | Sequence | MW | SEQ ID NO: |
| FSP1 | GPSVFPLAPSSK | 1185.6 | 1 |
| FSP2 | STSGGTAALGCLVK | 1263.6 | 2 |
| FSP3 | TPEVTCVVVDVSHEDPEVK | 2081.01 | 3 |

TABLE 2-continued

Heavy chain Framework Signature Peptides
(FSP 1-8) from Hu MAb

| FSP | Sequence | MW | SEQ ID NO: |
|---|---|---|---|
| FSP4 | FNWYVDGVEVHNAK | 1676.8 | 4 |
| FSP5 | VVSVLTVLHQDWLNGK | 1807.0 | 5 |
| FSP6 | ALPAPIEK | 837.5 | 6 |
| FSP7 | GFYPSDIAVEWESNGQPENNYK | 2543.1 | 7 |
| FSP8 | TTPPVLDSDGSFFLYSK | 1872.9 | 8 |

8 framework signature peptides (FSPs) with residues unique (bold) to human IgG

Trastuzumab (HERCEPTIN®, Genentech) was used as a model reference standard and spiked into cynomolgus monkey and rat plasma, followed by direct whole plasma digestion with or without SPE preconcentration or immunoprecipitation by Protein A/G magnetic beads and a subsequent on-bead digestion prior to LC-MS/MS analysis, a working calibration range was established at 1-1000 µg/mL in both plasma matrices. Specificity was also tested and confirmed with both negative control blank plasma and spiked plasma samples.

Trastuzumab (HERCEPTIN®, huMAb4D5-8, rhuMAb HER2, Genentech) is a recombinant DNA-derived humanized, IgG1 kappa, monoclonal antibody version of the murine HER2 antibody which selectively binds with high affinity in a cell-based assay (Kd=5 nM) to the extracellular domain of the human epidermal growth factor receptor2 protein, HER2 (ErbB2) (U.S. Pat. No. 5,821,337; U.S. Pat. No. 6,054,297; U.S. Pat. No. 6,407,213; U.S. Pat. No. 6,639,055; Coussens L, et al (1985) Science 230:1132-9; Slamon D J, et al (1989) Science 244:707-12). Trastuzumab contains human framework regions with the complementarity-determining regions of a murine antibody (4D5) that binds to HER2. Trastuzumab binds to the HER2 antigen and thus inhibits the growth of cancerous cells. Trastuzumab has been shown, in both in vitro assays and in animals, to inhibit the proliferation of human tumor cells that overexpress HER2 (Hudziak R M, et al (1989) Mol Cell Biol 9:1165-72; Lewis G D, et al (1993) Cancer Immunol Immunother; 37:255-63; Baselga J, et al (1998) Cancer Res. 58:2825-2831). Trastuzumab is a mediator of antibody-dependent cellular cytotoxicity, ADCC (Hotaling T E, et al (1996) [abstract]. Proc. Annual Meeting Am Assoc Cancer Res; 37:471; Pegram M D, et al (1997) [abstract]. Proc Am Assoc Cancer Res; 38:602; Sliwkowski et al (1999) Seminars in Oncology 26(4), Suppl 12:60-70; Yarden Y. and Sliwkowski, M. (2001) Nature Reviews: Molecular Cell Biology, Macmillan Magazines, Ltd., Vol. 2:127-137). HERCEPTIN® was approved in 1998 for the treatment of patients with ErbB2-overexpressing metastatic breast cancers (Baselga et al, (1996) J. Clin. Oncol. 14:737-744).

Stable isotope-labeled (SIL) analogs of FSP1-8 (SEQ ID NOS:1-8) can be used as in situ ("spiked in") internal standards. Stable isotope labels typical include $^{13}C$, $^{15}N$, and $^{2}H$. The internal standards can be incorporated into one or more amino acid residues of the peptide sequence. The internal standards can be introduced into the sample before or after digestion, and function to compensate variations occurring during the LC-MS/MS analysis (e.g., changes in autosampler performance, LC separation and MS responses). For example, a stable isotope labeled version of FSP8 was prepared where the lysine between phenylalanine (F) and tyrosine (Y) was labeled with $^{13}C$ and $^{15}N$.

Based on their MS characteristics, FSP8 was empirically chosen due to its most intense signal response as the primary peptide for quantification. In addition, three other peptides, FSP4, FSP5, and FSP3, were monitored for qualitative confirmation. Each of these four peptides could be used as surrogate to quantify the mAb in animal biological matrices. Their corresponding SIL ISs were used in the assay (Table 3). FSP6 can be used only in animal matrices other than cynomolgus monkey since a co-eluting interference background was detected in cynomolgus monkey plasma. Relatively weaker ionization was observed for FSP1, FSP5 and FSP2.

TABLE 3

Corresponding stable-isotope labeled internal standards

| Internal Standard | Amino Acid Sequence | SEQ ID NO: |
|---|---|---|
| FSP8 IS | TTPPVLDSDGSFFL* ($^{13}C_6$, $^{15}N_1$) YSK | 8 |
| FSP4 IS | FNWYVDGVEV* ($^{13}C_5$, $^{15}N_1$) HNAK | 4 |
| FSP5 IS | VVSVLTVLHQDWL* ($^{13}C_6$, $^{15}N_1$) NGK | 5 |
| FSP3 IS | TPEVTcVVVDVSHEDPEV* ($^{13}C_5$, $^{15}N_1$) K | 3 |

*denotes amino acid containing stable isotope labeling
c denotes cysteine residue that has been alkylated with iodoacetamide Human and Humanized Antibodies FIG. 2 shows the heavy chain (SEQ ID NO: 17) and light chain (SEQ ID NO: 18) of trastuzumab (Herceptin®, Genentech Inc.; rhuMAbHER2, Anti p185HER2), a recombinant derived humanized monoclonal antibody, CAS Registry No. 180288-69-1.

FIG. 3 shows the heavy chain (SEQ ID NO: 11) and light chain (SEQ ID NO: 19) of ocrelizumab, rhuMAb 2H7, PRO70769, a humanized anti-CD20 antibody, CAS Registry No. 637334-45-3.

FIG. 4 shows the heavy chain (SEQ ID NO: 20) and light chain (SEQ ID NO: 21) of pertuzumab, rhuMAb 2C4, CAS Registry No. 380610-27-5. FSP2, FSP3, FSP8 are identified as underlined in heavy chain (SEQ ID NO:20).

FIG. 5 shows the heavy chain (SEQ ID NO: 22) and light chain (SEQ ID NO: 23) of anti-PDLL, member of the extended CD28/CTLA-4 family of T cell regulators. FSP2, FSP4, FSP8 are identified as underlined in heavy chain (SEQ ID NO:22).

FIG. 6 shows the heavy chain (SEQ ID NO: 24) and light chain (SEQ ID NO: 25) of anti-neuropilin-1, anti-NRP1, MNRP1685A. FSP2, FSP4, FSP8 are identified as underlined in heavy chain (SEQ ID NO:24). Anti-NRP1 is a recombinant, phage-derived, human monoclonal antibody that specifically targets neuropilin-1 (NRP1), a multi-domain receptor known to bind a variety of ligands, including members of the VEGF family. Anti-NRP1 has demonstrated efficacy in combination with anti-VEGF in mouse xenograft models and strong nonlinear pharmacokinetics across a wide dose range in preclinical species. It is currently being evaluated in Phase I studies as a single agent and in combination with bevacizumab with or without paclitaxel.

FIG. 7 shows the heavy chain (SEQ ID NO: 26) and light chain (SEQ ID NO: 27) of anti-MUC16, DMUC4064A. FSP2, FSP4, FSP8 are identified as underlined in heavy chain (SEQ ID NO:26).

FIG. 8 shows the heavy chain (SEQ ID NO: 28) and light chain (SEQ ID NO: 19) of rituximab, C2B8, MabThera, (Rituxan®, Genentech Inc., Biogen/Idec). FSP2, FSP4, FSP8 are identified as underlined in heavy chain (SEQ ID NO:28). Rituximab (RITUXAN®, Genentech/Biogen Idec; MABTHERA®, Roche, REDITUX®, CAS Reg. No. 174722-31-7) is a genetically engineered chimeric murine/human monoclonal antibody directed against the CD20 antigen. Rituximab is the antibody called "C2B8" in U.S. Pat. No. 5,736,137. Rituximab is indicated for the treatment of patients with relapsed or refractory low-grade or follicular, CD20-positive, B-cell NHL. Rituximab binds to cell surface CD-20 and results in B-cell depletion (Cartron et al (2002) Blood 99: 754-758; Idusogie et al (2000) J. Immunol. 164: 4178-4184; Grillo-López A J, et al (1999) Semin Oncol; 26:66-73; U.S. Pat. No. 5,736,137). RITUXAN (U.S. Pat. No. 5,677,180; U.S. Pat. No. 5,736,137) is the most widely used monoclonal antibody in hematopoietic malignancies and is established in widespread clinical practice. RITUXAN first received FDA approval in 1997 for the treatment of relapsed or refractory, low-grade or follicular, CD20-positive, B-cell non-Hodgkin's lymphoma (NHL). It was also approved in the European Union under the trade name MabThera® in June 1998. In February 2006, RITUXAN also received FDA approval in combination with methotrexate to reduce signs and symptoms in adult patients with moderately-to-severely-active rheumatoid arthritis who have had an inadequate response to one or more TNF antagonist therapies. The amino acid sequence of rituximab antibody (also designated C2B8) and exemplary methods for its production via recombinant expression in Chinese Hamster Ovary (CHO) cells are disclosed in U.S. Pat. No. 5,736,137.

Sample Preparation

Figure 15:
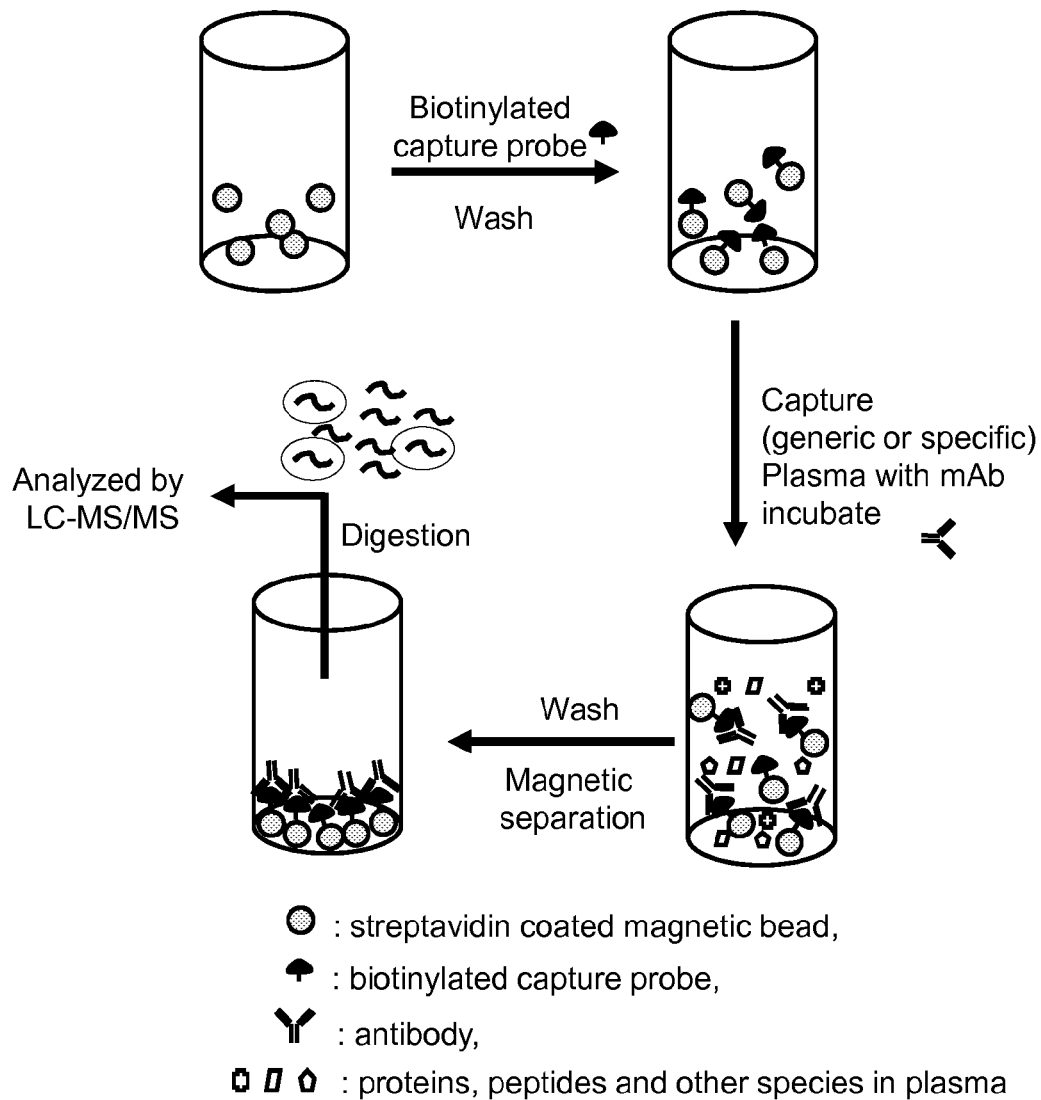
FIG. 15 shows a cartoon of capture of mAb from animal plasma/serum on streptavidin coated magnetic beads bound to a biotinylated capture probe or Protein A, G coated magnetic bead, followed by isolation by magnetic separation, digestion of the captured antibody and analysis by LC-MS/MS.

FIG. 15 shows a cartoon of capture of mAb from animal plasma/serum on streptavidin coated magnetic beads bound to a biotinylated capture probe or Protein A, G coated magnetic bead, followed by isolation by magnetic separation, digestion of the captured antibody and analysis by LC-MS/MS.

FIG. 16 shows embodiments of Protein A, G coated magnetic bead (top) for generic capture of antibody and streptavidin coated magnetic beads bound to a biotinylated capture probe (bottom) for specific capture of antibody.

The potential of immunoprecipitation to efficiently and reproducibly isolate the target monoclonal antibody (MAb) with Protein A was evaluated in two formats: (a) Protein A coupled to magnetic beads and (b) Protein A coated on a 96-well Micro-titer plate. In a preliminary test, a Protein A Micro-titer plate was too capacity limited compared to Protein A magnetic beads in capturing the total applied load of endogenous IgGs along with the target Mab, particularly from monkey plasma. On-bead digestion using Protein A magnetic beads was selected for evaluation for isolation of FSP from both lithium/heparin treated Cynomolgus monkey and Sprague-Dawley rat plasma. Whole plasma digestion followed by solid phase extraction (SPE) was also tested and found to be less effective in removing the interference from background noise.

Separation and Analysis of Biological Samples

Two approaches to assess FSP specificity, detection sensitivity, and reproducibility were investigated: (1) whole plasma digest/SPE (solid phase extraction), and (2) immunoprecipitation (IP).

Monkey (Cynomolgus) and rat plasma sample (n=10 lots each species) were evaluated to assess lot-to-lot specificity, potential interference effects, and reproducibility. Along with a blank plasma control, blank plasma samples were fortified, i.e. "spiked", with 20 µg/ml of trastuzumab. A set of calibrator trastuzumab samples ranging from 1-1000 µg/ml trastuzumab were prepared in pooled plasma matrix and run in parallel with individual monkey and rat plasma samples.

FIG. 12 shows a calibration curve of trastuzumab (using FSP8 as surrogate) spiked at various concentrations from 1-1000 µg/mL into lithium heparin Cynomolgus monkey plasma prepared by the whole plasma digest/SPE approach. Stable isotope-labeled peptide internal standards (ISs) were prepared in 20% acetonitrile to make the working internal standard solution containing the appropriate concentrations.

Figure 14:
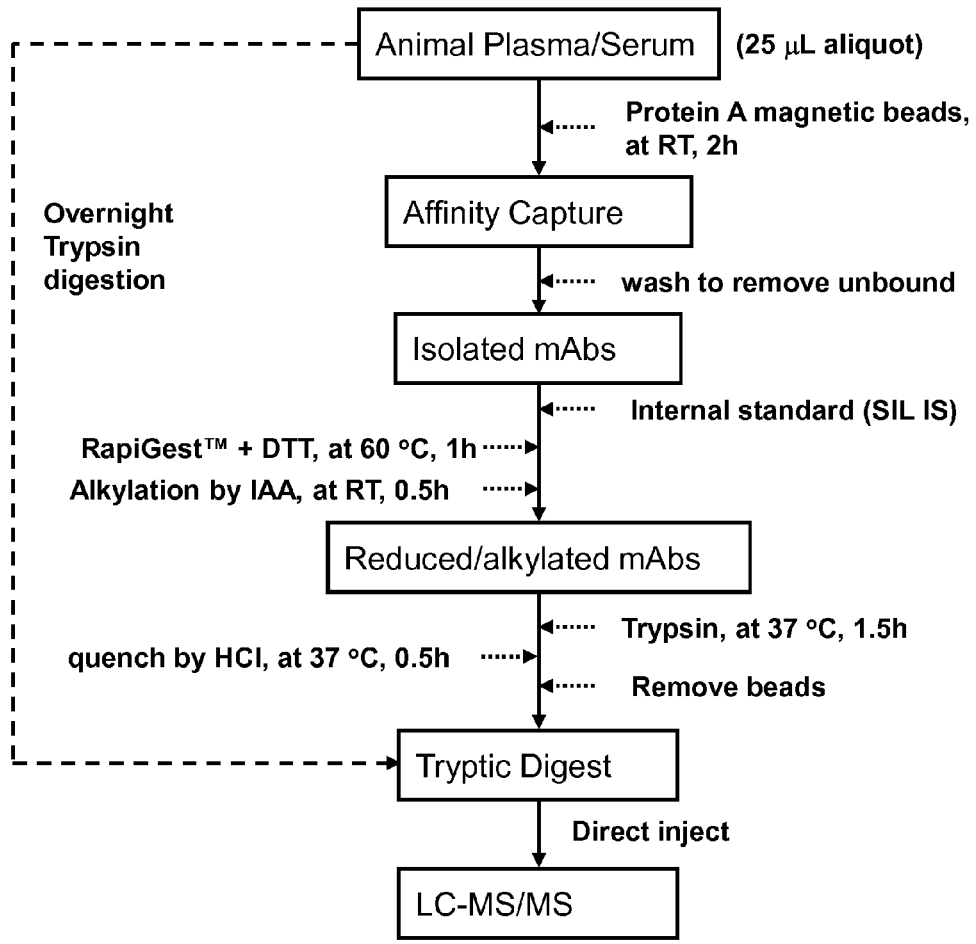
FIG. 14 shows a flow chart of steps for the LC-MS/MS method with affinity capture of the protein therapeutic and enzymatic digestion to generate Framework Signature Peptides (FSP) of mAb in animal plasma/serum.

FIG. 14 shows the steps for immunoprecipitation (IP) of monoclonal antibodies and generating corresponding framework signature peptides (FSPs) in animal plasma or serum. Protocols are defined in Examples 1-4.

Animal samples were prepared by immunoprecipitation (IP) with Protein A paramagnetic beads (Millipore) followed by trypsin digestion. To a 96-well conical-bottom microtiter plate (VWR Scientific), an aliquot of 25 µL diluted plasma or serum [1:2 v/v dilution with loading buffer (SN1) of 0.1:5.0:3.0:0.2:91.7:0.1 Tween 20/Trizma hydrochloride (1 M)/sodium chloride (5 M)/EDTA (0.5 M)/water/BSA, v/v/v/v/v/w] was placed, together with 125 µL loading buffer. An aliquot of 25 µL of Protein A magnetic beads, pre-washed and re-suspended in loading buffer, was added to each well. The mixture was then incubated at room temperature (RT) for 120 minutes under constant mixing to allow the capture of mAbs. The supernatant was discarded and the beads were washed thoroughly in washing buffer (SN2) of 5.0:3.0:0.2:91.8 Trizma hydrochloride (1 M)/sodium chloride (5 M)/EDTA (0.5 M)/water, v/v/v/v). The wash and magnetic separation were performed using a microplate washer (BioTek, VT, USA) and a 96-well flat magnet (Biotek), respectively. The wash/separation process could also be conducted with a KingFisher 96 magnetic particle processor (Thermo Scientific).

Following immunoprecipitation (IP), a 25 µL aliquot of working IS solution was spiked into each well except blanks, where 25 µL of 20% acetonitrile were added instead. Aliquots of 75 µL RapiGest solution (0.05:37.5:10 RapiGest powder/50 mM ammonium bicarbonate/Acetonitrile, w/v/v) and 10 µL of 0.1 M DTT were added. The plate was covered by an adhesive sealing film (VWR Scientific) and shook gently for approximately 1 minute, followed by incubation at 60° C. for 60 minutes. A volume of 25 µL iodoacetic acid (0.1 M) was added, and the plate was covered by an aluminum foil and incubated at room temperature for approximately 30 minutes protected from light. An aliquot of 10 µL trypsin solution (0.250 mg/mL) was added to each well, and the plate was subsequently incubated at 37° C. for approximately 90 minutes. Digestion was terminated by adding 15 µL of 2 M HCl to each well and incubating the plate at 37° C. for 30 minutes. Samples were then transferred by Tomtec (CT, USA) to a Multiscreen HTS filter plate (0.45 µm, Millipore) placed on top of a 96-well, conical-bottom collection plate and centrifuged for 5 minutes at 3000 rpm to collect the filtrate. The collection plate was sealed, and a volume of 20 µL filtrate was injected directly onto LC-MS/MS.

ELISA and LC-MS/MS

Figures 19A, 19B:
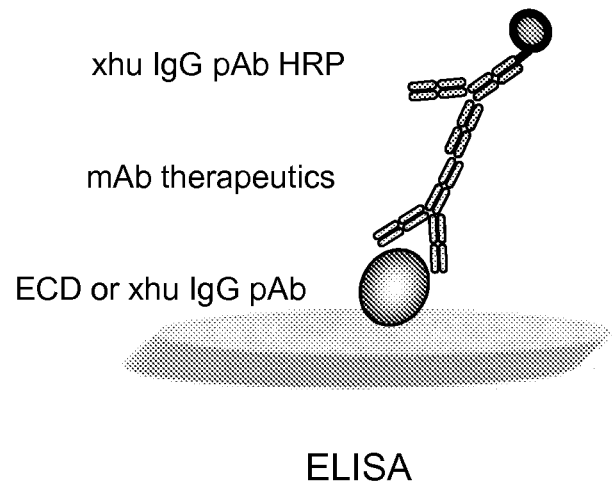
FIG. 19a shows a cartoon of the monoclonal antibody (mAb therapeutics) captured by binding to an immobilized extra-cellular domain (ECD) or anti-human IgG polyclonal antibody and detected with an anti-human IgG polyclonal antibody labeled with horse radish peroxidase (HRP) in an ELISA assay with electrochemiluminescent or colorimetric detection.
FIG. 19b shows elements of the LC-MS/MS assay beginning with Protein A bead capture of an mAb therapeutic from a biological sample, trypsin digestion of the captured mAb therapeutic to form one or more framework signature peptides (FSP), e.g. FSP8, and LC/MS/MS detection of multiple reaction monitoring (MRM) to detect the transition of 938.0 (M, 2+) to 836.7 (y15, 2+).

The ELISA (FIG. 19*a*) and LC-MS/MS (FIG. 19*b*) were compared in measuring total antibody in rat plasma after a single dose of antibody. FIG. 19*a* shows a cartoon of the monoclonal antibody (mAb therapeutics) captured by binding to an immobilized extra-cellular domain (ECD) or anti-human IgG polyclonal antibody, and detected with an anti-human IgG polyclonal antibody labeled with horse radish peroxidase (HRP) in an ELISA assay with electrochemiluminescent, colorometric, or chromophoric substrate detection Liquid chromatographic separation was carried out by either an HP Agilent 1100 Series LC binary system or a Shimadzu LC-10ADvp binary system with a reversed phase BioSuite C18 PA-A column (2.1×50 mm, 3 μm, Waters) operated at a flow rate of 200 μL/min. The column was maintained at 50° C. by a column heater (Analytical Sales and Products, NJ, USA). Mobile phase consisted of A: 0.1% formic acid in water and B: 0.1% formic acid in Acetonitrile/methanol (75:25, v/v). The gradient condition was maintained at 5% B for 0.4 min, ramped to 40% B in 3.4 min, further increased to 95% B in 1 min, kept at 95% B for 0.5 min before brought back to 5% B in 0.1 min. It was then kept at 5% for 0.5 min before being ramped back up to 95% B in 0.1 min, and maintained at the level for 0.5 min to reduce potential carryover. Finally, the gradient was returned to 5% B in 0.1 min and re-equilibrated at 5% B for 0.9 min. The total LC run time was 7.5 min. Samples were injected using a CTC HTS PAL autosampler (LEAP Technologies, NC, USA) with an injector loop of 20 μL. The autosampler wash 1 was Acetonitrile/isopropanol/trifluoroethanol/methanol/water/formic acid (60:15:15:5:5:0.2, by volume) and wash 2 was water/Acetonitrile/formic acid (95:5:0.2, by volume).

A Sciex API 4000® triple quadrupole mass spectrometer (AB Sciex, CA, USA) equipped with a turbo ionspray was used for quantitation. The MS instrument was operated in the positive ion mode with the source temperature set at 500° C. and the ionspray voltage at 5000V. Gas parameters were set with the curtain gas at 25, the nebulizer gas at 45 and the auxiliary gas at 40. A collision gas of 10 was used. Details of the multiple reaction monitoring (MRM) transitions for the signature peptides and their corresponding internal standards are listed in Table 4. The dwell time was set at 50 ms for each MRM transition, and the same entrance potential of 10 V was applied. Both Q1 and Q3 resolutions were set at unit. Quantitation was performed using Intelliquan based on the peak area.

TABLE 4

Multiple reaction monitoring (MRM) transitions for the signature peptides and their corresponding internal standards

| Surrogate Peptide | Peptide Sequence | Q1 (m/z) | Q3 (m/z) | DP | CE | CXP |
|---|---|---|---|---|---|---|
| FSP8 | TTPPVLDSDGSFFLYSK | 938.0 (2+) | 836.7 (y15, 2+) | 90 | 40 | 25 |
| FSP4 | VVSVLTVLHQDWLNGK | 603.5 (3+) | 712.8 (y12, 2+) | 60 | 25 | 20 |
| FSP5 | FNWYVDGVEVHNAK | 560.2 (3+) | 709.3 (y12, 2+) | 95 | 22 | 22 |
| FSP3 | TPEVTcVVVDVSHEDPEVK | 714.0 (3+) | 472.2 (y4) | 75 | 38 | 12 |
| FSP8 IS | TTPPVLDSDGSFFL*YSK | 941.5 (2+) | 840.0 (y15, 2+) | 90 | 40 | 25 |
| FSP4 IS | VVSVLTVLHQDWL*NGK | 605.8 (3+) | 716.3 (y12, 2+) | 60 | 25 | 20 |
| FSP5 IS | FNWYVDGVEV*HNAK | 562.2 (3+) | 712.3 (y12, 2+) | 95 | 22 | 22 |
| FSP3 IS | TPEVTcVVVDVSHEDPEV*K | 716.0 (3+) | 478.2 (y4) | 75 | 38 | 12 |

Lower case "c" indicates the cysteine residue that has been alkylated with iodoacetamide

*denotes amino acid containing stable isotope labeling of $^{13}C_5$ and $^{15}N_1$ Method qualification was performed using trastuzumab as a model. Calibration standards were prepared by spiking trastuzumab into cynomolgus monkey plasma or Sprague-Dawley rat plasma at 1.00, 1.75, 3.00, 10.0, 25.0, 75.0, 200 and 250 μg/mL. Quality controls (QCs) were prepared at 1.00 (LLOQ), 2.50 (LQC), 15.0 (MQC) and 190 μg/mL (UQC) of trastuzumab in plasma. In addition, a dilution QC of 1000 μg/mL original concentration with 10× dilution factor was included. The intra-assay QCs were prepared in 6 replicates and Dilution QC was prepared in 3 replicates. The data of the method qualification is reported in Table 5. Data indicates that the LC-MS/MS assay has good precision and accuracy with values within predefined acceptance criteria.

TABLE 5

Method qualification of precision and accuracy for trastuzumab in rat plasma

| QC | LLOQ 1.00 | LQC 2.50 | MQC 15.0 | UQC 190 | Dil10 QC 1000 |
|---|---|---|---|---|---|
| 1 | 1.01 | 2.42 | 14.2 | 206 | 996 |
| 2 | 1.07 | 2.48 | 15.1 | 203 | 984 |
| 3 | 1.03 | 2.43 | 14.7 | 191 | 1050 |
| 4 | 1.05 | 2.51 | 15.3 | 187 | n/a |
| 5 | 1.12 | 2.76 | 14.8 | 186 | n/a |
| 6 | 1.08 | 2.40 | 14.5 | 183 | n/a |
| Mean | 1.06 | 2.50 | 14.8 | 193 | 1010 |
| SD | 0.0375 | 0.135 | 0.391 | 9.61 | 34.3 |
| % CV | 3.5 | 5.4 | 2.7 | 5.0 | 3.4 |
| % Theoretical | 106.0 | 100.0 | 98.5 | 101.4 | 100.9 |
| % Bias | 6.0 | 0.0 | −1.5 | 1.4 | 0.9 |

Figure 17A:
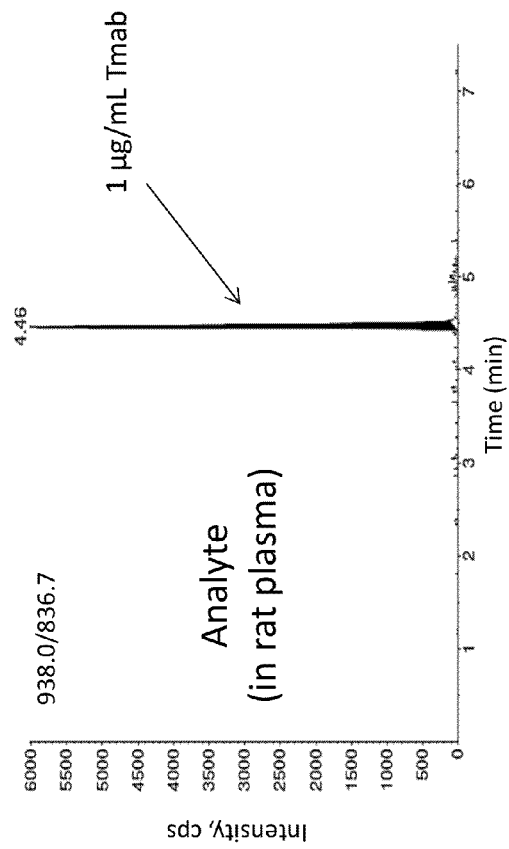
FIG. 17a shows LC-MS/MS separation and detection of FSP8 at 1 μg/mL of trastuzumab antibody in rat plasma.
Figure 17B:
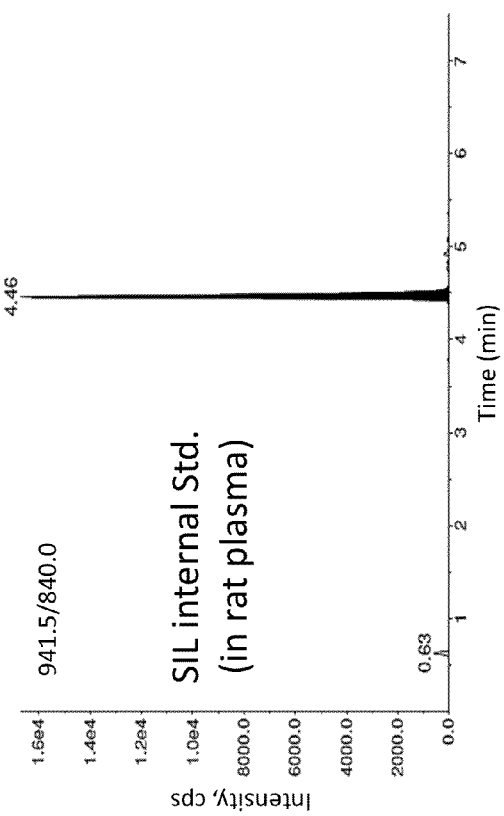
FIG. 17b shows LC-MS/MS separation and detection of stable-isotope labelled (SIL) FSP8 internal standard.

FIG. 17a shows detection of 1 μg/mL (LLOQ) of trastuzumab antibody in rat plasma using FSP8 as surrogate, with stable-isotope labelled FSP8 internal standard (FIG. 17b) detected at the same retention time. Samples were prepared according to the protocol in Example 4. Good linearity was demonstrated from 1-250 μg/mL of trastuzumab in rat plasma in FIG. 18.

FIG. 20 shows the individual concentration time profiles of rats (1A, 1B, 1C) dosed with a 2 mg/kg bolus of trastuzumab, an anti-HER2 mAb. Plasma samples over 28 hours post-dose were analyzed by the LC-MS/MS (FIG. 19b) and ELISA (FIG. 19a) assays. Good concordance was observed between the two assay methods. The PK parameters from FIG. 20 are:

trastuzumab - PK Parameters Mean ± SD[a]

| Assay | CL (mL/d/kg) | V0 (mL/kg) | T½ (d) |
|---|---|---|---|
| ELISA | 6.45 | 41.6 | 9.77 |
| LC-MS/MS | 7.04 | 43.7 | 11.0 |

[a]PK parameters based on n = 2 due to probable ATA (No SD included)

FIG. 21 shows the individual concentration time profiles of rats (2D, 2E, 2F) dosed with a 2 mg/kg bolus of 3A5, an anti-MUC 16 mAb. Plasma samples over 28 hours post-dose were analyzed by the LC-MS/MS (FIG. 19b) and ELISA (FIG. 19a) assays. Good concordance was observed between the two methods. The PK parameters from FIG. 21 are:

Muc16 - PK Parameters Mean ± SD

| Assay | CL (mL/d/kg) | V0 (mL/kg) | T½ (d) |
|---|---|---|---|
| ELISA | 8.25 ± 4.03 | 38.0 ± 1.83 | 8.61 ± 3.77 |
| LCMS | 8.14 ± 3.09 | 42.6 ± 15.1 | 8.09 ± 3.26 |

FIG. 22 shows the results of rats (3G, 3H, 3I) dosed with a 2 mg/kg bolus of an anti-mesothelin (Msln) mAb. Plasma samples over 28 hours were analyzed post-dose by the LC-MS/MS (FIG. 19b) and ELISA (FIG. 19a) assays. Good concordance was observed between the two methods. The PK parameters from FIG. 22 are:

Group 3 Msln - PK Parameters Mean ± SD

| Assay | CL (mL/d/kg) | V0 (mL/kg) | T½ (d) |
|---|---|---|---|
| ELISA | 5.38 ± 0.975 | 50.2 ± 2.10 | 11.6 ± 4.37 |
| LCMS | 6.51 ± 0.896 | 47.1 ± 3.30 | 11.8 ± 1.94 |

Figure 23:
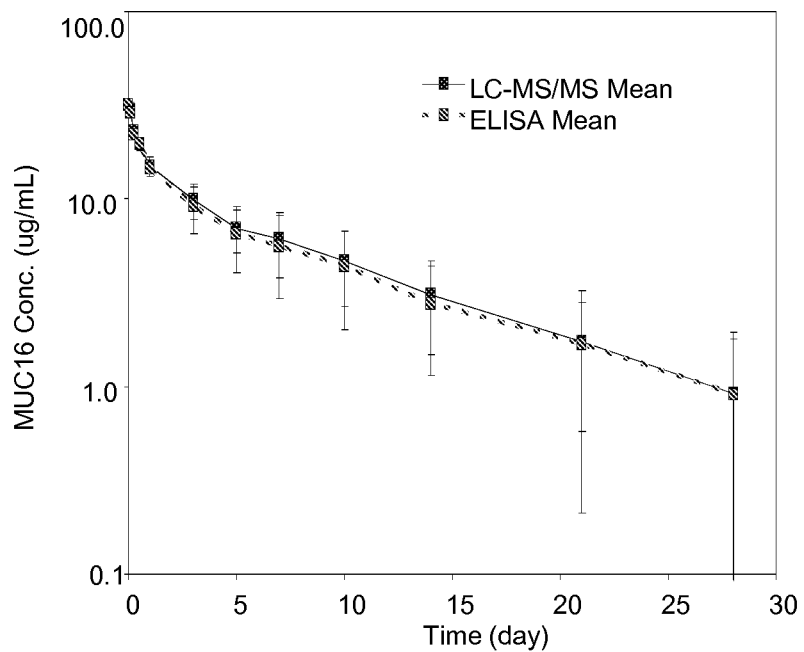
FIG. 23 shows the concordance between the LC-MS/MS assay shown in FIG. 19b and the ELISA assay of FIG. 19a based on mean pharmacokinetics (PK) of plasma/serum samples from cynomolgus monkey dosed with 3A5 (MMUC1206A), an anti-MUC 16 mAb by measurement of antibody in the plasma over 28 days.

FIG. 23 shows the concordance between the LC-MS/MS assay shown in FIG. 19b and the ELISA assay of FIG. 19a based on mean pharmacokinetics (PK) of plasma/serum samples from cynomolgus monkey dosed with 3A5, an anti-MUC 16 mAb by measurement of antibody in the blood over 28 days. The PK parameters from FIG. 23 are:

| Assay | CL (mL/d/kg) | $C_{max}$ (μg/mL) | $T_{1/2}$ (d) |
|---|---|---|---|
| ELISA | 7.86 ± 2.75 | 32.0 ± 2.25 | 7.97 ± 2.72 |
| LC-MS/MS | 7.63 ± 2.64 | 31.6 ± 1.46 | 6.99 ± 2.97 |

All values are Mean ± standard deviation (SD)

Figure 24:
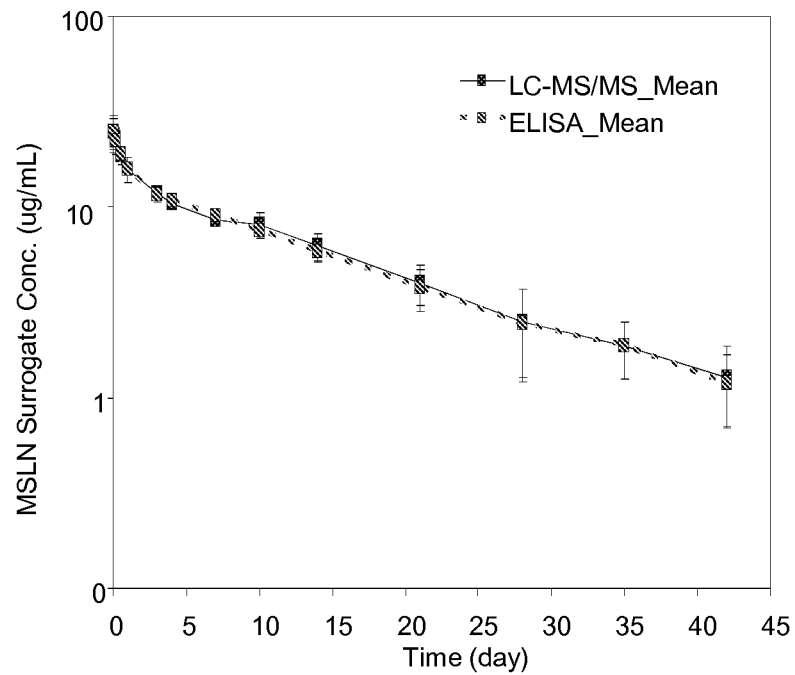
FIG. 24 shows the concordance between the LC-MS/MS assay shown in FIG. 19b and the ELISA assay of FIG. 19a based on mean pharmacokinetics (PK) of plasma/serum samples from cynomolgus monkey dosed with an anti-mesothelin (Msln) mAb by measurement of antibody in the plasma over 40 days.

FIG. 24 shows the concordance between the LC-MS/MS assay shown in FIG. 19b and the ELISA assay of FIG. 19a based on mean pharmacokinetics (PK) of plasma/serum samples from cynomolgus monkey dosed with an anti-mesothelin (Msln) mAb by measurement of antibody in the blood over 42 days. The PK parameters from FIG. 24 are:

| Assay | CL (mL/d/kg) | $C_{max}$ (μg/mL) | $T_{1/2}$ (d) |
|---|---|---|---|
| ELISA | 4.41 ± 0.773 | 24.8 ± 4.63 | 9.51 ± 2.68 |
| LC-MS/MS | 4.26 ± 0.848 | 25.4 ± 4.78 | 11.2 ± 3.52 |

All values are Mean ± standard deviation (SD)

Figure 25:
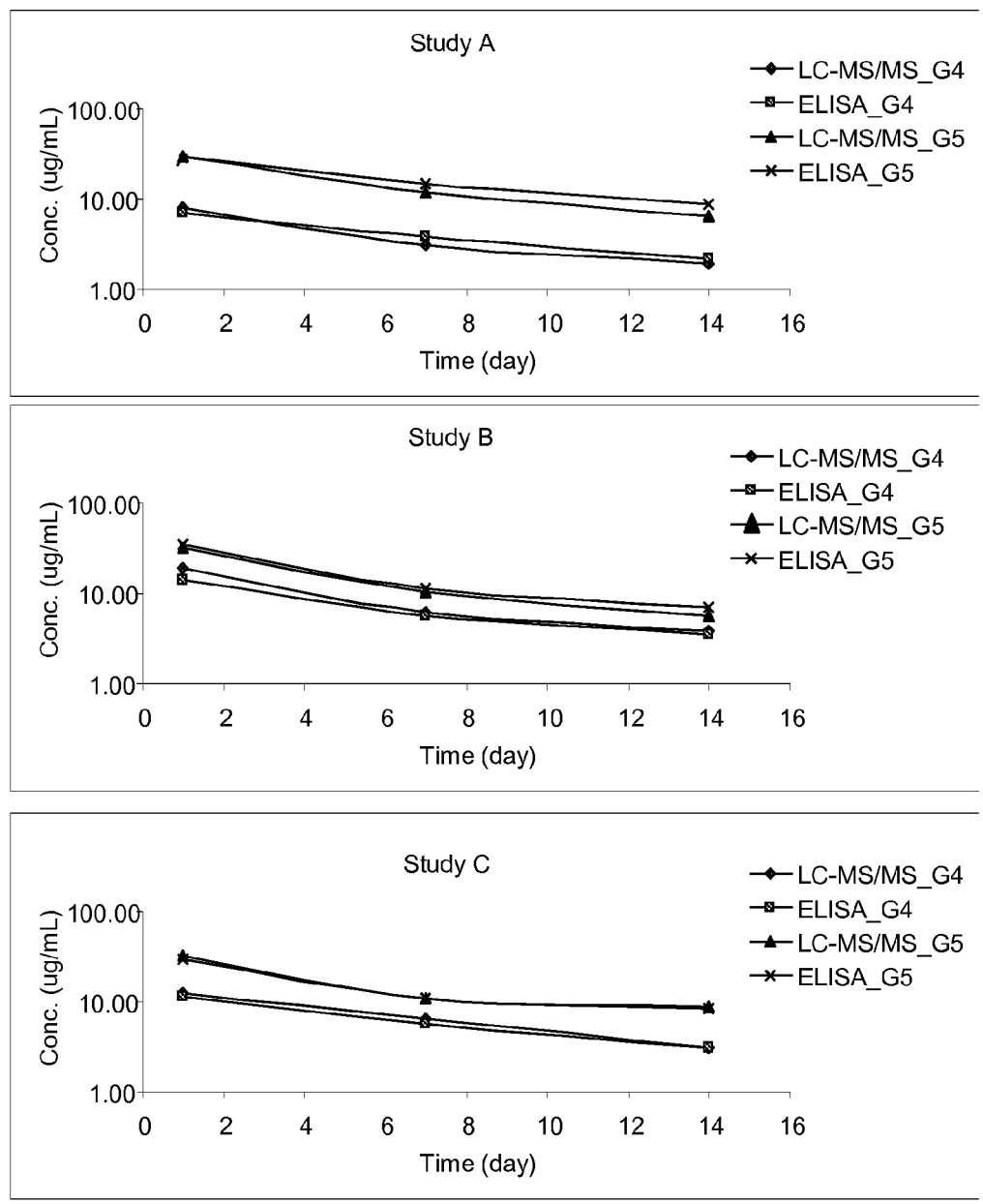
FIG. 25 shows the concordance between the LC-MS/MS assay shown in FIG. 19b and the ELISA assay of FIG. 19a based on individual pharmacokinetics (PK) of plasma/serum samples from mice (A, B, C) dosed with an antibody-drug conjugate (ADC), anti-LY6E-MC-vc-PAB-MMAE, in mouse efficacy studies.

FIG. 25 shows the concordance between the LC-MS/MS assay shown in FIG. 19b and the ELISA assay of FIG. 19a based on individual pharmacokinetics (PK) of plasma/serum samples from mice (A, B, C) dosed with an antibody-drug conjugate, (ADC), anti-LY6E-MC-vc-PAB-MMAE, which has the structure:

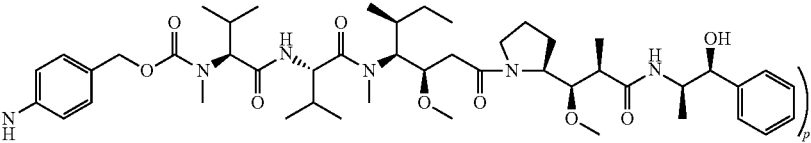

where Ab is an anti-LY6E antibody linked through a cysteine amino acid to the maleimidocaproyl (MC) group of the linker, and by p is the number of drug moieties (MMAE) per antibody in an ADC molecule. The range of p in a typical mixture of ADC is about 0 to about 20, or from 0 to about 8. Where p is 0, a certain amount of naked, unconjugated antibody may be present. The average drug loading per antibody may be about 2 to about 5, or about 3 to about 4. Thus a typical preparation of an antibody-drug conjugate (ADC) is a heterogeneous mixture of species with antibodies conjugated with some number of drug moieties, such as MMAE. The linker also includes a valine-citrulline (Val-Cit) to dipeptide unit susceptible to cathepsin recognition and the para-aminobenzyloxymethyl (PAB) unit (U.S. Pat. No. 7,659,241; U.S. Pat. No. 7,498,298; Doronina et al. (2006) Bioconjugate Chem. 17:114-124; and Doronina et al. (2003) Nat. Biotech. 21:778-784).

The drug moiety MMAE (vedotin, (S)-N-((3R,4S,5S)-1-((S)-2-41R,2R)-3-4(1S,2R)-1-hydroxy-1-phenylpropan-2-yl)amino)-1-methoxy-2-methyl-3-oxopropyl)pyrrolidin-1-yl)-3-methoxy-5-methyl-1-oxoheptan-4-yl)-N,3-dimethyl-2-((S)-3-methyl-2-(methylamino)butanamido)butanamide, CAS Reg. No. 474645-27-7) is a monomethylauristatin analog of dolastatin (U.S. Pat. No. 5,635,483; U.S. Pat. No. 5,780,588) linked through its N-terminus to the antibody. MMAE has the structure:

plasma samples were established. Area ratios and corresponding CV's (coefficient of variation) for different peptides with respect to FSP8 (candidate for primary quantification) have been provided as a gauge of digestion reproducibility. A quadratic (1/conc.$^2$ weighted) regression was used to fit the data.

Figure 13:
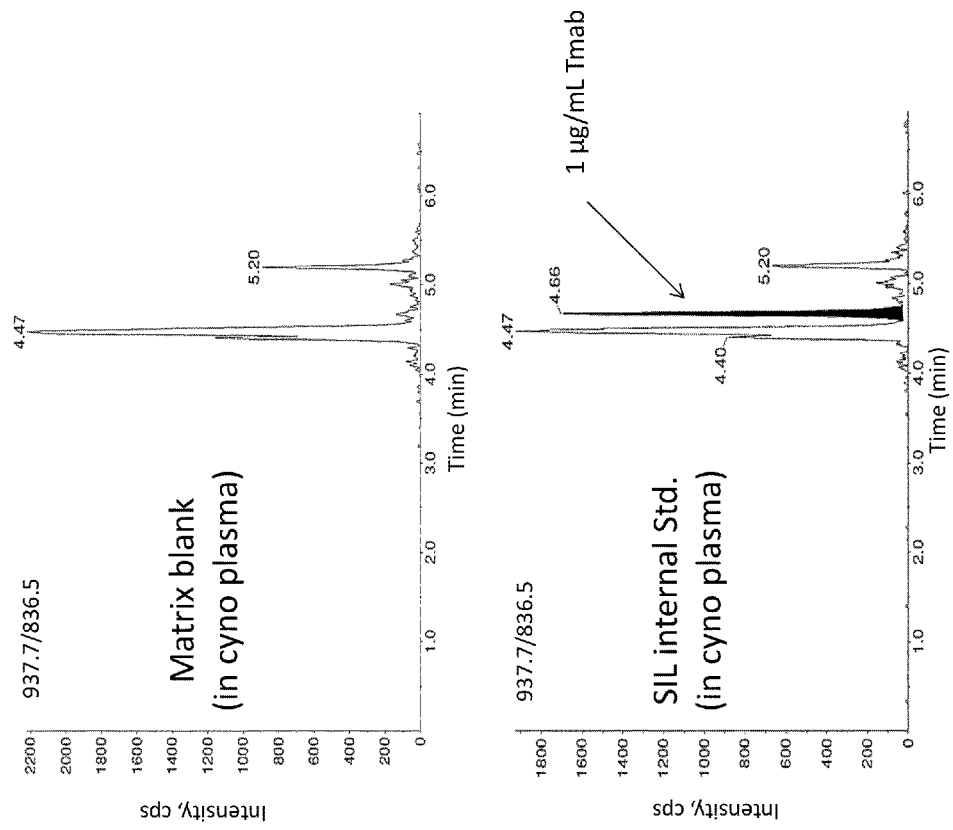
FIG. 13 shows LC-MS/MS chromatograms demonstrating the detection of FSP8 spiked into lithium heparinised cynomolgus monkey plasma at LLOQ=1 μg/mL after whole plasma digest/SPE sample preparation.

In the whole plasma digest/SPE approach to treatment of monkey plasma samples (Example 3b), FSP8 is the most sensitive peptide. FIG. 13 shows LC-MS/MS chromatograms demonstrating the detection of FSP8 spiked into lithium heparinised cynomolgus monkey plasma at LLOQ (lower limit of quantitation)=1 µg/mL after whole plasma digest/SPE sample preparation. Peaks at 4.47 and 5.20 minutes are in the blank. FSP8 has a retention time at 4.66 minutes. The only other peptides quantifiable at low concentrations are FSP4 and FSP5. However, their signal to noise ratio (s/n) at the 1 µg/mL-LLOQ level is less than (<) 5. As expected, peptide NQVSLTCLVK (SEQ ID NO:10) showed high endogenous background levels in all monkey plasma. Nine of the ten individual lots tested had similar and acceptable specificity. Lot#5 had an unusual background level for all quantifiable peptides. The pattern is suggestive that it might be contaminated with some human plasma. Overall, FSP (i.e. spiked) samples showed good accuracy and precision for all lots for FSP8, the potential signature peptide for primary quantitation (exception: FSP7 with a 27% CV). Peak area ratios of FSP4

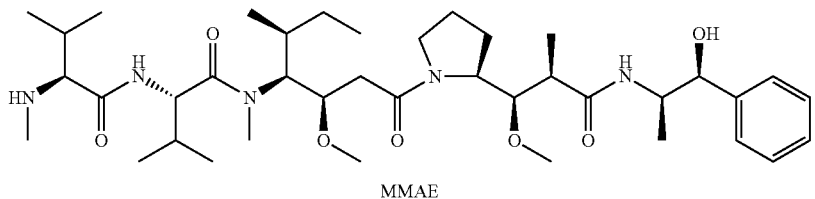 [SMILES: CC[C@H](C)[C@@H]([C@@H](CC(=O)N1CCC[C@H]1[C@H](OC)[C@@H](C)C(=O)N[C@H](C)[C@@H](O)c1ccccc1)OC)N(C)C(=O)[C@@H](NC(=O)[C@@H](NC)C(C)C)C(C)C]

MMAE

The PK profiles and parameters from the two assay methods (LC-MS/MS and ELISA) from the antibody dosing experiment of FIGS. 23-28 show high concordance indicating that quantification of mAbs in animals, including cynomolgus monkeys, rats and mice, by a single generic LC-MS/MS assay using common framework signature peptides as surrogates is feasible and with robust performance. The single MS-based approach is capable of generate reliable PK data that otherwise needs multiple ELISA assays to achieve. In addition, the MS approach doesn't require any custom reagents, which can help accelerate the method development process and make the PK evaluation available at the early stages of drug development.

Data Analysis

Calibration curves were established in the immunoprecipitation approach for: DWYIHWVR (SEQ ID NO:9), FSP3, FSP4, FSP5, FSP8 (all for both monkey and rat) and NQVSLTCLVK (SEQ ID NO:10) (rat only), and in the Whole Plasma Digest/SPE Approach for: FSP4, FSP5, FSP8 (all for both monkey and rat). Specificity data for blank and spiked and FSP5 compared to FSP8 showed CV's less than 20% across different samples and sample types.

In the whole plasma digest/SPE approach to treatment of rat plasma samples (Example 3b), FSP8 is the most intense peptide. The other peptides quantifiable at low level concentrations are FSP4 and FSP5. However, the s/n for these peptides at the LLOQ level is less than 5. The calibration curves showed a split nature, possibly due to signal suppression of later injected samples. None of the individual lots tested, had quantifiable background peaks for all peptides. Due to the split curve, FSP samples showed highly variable accuracy and precision values. Peak area ratios of FSP4 and FSP5 with respect to FSP8 showed CV's greater than 20% in most cases, again pointing out the assay variability.

In the immunoprecipitation approach to treatment of monkey plasma samples (Example 4), FSP8 is the most sensitive, i.e. intense, peptide. All other peptides are also quantifiable at low level concentrations The s/n for all other peptides at the LLOQ level is greater than 5 (except FSP2). As expected, peptide NQVSLTCLVK (SEQ ID NO: 10) showed background levels for all monkey plasma samples. The relationship between concentration and response showed some nonlinearity at high concentrations, possibility due to saturation of the Protein A magnetic beads and/or from competition with endogenous cynomolgus monkey IgGs. Of the 10 individual lots tested, the samples from Lot#5 had background peaks for all quantifiable peptides at a similar level, except for the variable region peptide DTYIHWVR (SEQ ID NO: 9). Overall, the FSP samples showed good accuracy and precision for all lots for FSP8, (including Lot#5 if the background concentration in the blank is taken into account). Peak area ratios of almost all peptides showed CV's less than 15% across different samples and sample types (except FSP5 with a CV for CALS about 23%).

In the immunoprecipitation (IP) approach to treatment of rat plasma samples (Example 4), FSP8 is the most intense peptide. All other peptides are also quantifiable at low level concentrations. The s/n for all other peptides at the LLOQ level is greater than 5 (except FSP2). The relationship between concentration and response showed better linearity that the monkey immunoprecipitation (IP) data, possibility due to less competition from lower affinity endogenous IgGs in Rat plasma. None of the individual lots tested, had quantifiable background peaks for all peptides. Overall, FSP samples showed good accuracy and precision for all lots for FSP8. Peak area ratios of almost all peptides showed CV's less than 20% across different samples and sample types (except FSP5 and FSP2 with a CV for CALS greater than (>) 24%).

The immunoprecipitation (IP) extraction with Protein A magnetic beads showed better sensitivity and reproducibility than whole plasma digest/SPE extraction. The IP approach was faster and "cleaner" than the whole matrix digest/SPE approach.

EXAMPLES

Example 1

Simple Whole Plasma Digestion and Extraction Procedure

1. Aliquot 10 µL of (sodium citrate) plasma into a lo-bind plate
2. Add 95 µL of a 10 mM DTT solution in 50 mM ammonium bicarbonate
3. Mix and incubate at 60° C. for 60 minutes
4. Add 20 µL of 100 mM iodoacetamide (IAA) in 50 mM ammonium bicarbonate
5. Incubate in the dark at room temperature for 30 minutes
6. Leave in the light for 20 minutes
7. Add 15 µL of a 500 µg/mL trypsin solution in 50 mM ammonium bicarbonate
8. Incubate overnight at 37° C.
9. Add 15 µL of a 1% formic acid solution. Mix and centrifuge.
10. Analyze by LC-MS/MS (20 µL injection, at 0.7 mL/min HPLC)

Example 2

Solid-Phase Extraction Protocol for MAX/WCX microElution® Plate (Waters Corp.)

1. Mix 600 µL of serum/plasma digest with 100 µL of 8% H3PO4
2. Condition MAX/WCX µElution SPE plate (Waters Corp., Milford Mass.) with 200 µL of MeOH
3. Equilibrate MAX/WCX µElution SPE plate with 200 µL of H2O
4. Load diluted serum/plasma digest on to the MAX/WCX µElution SPE plate (2×350 µL aliquots). Apply just enough vacuum after each addition to allow the sample to pass through the bed in a drop-wise fashion.
5. Wash with 2004 of 5% NH4OH
6. Wash with 2004 of 20% ACN (acetonitrile)
7. Elute under moderate vacuum with (2×25 µL) of 75:25:1 acetonitrile/water/TFA, v/v/v into a 96-position, 2.0 mL, square-well, conical-bottom, polypropylene plate.
8. Add 200 µL of water and seal the plate with a purple mat seal and vortex for approximately 30 s.
9. Inject 25 µL on the 4000 QTRAP® LC/MS/MS System (AB Sciex, Foster City, Calif., USA)

Example 3a

Whole Plasma Digest Procedure #1

1. Aliquot 10 µL of plasma into a lo-bind plate
2. Add 95 µL of a 10 mM DTT solution in 50 mM ammonium bicarbonate
3. Mix and incubate at 60° C. for 60 minutes
4. Add 20 µL of 100 mM iodoacetamide in 50 mM ammonium bicarbonate
5. Incubate in the dark at room temperature for 30 minutes
6. Leave in the light for 20 minutes
7. Add 15 µL of a 500 µg/mL trypsin in 50 mM ammonium bicarbonate
8. Incubate overnight at 37° C.
9. Add 15 µL of a 1% formic acid solution. Mix and centrifuge.
10. Analyze by LC-MS/MS Example 3b Whole Plasma Digest/SPE (Solid Phase Extraction)—Protocol #2

1. Mix 25 µL of plasma sample with 100 µL of RapiGest™ (Waters Corp., Milford Mass.) SF surfactant solution (0.05:40:10 RapiGest™/Ammonium Acetate, 50 mM/ACN, w/v/v). Add an additional 400 µL of RapiGest™ diluent (80:20 Ammonium Acetate, 50 mM/ACN, v/v).
2. Add 10 µL of DTT (1 M). Incubate at 60° C. for about 1 hour.
3. Add 25 µL of IAA (1M). Incubate at RT for about 0.5 hours protected from light.
4. Add 20 µg of trypsin. Incubate at 37° C. for about 16 hours.
5. Add another dose of 20 µg of trypsin. Incubate at 37° C. for about 4 hours.
6. Add 50 µL of 6M HCl. Incubate at 37° C. for about 0.5 hours.
7. Subject 500 µA of whole plasma digest to SPE using Oasis® MAX µElution plate ((Waters Corp., Milford Mass.)).

8. Mix 500 µL of plasma digest with 100 µL of 8% H3PO4
9. Condition Oasis® MAX µElution SPE plate with 200 µL of MeOH
10. Equilibrate Oasis® MAX µElution SPE plate with 200 µL of H2O
11. Load diluted plasma digest on to the Oasis® MAX µElution SPE plate (2×300 µL aliquots). Apply just enough vacuum to allow the sample to pass through the bed in a drop-wise fashion.
12. Wash with 200 µL of 5% NH4OH
13. Wash with 200 µL of 20% acetonitrile
14. Elute under moderate vacuum with (2×25 µL) of 75:25:1 acetonitrile/water/TFA, v/v/v
15. Add 200 µL of water and seal the plate. Vortex for approximately 30 s.
16. Final volume of SPE eluate is approximately 250 µL. Directly inject 25 µL of this extract.

Example 4

Immunoprecipitation Protocol

1. Gently mix the Protein A bead suspension so that all the beads are uniformly suspended.
2. Pipette the required volume of suspended beads in a polypropylene tube. With the help of an external magnet, separate the beads from the storage buffer, and gently remove the storage buffer with a pipette without disturbing the beads. (note: Calculate the required bead volume based on a 25-µL bead volume required per well).
3. Add a volume of SN1 buffer to the polypropylene tube equal to the initial bead volume. Vortex briefly so that the beads are re-suspended in SN1 buffer.
4. Again with the help of an external magnet, separate the beads from SN1 buffer, and gently remove the SN1 buffer without disturbing the beads.
5. Repeat steps 3-4 two additional times.
6. After washing the beads, again add a volume of SN1 buffer equal to the initial bead volume. Vortex briefly so that the beads are re-suspended in SN1 buffer. The washed bead solution is to be prepared fresh on the day of use. It should be stored at 2-4° if not used within an hour of washing.
7. Vortex the plasma sample and aliquot 25-µL in a microcentrifuge tube.
8. Dilute the plasma sample with 50 µL of SN1 buffer. Vortex briefly.
9. Aliquot 25 µL of the diluted plasma sample in a 96-well microtiter plate.
10. Add 125 µL of SN1 buffer to each well.
11. Add 25 µL of the washed Protein A beads (from step 6) to each well. Ensure that the beads are well suspended in solution prior to adding.
12. Cover the plate with an adhesive sealing film, and shake gently on a titer plate shaker for approximately two hours at room temperature.
13. Using an external magnet and a plate washer, separate the magnetic beads and discard the unbound proteins in the supernatant. Wash the beads three times with SN2 buffer using the plate washer. Ensure that the beads are well suspended in solution prior to each wash step by shaking on a titer plate shaker.
14. Add 25 µL of working internal solution to each well except blanks without internal standard. Add 25 µL of working internal standard diluent to wells containing blanks without internal standard.
15. Add 75 µL of RapiGest solution to each well.
16. Add 10 µL of 0.1 M DTT to each well. Cover the plate with an adhesive sealing film and shake gently on a titer plate shaker for approximately 1 minute.
17. Incubate the plate at 60° C. in a preheated oven for approximately one hour.
18. Add 25 µL of 0.1 M IAA to each well. Cover the plate with an adhesive sealing film and shake gently on a titer plate shaker for approximately 1 minute. These steps should be performed protected from light. Cover the plate with an aluminum foil and incubate at room temperature for approximately 30 minutes.
19. Add 10 µL of trypsin solution to each well. Cover the plate with an adhesive sealing film, and shake gently on a titer plate shaker for approximately 1 minute.
20. Incubate the plate at 37° C. in a preheated incubator for approximately 90 minutes.
21. Add 15 µL of 2 M HCl to each well. Cover the plate with an adhesive sealing film and shake gently on a titer plate shaker for approximately 1 minute.
22. Incubate the plate at 37° C. in a preheated incubator for 30 min.
23. Shake the plate gently on a titer plate shaker for approximately 1 minute. Using the Tomtec, transfer the solution from each well to a Multiscreen HTS Filter Plate placed on top of a 96-well, conical-bottom collection plate.
24. Centrifuge the Multiscreen HTS Filter Plate/96-well conical-bottom collection plate combination for 5 min at 3000 rpm to collect the filtrate in the 96-well, conical-bottom collection plate.
25. Seal the 96-conical-bottom collection plate with a yellow injection mat and inject directly.

SN1 Buffer: 0.1:5.0:3.0:0.2:91.7:0.1 Tween 20/Trizma Hydrochloride (1 M)/Sodium Chloride (5 M)/EDTA (0.5 M)/Water/Bovine Serum Albumin, v/v/v/v/w. This solution is prepared by combining 1 mL of Tween 20, 50.0 mL of 1M Trizma Hydrochloride, 30 mL of 5 M sodium chloride solution, 2 mL of 0.5 M EDTA and 1.00 g of bovine serum albumin in a 1 L volumetric flask. The volume is then made up with water and mixed well to dissolve the bovine serum albumin. It is stored in a closed container at 2-8° C. for up to one month.

SN2 Buffer: 5.0:3.0:0.2:91.8 Trizma Hydrochloride (1 M)/Sodium Chloride (5 M)/EDTA (0.5 M)/Water, v/v/v/v. This solution is prepared by combining 50.0 mL of 1M Trizma Hydrochloride, 30 mL of 5 M sodium chloride solution and 2 mL of 0.5 M EDTA in a 1 L volumetric flask. The volume is then made up with water and mixed well. It is stored in a closed container at 2-8° C. for up to one month.

Exemplary HPLC Method #1:

| | |
|---|---|
| Autosampler | Acquity BSM |
| Strong wash | Acetonitrile |
| Weak wash | Acetonitrile:water 10:90 v/v |
| Injection mode | Full loop |
| LC system | Acquity BSM |
| Flow rate | 0.7 mL/min |
| Analytical Column | 100 × 2.1 mm i.d. Waters Acquity Phenyl |
| Column temperature | Nominally +60° C. |
| Run Time | 7.5 minutes |
| Mobile phase A | Acetonitrile containing 0.2% (v/v) formic acid |
| Mobile phase B | Water containing 0.2% (v/v) formic acid |

Gradient Profile

| Time (mins) | % A | % B |
|---|---|---|
| Initial | 15.0 | 85.0 |
| 3.00 | 17.5 | 82.5 |
| 3.10 | 22.5 | 77.5 |
| 6.00 | 27.5 | 72.5 |
| 6.10 | 95.0 | 5.00 |
| 6.90 | 95.0 | 5.00 |
| 7.00 | 15.0 | 85.0 |
| 7.50 | 15.0 | 85.0 |

Exemplary HPLC Method #2
Column: Waters BioSuite C18 PA-A, 3 μm, 2.1×50 mm (Part#188002425)
Mobile Phase A: 0.1:100 Formic Acid/Water, v/v
Mobile Phase B: 0.1:75:25 Formic Acid/Acetonitrile/Methanol, v/v/v
Flow Rate: 0.20 mL/min
Gradient:

| Time | % A | % B |
|---|---|---|
| 0.00 | 95.0 | 5.0 |
| 0.50 | 95.0 | 5.0 |
| 4.00 | 60.0 | 40.0 |
| 5.00 | 5.0 | 95.0 |
| 5.90 | 5.0 | 95.0 |
| 6.00 | 95.0 | 5.0 |
| 7.00 | 95.0 | 5.0 |

MS/MS Conditions

| | |
|---|---|
| Mass Spectrometer | Applied Biosystems API5500 |
| Ionisation/Interface | TurboIonSpray ™ |
| Source Temperature | 550° C. |
| GS1 | 50 psi |
| GS2 | 50 psi |
| Curtain gas setting | 30 psi |
| Collision gas setting | Medium |
| Ionspray Voltage | 5500 V |

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

We claim:

1. A method of detecting human or humanized antibodies comprising the steps of:
   (a) treating a biological sample comprising a human or humanized antibody with a digestive enzyme to form a digested antibody sample, wherein the biological sample is serum, plasma, tissue, or cells from an animal selected from a cynomolgus monkey, a rat and a mouse that has been treated with said human or humanized antibody; and
   (b) analyzing the digested antibody sample by mass spectrometry to detect one or more human framework peptides, wherein the human framework peptides comprise one or more sequences selected from SEQ ID NOS. 1-8:

| | |
|---|---|
| GPSVFPLAPSSK | SEQ ID NO: 1 |
| STSGGTAALGCLVK | SEQ ID NO: 2 |
| TPEVTCVVVDVSHEDPEVK | SEQ ID NO: 3 |
| FNWYVDGVEVHNAK | SEQ ID NO: 4 |
| VVSVLTVLHQDWLNGK | SEQ ID NO: 5 |
| ALPAPIEK | SEQ ID NO: 6 |
| GFYPSDIAVEWESNGQPENNYK | SEQ ID NO: 7 |
| TTPPVLDSDGSFFLYSK. | SEQ ID NO: 8 |

2. The method of claim 1 wherein the digestive enzyme is trypsin.

3. The method of claim 1 further comprising contacting the digested antibody sample with an affinity capture media or chromatography adsorbent and eluting said enriched digested antibody sample.

4. The method of claim 1 further comprising contacting the biological sample with an affinity capture media or chromatography adsorbent and eluting said enriched biological sample then treating the enriched biological sample with the digestive enzyme.

5. The method of claim 3 or 4 wherein the affinity capture media is bead-supported Protein A/G.

6. The method of claim 3 or 4 wherein the chromatography adsorbent is a solid-phase extraction (SPE) adsorbent.

7. The method of claim 1 wherein the biological sample is serum or plasma.

8. The method of claim 1 wherein the concentration of digested antibody sample is measured.

9. The method of claim 1 wherein the human or humanized antibody binds to one or more tumor-associated antigens or cell-surface receptors selected from (1)-(36):
   (1) BMPR1B (bone morphogenetic protein receptor-type IB);
   (2) E16 (LAT1, SLC7A5);
   (3) STEAP1 (six transmembrane epithelial antigen of prostate);
   (4) 0772P (CA125, MUC16);

(5) MPF (MPF, MSLN, SMR, megakaryocyte potentiating factor, mesothelin);
(6) Napi3b (NAPI-3B, NPTIIb, SLC34A2, solute carrier family 34 (sodium phosphate), member 2, type II sodium-dependent phosphate transporter 3b);
(7) Sema 5b (F1110372, KIAA1445, Mm.42015, SEMASB, SEMAG, Semaphorin 5b Hlog, sema domain, seven thrombospondin repeats (type 1 and type 1-like), transmembrane domain (TM) and short cytoplasmic domain, (semaphorin) 5B);
(8) PSCA hlg;
(9) ETBR (Endothelin type B receptor);
(10) MSG783 (RNF124, hypothetical protein F1120315);
(11) STEAP2 (HGNC 8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein);
(12) TrpM4 (BR22450, F1120041, TRPM4, TRPM4B, transient receptor potential cation channel, subfamily M, member 4);
(13) CRIPTO (CR, CR1, CRGF, CRIPTO, TDGF1, teratocarcinoma-derived growth factor);
(14) CD21 (CR2 (Complement receptor 2) or C3DR (C3d/Epstein Barr virus receptor) or Hs 73792);
(15) CD79b (CD79B, CD79β, IGb (immunoglobulin-associated beta), B29);
(16) FcRH2 (IFGP4, IRTA4, SPAP1A (SH2 domain containing phosphatase anchor protein 1a), SPAP1B, SPAP1C);
(17) HER2 (ErbB2);
(18) NCA;
(19) MDP;
(20) IL20Rα;
(21) Brevican;
(22) EphB2R;
(23) ASLG659;
(24) PSCA;
(25) GEDA;
(26) BAFF-R (B cell-activating factor receptor, BLyS receptor 3, BR3);
(27) CD22 (B-cell receptor CD22-B isoform);
(28) CD79a (CD79A, CD79α, immunoglobulin-associated alpha);
(29) CXCR5 (Burkitt's lymphoma receptor 1);
(30) HLA-DOB (Beta subunit of MHC class II molecule (Ia antigen));
(31) P2X5 (Purinergic receptor P2X ligand-gated ion channel 5);
(32) CD72 (B-cell differentiation antigen CD72, Lyb-2);
(33) LY64 (Lymphocyte antigen 64 (RP105), type I membrane protein of the leucine rich repeat (LRR) family);
(34) FcRH1 (Fc receptor-like protein 1);
(35) IRTA2 (FcRH5, Immunoglobulin superfamily receptor translocation associated 2); and
(36) TENB2 (putative transmembrane proteoglycan).

10. The method of claim 1 wherein the human or humanized antibody is selected from trastuzumab, ocrelizumab, pertuzumab, anti-PDLL, anti-neuropilin-1, anti-MUC16, rituximab, anti-mesothelin, and anti-LY6E.

11. The method of claim 1 wherein the human or humanized antibody is conjugated to a drug moiety.

12. The method of claim 11 wherein the drug moiety is selected from a maytansinoid, dolastatin, auristatin, calicheamicin, pyrrolobenzodiazepine (PBD), PNU-159682, anthracycline, duocarmycin, vinca alkaloid, taxane, trichothecene, CC1065, duocarmycin, camptothecin, elinafide, and stereoisomers, isosteres, analogs or derivatives thereof.

* * * * *

SEQUENCE LISTING

```
<160> NUMBER OF SEQ ID NOS: 29

<210> SEQ ID NO 1
<211> LENGTH: 12
<212> TYPE: PRT
<213> ORGANISM: Artificial sequence
<220> FEATURE:
<223> OTHER INFORMATION: sequence is synthesized

<400> SEQUENCE: 1

Gly Pro Ser Val Phe Pro Leu Ala Pro Ser Ser Lys
  1               5                  10

<210> SEQ ID NO 2
<211> LENGTH: 14
<212> TYPE: PRT
<213> ORGANISM: Artificial sequence
<220> FEATURE:
<223> OTHER INFORMATION: sequence is synthesized

<400> SEQUENCE: 2

Ser Thr Ser Gly Gly Thr Ala Ala Leu Gly Cys Leu Val Lys
  1               5                  10

<210> SEQ ID NO 3
<211> LENGTH: 19
<212> TYPE: PRT
<213> ORGANISM: Artificial sequence
<220> FEATURE:
<223> OTHER INFORMATION: sequence is synthesized

<400> SEQUENCE: 3

Thr Pro Glu Val Thr Cys Val Val Val Asp Val Ser His Glu Asp
  1               5                  10                  15

Pro Glu Val Lys
```

```
<210> SEQ ID NO 4
<211> LENGTH: 14
<212> TYPE: PRT
<213> ORGANISM: Artificial sequence
<220> FEATURE:
<223> OTHER INFORMATION: sequence is synthesized

<400> SEQUENCE: 4

Phe Asn Trp Tyr Val Asp Gly Val Glu Val His Asn Ala Lys
  1               5                  10

<210> SEQ ID NO 5
<211> LENGTH: 16
<212> TYPE: PRT
<213> ORGANISM: Artificial sequence
<220> FEATURE:
<223> OTHER INFORMATION: sequence is synthesized

<400> SEQUENCE: 5

Val Val Ser Val Leu Thr Val Leu His Gln Asp Trp Leu Asn Gly
  1               5                  10                  15

Lys

<210> SEQ ID NO 6
<211> LENGTH: 8
<212> TYPE: PRT
<213> ORGANISM: Artificial sequence
<220> FEATURE:
<223> OTHER INFORMATION: sequence is synthesized

<400> SEQUENCE: 6

Ala Leu Pro Ala Pro Ile Glu Lys
  1               5

<210> SEQ ID NO 7
<211> LENGTH: 22
<212> TYPE: PRT
<213> ORGANISM: Artificial sequence
<220> FEATURE:
<223> OTHER INFORMATION: sequence is synthesized

<400> SEQUENCE: 7

Gly Phe Tyr Pro Ser Asp Ile Ala Val Glu Trp Glu Ser Asn Gly
  1               5                  10                  15

Gln Pro Glu Asn Asn Tyr Lys
                 20

<210> SEQ ID NO 8
<211> LENGTH: 17
<212> TYPE: PRT
<213> ORGANISM: Artificial sequence
<220> FEATURE:
<223> OTHER INFORMATION: sequence is synthesized

<400> SEQUENCE: 8

Thr Thr Pro Pro Val Leu Asp Ser Asp Gly Ser Phe Phe Leu Tyr
  1               5                  10                  15

Ser Lys

<210> SEQ ID NO 9
<211> LENGTH: 8
<212> TYPE: PRT
<213> ORGANISM: Artificial sequence
<220> FEATURE:
<223> OTHER INFORMATION: sequence is synthesized
```

-continued

<400> SEQUENCE: 9

Asp Trp Tyr Ile His Trp Val Arg
1               5

<210> SEQ ID NO 10
<211> LENGTH: 10
<212> TYPE: PRT
<213> ORGANISM: Artificial sequence
<220> FEATURE:
<223> OTHER INFORMATION: sequence is synthesized

<400> SEQUENCE: 10

Asn Gln Val Ser Leu Thr Cys Leu Val Lys
1               5                   10

<210> SEQ ID NO 11
<211> LENGTH: 452
<212> TYPE: PRT
<213> ORGANISM: Artificial sequence
<220> FEATURE:
<223> OTHER INFORMATION: sequence is synthesized

<400> SEQUENCE: 11

Glu Val Gln Leu Val Glu Ser Gly Gly Gly Leu Val Gln Pro Gly
1               5                   10                  15

Gly Ser Leu Arg Leu Ser Cys Ala Ala Ser Gly Tyr Thr Phe Thr
                20                  25                  30

Ser Tyr Asn Met His Trp Val Arg Gln Ala Pro Gly Lys Gly Leu
                35                  40                  45

Glu Trp Val Gly Ala Ile Tyr Pro Gly Asn Gly Asp Thr Ser Tyr
                50                  55                  60

Asn Gln Lys Phe Lys Gly Arg Phe Thr Ile Ser Val Asp Lys Ser
                65                  70                  75

Lys Asn Thr Leu Tyr Leu Gln Met Asn Ser Leu Arg Ala Glu Asp
                80                  85                  90

Thr Ala Val Tyr Tyr Cys Ala Arg Val Val Tyr Tyr Ser Asn Ser
                95                  100                 105

Tyr Trp Tyr Phe Asp Val Trp Gly Gln Gly Thr Leu Val Thr Val
                110                 115                 120

Ser Ser Ala Ser Thr Lys Gly Pro Ser Val Phe Pro Leu Ala Pro
                125                 130                 135

Ser Ser Lys Ser Thr Ser Gly Gly Thr Ala Ala Leu Gly Cys Leu
                140                 145                 150

Val Lys Asp Tyr Phe Pro Glu Pro Val Thr Val Ser Trp Asn Ser
                155                 160                 165

Gly Ala Leu Thr Ser Gly Val His Thr Phe Pro Ala Val Leu Gln
                170                 175                 180

Ser Ser Gly Leu Tyr Ser Leu Ser Ser Val Val Thr Val Pro Ser
                185                 190                 195

Ser Ser Leu Gly Thr Gln Thr Tyr Ile Cys Asn Val Asn His Lys
                200                 205                 210

Pro Ser Asn Thr Lys Val Asp Lys Lys Val Glu Pro Lys Ser Cys
                215                 220                 225

Asp Lys Thr His Thr Cys Pro Pro Cys Pro Ala Pro Glu Leu Leu
                230                 235                 240

Gly Gly Pro Ser Val Phe Leu Phe Pro Pro Lys Pro Lys Asp Thr
                245                 250                 255

```
Leu Met Ile Ser Arg Thr Pro Glu Val Thr Cys Val Val Asp
            260                 265                 270

Val Ser His Glu Asp Pro Glu Val Lys Phe Asn Trp Tyr Val Asp
        275                 280                 285

Gly Val Glu Val His Asn Ala Lys Thr Lys Pro Arg Glu Glu Gln
        290                 295                 300

Tyr Asn Ser Thr Tyr Arg Val Val Ser Val Leu Thr Val Leu His
        305                 310                 315

Gln Asp Trp Leu Asn Gly Lys Glu Tyr Lys Cys Lys Val Ser Asn
        320                 325                 330

Lys Ala Leu Pro Ala Pro Ile Glu Lys Thr Ile Ser Lys Ala Lys
        335                 340                 345

Gly Gln Pro Arg Glu Pro Gln Val Tyr Thr Leu Pro Pro Ser Arg
        350                 355                 360

Glu Glu Met Thr Lys Asn Gln Val Ser Leu Thr Cys Leu Val Lys
        365                 370                 375

Gly Phe Tyr Pro Ser Asp Ile Ala Val Glu Trp Glu Ser Asn Gly
        380                 385                 390

Gln Pro Glu Asn Asn Tyr Lys Thr Thr Pro Pro Val Leu Asp Ser
        395                 400                 405

Asp Gly Ser Phe Phe Leu Tyr Ser Lys Leu Thr Val Asp Lys Ser
        410                 415                 420

Arg Trp Gln Gln Gly Asn Val Phe Ser Cys Ser Val Met His Glu
        425                 430                 435

Ala Leu His Asn His Tyr Thr Gln Lys Ser Leu Ser Leu Ser Pro
        440                 445                 450

Gly Lys

<210> SEQ ID NO 12
<211> LENGTH: 328
<212> TYPE: PRT
<213> ORGANISM: Artificial sequence
<220> FEATURE:
<223> OTHER INFORMATION: sequence is synthesized

<400> SEQUENCE: 12

Ala Ser Thr Lys Gly Pro Ser Val Phe Pro Leu Ala Pro Ser Ser
 1               5                  10                  15

Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ser
        35                  40                  45

Leu Thr Ser Gly Val His Thr Phe Pro Ala Val Leu Gln Ser Ser
        50                  55                  60

Gly Leu Tyr Ser Leu Ser Ser Val Val Thr Val Pro Ser Ser Ser
        65                  70                  75

Leu Gly Thr Gln Thr Tyr Val Cys Asn Val Asn His Lys Pro Ser
        80                  85                  90

Asn Thr Lys Val Asp Lys Arg Val Glu Ile Lys Thr Cys Gly Gly
        95                  100                 105

Gly Ser Lys Pro Pro Thr Cys Pro Pro Cys Pro Ala Pro Glu Leu
        110                 115                 120

Leu Gly Gly Pro Ser Val Phe Leu Phe Pro Pro Lys Pro Lys Asp
        125                 130                 135

Thr Leu Met Ile Ser Arg Thr Pro Glu Val Thr Cys Val Val Val
        140                 145                 150
```

```
Asp Val Ser Gln Glu Pro Asp Val Lys Phe Asn Trp Tyr Val
            155                 160                 165

Asn Gly Ala Glu Val His His Ala Gln Thr Lys Pro Arg Glu Thr
            170                 175                 180

Gln Tyr Asn Ser Thr Tyr Arg Val Val Ser Val Leu Thr Val Thr
            185                 190                 195

His Gln Asp Trp Leu Asn Gly Lys Glu Tyr Thr Cys Lys Val Ser
            200                 205                 210

Asn Lys Ala Leu Pro Ala Pro Arg Gln Lys Thr Val Ser Lys Thr
            215                 220                 225

Lys Gly Gln Pro Arg Glu Pro Gln Val Tyr Thr Leu Pro Pro Pro
            230                 235                 240

Arg Glu Glu Leu Thr Lys Asn Gln Val Ser Leu Thr Cys Leu Ile
            245                 250                 255

Lys Gly Phe Tyr Pro Ser Asp Ile Val Val Glu Trp Ala Ser Asn
            260                 265                 270

Gly Gln Pro Glu Asn Thr Tyr Lys Thr Thr Pro Pro Val Leu Asp
            275                 280                 285

Ser Asp Gly Ser Tyr Phe Leu Tyr Ser Lys Leu Thr Val Asp Lys
            290                 295                 300

Ser Arg Trp Gln Gln Gly Asn Val Phe Ser Cys Ser Val Met His
            305                 310                 315

Glu Ala Leu His Asn His Tyr Thr Gln Lys Ser Leu Ser
            320                 325

<210> SEQ ID NO 13
<211> LENGTH: 328
<212> TYPE: PRT
<213> ORGANISM: Artificial sequence
<220> FEATURE:
<223> OTHER INFORMATION: sequence is synthesized

<400> SEQUENCE: 13

Ala Ser Thr Lys Gly Pro Ser Val Phe Pro Leu Ala Pro Ser Ser
  1               5                  10                  15

Arg Ser Thr Ser Glu Ser Thr Ala Ala Leu Gly Cys Leu Val Lys
            20                  25                  30

Asp Tyr Phe Pro Glu Pro Val Thr Val Ser Trp Asn Ser Gly Ser
            35                  40                  45

Leu Thr Ser Gly Val His Thr Phe Pro Ala Val Leu Gln Ser Ser
            50                  55                  60

Gly Leu Tyr Ser Leu Ser Ser Val Val Thr Val Pro Ser Ser Ser
            65                  70                  75

Leu Gly Thr Gln Thr Tyr Val Cys Asn Val Asn His Lys Pro Ser
            80                  85                  90

Asn Thr Lys Val Asp Lys Arg Val Glu Ile Lys Thr Cys Gly Gly
            95                  100                 105

Gly Ser Lys Pro Pro Thr Cys Pro Pro Cys Pro Ala Pro Glu Leu
            110                 115                 120

Leu Gly Gly Pro Ser Val Phe Leu Phe Pro Pro Lys Pro Lys Asp
            125                 130                 135

Thr Leu Met Ile Ser Arg Thr Pro Glu Val Thr Cys Val Val Val
            140                 145                 150

Asp Val Ser Gln Glu Glu Pro Asp Val Lys Phe Asn Trp Tyr Val
            155                 160                 165
```

```
Asp Gly Val Glu Val His Asn Ala Gln Thr Lys Pro Arg Glu Glu
            170                 175                 180

Gln Phe Asn Ser Thr Tyr Arg Val Val Ser Val Leu Thr Val
            185                 190                 195

His Gln Asp Trp Leu Asn Gly Lys Glu Tyr Thr Cys Lys Val Ser
            200                 205                 210

Asn Lys Ala Leu Pro Ala Pro Arg Gln Lys Thr Val Ser Lys Thr
            215                 220                 225

Lys Gly Gln Pro Arg Glu Pro Gln Val Tyr Thr Leu Pro Pro Pro
            230                 235                 240

Arg Glu Glu Leu Thr Lys Asn Gln Val Ser Leu Thr Cys Leu Ile
            245                 250                 255

Lys Gly Phe Tyr Pro Ser Asp Ile Val Val Glu Trp Ala Ser Asn
            260                 265                 270

Gly Gln Pro Glu Asn Thr Tyr Lys Thr Thr Pro Pro Val Leu Asp
            275                 280                 285

Ser Asp Gly Ser Tyr Phe Leu Tyr Ser Lys Leu Thr Val Asp Lys
            290                 295                 300

Ser Arg Trp Gln Gln Gly Asn Val Phe Ser Cys Ser Val Met His
            305                 310                 315

Glu Ala Leu His Asn His Tyr Thr Gln Lys Ser Leu Ser
            320                 325

<210> SEQ ID NO 14
<211> LENGTH: 321
<212> TYPE: PRT
<213> ORGANISM: Artificial sequence
<220> FEATURE:
<223> OTHER INFORMATION: sequence is synthesized

<400> SEQUENCE: 14

Ala Ser Thr Lys Gly Pro Ser Val Phe Pro Leu Ala Pro Ser Ser
  1               5                  10                  15

Arg Ser Thr Ser Gln Ser Thr Ala Ala Leu Gly Cys Leu Val Lys
                 20                  25                  30

Asp Tyr Phe Pro Glu Pro Val Thr Val Ser Trp Asn Ser Gly Ala
                 35                  40                  45

Leu Thr Ser Gly Val His Thr Phe Pro Ala Val Leu Gln Ser Ser
                 50                  55                  60

Gly Leu Tyr Ser Leu Ser Ser Val Val Thr Val Pro Ser Ser Ser
                 65                  70                  75

Leu Gly Thr Gln Thr Tyr Val Cys Asn Val Val His Glu Pro Ser
                 80                  85                  90

Asn Thr Lys Val Asp Lys Thr Val Gly Leu Pro Cys Arg Ser Thr
                 95                  100                 105

Cys Cys Pro Cys Ala Pro Glu Leu Leu Gly Gly Pro Ser Val Phe
                 110                 115                 120

Leu Phe Pro Pro Lys Pro Lys Asp Thr Leu Met Ile Ser Arg Thr
                 125                 130                 135

Pro Glu Val Thr Cys Val Val Val Asp Val Ser Gln Glu Asp Pro
                 140                 145                 150

Asp Val Lys Phe Asn Trp Tyr Val Asn Gly Ala Glu Val His His
                 155                 160                 165

Ala Gln Thr Lys Pro Arg Glu Thr Gln Tyr Asn Ser Thr Tyr Arg
                 170                 175                 180

Val Val Ser Val Leu Thr Val Thr His Gln Asp Trp Leu Asn Gly
```

```
                185                 190                 195

Lys Glu Tyr Thr Cys Lys Val Ser Asn Lys Ala Leu Pro Ala Pro
                200                 205                 210

Ile Gln Lys Thr Val Ser Lys Asp Lys Gly Gln Pro Arg Glu Pro
                215                 220                 225

Gln Val Tyr Thr Leu Pro Pro Ser Arg Glu Glu Leu Thr Lys Asn
                230                 235                 240

Gln Val Ser Leu Thr Cys Leu Ile Lys Gly Phe Tyr Pro Ser Asp
                245                 250                 255

Ile Val Val Glu Trp Glu Ser Ser Gly Gln Pro Glu Asn Thr Tyr
                260                 265                 270

Lys Thr Thr Pro Pro Val Leu Asp Ser Asp Gly Ser Tyr Phe Leu
                275                 280                 285

Tyr Ser Lys Leu Thr Val Asp Lys Ser Arg Trp Gln Gln Gly Asn
                290                 295                 300

Val Phe Ser Cys Ser Val Met His Glu Ala Leu His Asn His Tyr
                305                 310                 315

Thr Gln Lys Ser Leu Ser
                320

<210> SEQ ID NO 15
<211> LENGTH: 321
<212> TYPE: PRT
<213> ORGANISM: Artificial sequence
<220> FEATURE:
<223> OTHER INFORMATION: sequence is synthesized

<400> SEQUENCE: 15

Ala Ser Thr Lys Gly Pro Ser Val Phe Pro Leu Ala Pro Ser Ser
  1               5                  10                  15

Arg Ser Thr Ser Gln Ser Thr Ala Ala Leu Gly Cys Leu Val Lys
                 20                  25                  30

Asp Tyr Phe Pro Glu Pro Val Thr Val Ser Trp Asn Ser Gly Ala
                 35                  40                  45

Leu Thr Ser Gly Val His Thr Phe Pro Ala Val Leu Gln Ser Ser
                 50                  55                  60

Gly Leu Tyr Ser Leu Ser Ser Val Val Thr Val Pro Ser Ser Ser
                 65                  70                  75

Leu Gly Thr Gln Thr Tyr Val Cys Asn Val Val His Glu Pro Ser
                 80                  85                  90

Asn Thr Lys Val Asp Lys Thr Val Gly Leu Pro Cys Arg Ser Thr
                 95                 100                 105

Cys Cys Pro Cys Ala Pro Glu Leu Leu Gly Gly Pro Ser Val Phe
                110                 115                 120

Leu Phe Pro Pro Lys Pro Lys Asp Thr Leu Met Ile Ser Arg Thr
                125                 130                 135

Pro Glu Val Thr Cys Val Val Val Asp Val Ser Gln Glu Glu Pro
                140                 145                 150

Asp Val Lys Phe Asn Trp Tyr Val Asp Gly Val Glu Val His Asn
                155                 160                 165

Ala Gln Thr Lys Pro Arg Glu Glu Gln Phe Asn Ser Thr Tyr Arg
                170                 175                 180

Val Val Ser Val Leu Thr Val Thr His Gln Asp Trp Leu Asn Gly
                185                 190                 195

Lys Glu Tyr Thr Cys Lys Val Ser Asn Lys Ala Leu Pro Ala Pro
                200                 205                 210
```

Ile Gln Lys Thr Val Ser Lys Asp Lys Gly Gln Pro Arg Glu Pro
                215                 220                 225

Gln Val Tyr Thr Leu Pro Pro Ser Arg Glu Glu Leu Thr Lys Asn
            230                 235                 240

Gln Val Ser Leu Thr Cys Leu Ile Lys Gly Phe Tyr Pro Ser Asp
            245                 250                 255

Ile Val Val Glu Trp Glu Ser Ser Gly Gln Pro Glu Asn Thr Tyr
            260                 265                 270

Lys Thr Thr Pro Pro Val Leu Asp Ser Asp Gly Ser Tyr Phe Leu
            275                 280                 285

Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr
            305                 310                 315

Thr Gln Lys Ser Leu Ser
            320

<210> SEQ ID NO 16
<211> LENGTH: 320
<212> TYPE: PRT
<213> ORGANISM: Artificial sequence
<220> FEATURE:
<223> OTHER INFORMATION: sequence is synthesized

<400> SEQUENCE: 16

Ala Ser Thr Lys Gly Pro Ser Val Phe Pro Leu Ala Pro Ser Ser
  1               5                  10                  15

Arg Ser Thr Ser Glu Ser Thr Ala Ala Leu Gly Cys Leu Val Lys
             20                  25                  30

Asp Tyr Phe Pro Glu Pro Val Thr Val Ser Trp Asn Ser Gly Ala
             35                  40                  45

Leu Thr Ser Gly Val His Thr Phe Pro Ala Val Leu Gln Ser Ser
             50                  55                  60

Gly Leu Tyr Ser Leu Ser Ser Val Val Thr Val Pro Ser Ser Ser
             65                  70                  75

Leu Gly Thr Gln Thr Tyr Val Cys Asn Val Val His Glu Pro Ser
             80                  85                  90

Asn Thr Lys Val Asp Lys Arg Val Glu Phe Thr Pro Pro Cys Pro
             95                 100                 105

Pro Cys Pro Ala Pro Glu Leu Leu Gly Gly Pro Ser Val Phe Leu
            110                 115                 120

Phe Pro Pro Lys Pro Lys Asp Thr Leu Met Ile Ser Arg Thr Pro
            125                 130                 135

Glu Val Thr Cys Val Val Val Asp Val Ser Gln Glu Asp Pro Asp
            140                 145                 150

Val Lys Phe Asn Trp Tyr Val Asn Gly Ala Glu Val His Asn Ala
            155                 160                 165

Gln Thr Lys Pro Arg Glu Glu Gln Phe Asn Ser Thr Tyr Arg Val
            170                 175                 180

Val Ser Val Leu Thr Val Thr His Gln Asp Trp Leu Asn Gly Lys
            185                 190                 195

Glu Tyr Thr Cys Lys Val Ser Asn Lys Ala Leu Pro Ala Pro Arg
            200                 205                 210

Gln Lys Thr Val Ser Lys Thr Lys Gly Gln Pro Arg Glu Pro Gln
            215                 220                 225

```
Val Tyr Thr Leu Pro Pro Arg Glu Glu Leu Thr Lys Asn Gln
            230                 235                 240

Val Ser Leu Thr Cys Leu Ile Lys Gly Phe Tyr Pro Ser Asp Ile
            245                 250                 255

Val Val Glu Trp Ala Ser Asn Gly Gln Pro Glu Asn Thr Tyr Lys
            260                 265                 270

Thr Thr Pro Pro Val Leu Asp Ser Asp Gly Ser Tyr Phe Leu Tyr
            275                 280                 285

Ser Lys Leu Thr Val Asp Lys Ser Arg Trp Gln Gln Gly Asn Thr
            290                 295                 300

Phe Ser Cys Ser Val Met His Glu Ala Leu His Asn His Tyr Thr
            305                 310                 315

Gln Lys Ser Leu Ser
            320

<210> SEQ ID NO 17
<211> LENGTH: 450
<212> TYPE: PRT
<213> ORGANISM: Artificial sequence
<220> FEATURE:
<223> OTHER INFORMATION: sequence is synthesized

<400> SEQUENCE: 17

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Asn Ile Lys
             20                  25                  30

Asp Thr Tyr Ile His Trp Val Arg Gln Ala Pro Gly Lys Gly Leu
             35                  40                  45

Glu Trp Val Ala Arg Ile Tyr Pro Thr Asn Gly Tyr Thr Arg Tyr
             50                  55                  60

Ala Asp Ser Val Lys Gly Arg Phe Thr Ile Ser Ala Asp Thr Ser
             65                  70                  75

Lys Asn Thr Ala Tyr Leu Gln Met Asn Ser Leu Arg Ala Glu Asp
             80                  85                  90

Thr Ala Val Tyr Tyr Cys Ser Arg Trp Gly Gly Asp Gly Phe Tyr
             95                 100                 105

Ala Met Asp Tyr Trp Gly Gln Gly Thr Leu Val Thr Val Ser Ser
            110                 115                 120

Ala Ser Thr Lys Gly Pro Ser Val Phe Pro Leu Ala Pro Ser Ser
            125                 130                 135

Lys Ser Thr Ser Gly Gly Thr Ala Ala Leu Gly Cys Leu Val Lys
            140                 145                 150

Asp Tyr Phe Pro Glu Pro Val Thr Val Ser Trp Asn Ser Gly Ala
            155                 160                 165

Leu Thr Ser Gly Val His Thr Phe Pro Ala Val Leu Gln Ser Ser
            170                 175                 180

Gly Leu Tyr Ser Leu Ser Ser Val Val Thr Val Pro Ser Ser Ser
            185                 190                 195

Leu Gly Thr Gln Thr Tyr Ile Cys Asn Val Asn His Lys Pro Ser
            200                 205                 210

Asn Thr Lys Val Asp Lys Lys Val Glu Pro Lys Ser Cys Asp Lys
            215                 220                 225

Thr His Thr Cys Pro Pro Cys Pro Ala Pro Glu Leu Leu Gly Gly
            230                 235                 240

Pro Ser Val Phe Leu Phe Pro Pro Lys Pro Lys Asp Thr Leu Met
```

```
                        245                 250                 255
Ile Ser Arg Thr Pro Glu Val Thr Cys Val Val Asp Val Ser
            260                 265                 270

His Glu Asp Pro Glu Val Lys Phe Asn Trp Tyr Val Asp Gly Val
                275                 280                 285

Glu Val His Asn Ala Lys Thr Lys Pro Arg Glu Glu Gln Tyr Asn
            290                 295                 300

Ser Thr Tyr Arg Val Val Ser Val Leu Thr Val Leu His Gln Asp
            305                 310                 315

Trp Leu Asn Gly Lys Glu Tyr Lys Cys Lys Val Ser Asn Lys Ala
            320                 325                 330

Leu Pro Ala Pro Ile Glu Lys Thr Ile Ser Lys Ala Lys Gly Gln
            335                 340                 345

Pro Arg Glu Pro Gln Val Tyr Thr Leu Pro Pro Ser Arg Glu Glu
            350                 355                 360

Met Thr Lys Asn Gln Val Ser Leu Thr Cys Leu Val Lys Gly Phe
            365                 370                 375

Tyr Pro Ser Asp Ile Ala Val Glu Trp Glu Ser Asn Gly Gln Pro
            380                 385                 390

Glu Asn Asn Tyr Lys Thr Thr Pro Pro Val Leu Asp Ser Asp Gly
            395                 400                 405

Ser Phe Phe Leu Tyr Ser Lys Leu Thr Val Asp Lys Ser Arg Trp
            410                 415                 420

Gln Gln Gly Asn Val Phe Ser Cys Ser Val Met His Glu Ala Leu
            425                 430                 435

His Asn His Tyr Thr Gln Lys Ser Leu Ser Leu Ser Pro Gly Lys
            440                 445                 450

<210> SEQ ID NO 18
<211> LENGTH: 214
<212> TYPE: PRT
<213> ORGANISM: Artificial sequence
<220> FEATURE:
<223> OTHER INFORMATION: sequence is synthesized

<400> SEQUENCE: 18

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Asp Val Asn
                20                  25                  30

Thr Ala Val Ala Trp Tyr Gln Gln Lys Pro Gly Lys Ala Pro Lys
            35                  40                  45

Leu Leu Ile Tyr Ser Ala Ser Phe Leu Tyr Ser Gly Val Pro Ser
        50                  55                  60

Arg Phe Ser Gly Ser Arg Ser Gly Thr Asp Phe Thr Leu Thr Ile
    65                  70                  75

Ser Ser Leu Gln Pro Glu Asp Phe Ala Thr Tyr Tyr Cys Gln Gln
            80                  85                  90

His Tyr Thr Thr Pro Pro Thr Phe Gly Gln Gly Thr Lys Val Glu
                95                  100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150
```

```
Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
        185                 190                 195

Val Thr His Gln Gly Leu Ser Ser Pro Val Thr Lys Ser Phe Asn
    200                 205                 210

Arg Gly Glu Cys
```

<210> SEQ ID NO 19
<211> LENGTH: 213
<212> TYPE: PRT
<213> ORGANISM: Artificial sequence
<220> FEATURE:
<223> OTHER INFORMATION: sequence is synthesized

<400> SEQUENCE: 19

```
Asp Ile Gln Met Thr Gln Ser Pro Ser Ser Leu Ser Ala Ser Val
  1               5                  10                  15

Gly Asp Arg Val Thr Ile Thr Cys Arg Ala Ser Ser Ser Val Ser
                 20                  25                  30

Tyr Met His Trp Tyr Gln Gln Lys Pro Gly Lys Ala Pro Lys Pro
             35                  40                  45

Leu Ile Tyr Ala Pro Ser Asn Leu Ala Ser Gly Val Pro Ser Arg
         50                  55                  60

Phe Ser Gly Ser Gly Ser Gly Thr Asp Phe Thr Leu Thr Ile Ser
     65                  70                  75

Ser Leu Gln Pro Glu Asp Phe Ala Thr Tyr Tyr Cys Gln Gln Trp
 80                  85                  90

Ser Phe Asn Pro Pro Thr Phe Gly Gln Gly Thr Lys Val Glu Ile
             95                 100                 105

Lys Arg Thr Val Ala Ala Pro Ser Val Phe Ile Phe Pro Pro Ser
            110                 115                 120

Asp Glu Gln Leu Lys Ser Gly Thr Ala Ser Val Val Cys Leu Leu
        125                 130                 135

Asn Asn Phe Tyr Pro Arg Glu Ala Lys Val Gln Trp Lys Val Asp
    140                 145                 150

Asn Ala Leu Gln Ser Gly Asn Ser Gln Glu Ser Val Thr Glu Gln
                155                 160                 165

Asp Ser Lys Asp Ser Thr Tyr Ser Leu Ser Ser Thr Leu Thr Leu
            170                 175                 180

Ser Lys Ala Asp Tyr Glu Lys His Lys Val Tyr Ala Cys Glu Val
        185                 190                 195

Thr His Gln Gly Leu Ser Ser Pro Val Thr Lys Ser Phe Asn Arg
    200                 205                 210

Gly Glu Cys
```

<210> SEQ ID NO 20
<211> LENGTH: 448
<212> TYPE: PRT
<213> ORGANISM: Artificial sequence
<220> FEATURE:
<223> OTHER INFORMATION: sequence is synthesized

<400> SEQUENCE: 20

```
Glu Val Gln Leu Val Glu Ser Gly Gly Gly Leu Val Gln Pro Gly
```

-continued

```
              1               5              10              15
        Gly Ser Leu Arg Leu Ser Cys Ala Ala Ser Gly Phe Thr Phe Thr
                             20                  25                  30
        Asp Tyr Thr Met Asp Trp Val Arg Gln Ala Pro Gly Lys Gly Leu
                             35                  40                  45
        Glu Trp Val Ala Asp Val Asn Pro Asn Ser Gly Gly Ser Ile Tyr
                             50                  55                  60
        Asn Gln Arg Phe Lys Gly Arg Phe Thr Leu Ser Val Asp Arg Ser
                             65                  70                  75
        Lys Asn Thr Leu Tyr Leu Gln Met Asn Ser Leu Arg Ala Glu Asp
                             80                  85                  90
        Thr Ala Val Tyr Tyr Cys Ala Arg Asn Leu Gly Pro Ser Phe Tyr
                             95                 100                 105
        Phe Asp Tyr Trp Gly Gln Gly Thr Leu Val Thr Val Ser Ser Ala
                            110                 115                 120
        Ser Thr Lys Gly Pro Ser Val Phe Pro Leu Ala Pro Ser Ser Lys
                            125                 130                 135
        Ser Thr Ser Gly Gly Thr Ala Ala Leu Gly Cys Leu Val Lys Asp
                            140                 145                 150
        Tyr Phe Pro Glu Pro Val Thr Val Ser Trp Asn Ser Gly Ala Leu
                            155                 160                 165
        Thr Ser Gly Val His Thr Phe Pro Ala Val Leu Gln Ser Ser Gly
                            170                 175                 180
        Leu Tyr Ser Leu Ser Ser Val Val Thr Val Pro Ser Ser Ser Leu
                            185                 190                 195
        Gly Thr Gln Thr Tyr Ile Cys Asn Val Asn His Lys Pro Ser Asn
                            200                 205                 210
        Thr Lys Val Asp Lys Lys Val Glu Pro Lys Ser Cys Asp Lys Thr
                            215                 220                 225
        His Thr Cys Pro Pro Cys Pro Ala Pro Glu Leu Leu Gly Gly Pro
                            230                 235                 240
        Ser Val Phe Leu Phe Pro Pro Lys Pro Lys Asp Thr Leu Met Ile
                            245                 250                 255
        Ser Arg Thr Pro Glu Val Thr Cys Val Val Val Asp Val Ser His
                            260                 265                 270
        Glu Asp Pro Glu Val Lys Phe Asn Trp Tyr Val Asp Gly Val Glu
                            275                 280                 285
        Val His Asn Ala Lys Thr Lys Pro Arg Glu Glu Gln Tyr Asn Ser
                            290                 295                 300
        Thr Tyr Arg Val Val Ser Val Leu Thr Val Leu His Gln Asp Trp
                            305                 310                 315
        Leu Asn Gly Lys Glu Tyr Lys Cys Lys Val Ser Asn Lys Ala Leu
                            320                 325                 330
        Pro Ala Pro Ile Glu Lys Thr Ile Ser Lys Ala Lys Gly Gln Pro
                            335                 340                 345
        Arg Glu Pro Gln Val Tyr Thr Leu Pro Pro Ser Arg Glu Glu Met
                            350                 355                 360
        Thr Lys Asn Gln Val Ser Leu Thr Cys Leu Val Lys Gly Phe Tyr
                            365                 370                 375
        Pro Ser Asp Ile Ala Val Glu Trp Glu Ser Asn Gly Gln Pro Glu
                            380                 385                 390
        Asn Asn Tyr Lys Thr Thr Pro Pro Val Leu Asp Ser Asp Gly Ser
                            395                 400                 405
```

-continued

```
Phe Phe Leu Tyr Ser Lys Leu Thr Val Asp Lys Ser Arg Trp Gln
            410                 415                 420

Gln Gly Asn Val Phe Ser Cys Ser Val Met His Glu Ala Leu His
            425                 430                 435

Asn His Tyr Thr Gln Lys Ser Leu Ser Leu Ser Pro Gly
            440                 445

<210> SEQ ID NO 21
<211> LENGTH: 214
<212> TYPE: PRT
<213> ORGANISM: Artificial sequence
<220> FEATURE:
<223> OTHER INFORMATION: sequence is synthesized

<400> SEQUENCE: 21

Asp Ile Gln Met Thr Gln Ser Pro Ser Ser Leu Ser Ala Ser Val
 1               5                  10                  15

Gly Asp Arg Val Thr Ile Thr Cys Lys Ala Ser Gln Asp Val Ser
                20                  25                  30

Ile Gly Val Ala Trp Tyr Gln Gln Lys Pro Gly Lys Ala Pro Lys
                35                  40                  45

Leu Leu Ile Tyr Ser Ala Ser Tyr Arg Tyr Thr Gly Val Pro Ser
                50                  55                  60

Arg Phe Ser Gly Ser Gly Ser Gly Thr Asp Phe Thr Leu Thr Ile
                65                  70                  75

Ser Ser Leu Gln Pro Glu Asp Phe Ala Thr Tyr Tyr Cys Gln Gln
                80                  85                  90

Tyr Tyr Ile Tyr Pro Tyr Thr Phe Gly Gln Gly Thr Lys Val Glu
                95                  100                 105

Ile Lys Arg Thr Val Ala Ala Pro Ser Val Phe Ile Phe Pro Pro
                110                 115                 120

Ser Asp Glu Gln Leu Lys Ser Gly Thr Ala Ser Val Val Cys Leu
                125                 130                 135

Leu Asn Asn Phe Tyr Pro Arg Glu Ala Lys Val Gln Trp Lys Val
                140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
                185                 190                 195

Val Thr His Gln Gly Leu Ser Ser Pro Val Thr Lys Ser Phe Asn
                200                 205                 210

Arg Gly Glu Cys

<210> SEQ ID NO 22
<211> LENGTH: 448
<212> TYPE: PRT
<213> ORGANISM: Artificial sequence
<220> FEATURE:
<223> OTHER INFORMATION: sequence is synthesized

<400> SEQUENCE: 22

Glu Val Gln Leu Val Glu Ser Gly Gly Gly Leu Val Gln Pro Gly
 1               5                  10                  15

Gly Ser Leu Arg Leu Ser Cys Ala Ala Ser Gly Phe Thr Phe Ser
                20                  25                  30

Asp Ser Trp Ile His Trp Val Arg Gln Ala Pro Gly Lys Gly Leu
```

```
                    35                  40                  45
Glu Trp Val Ala Trp Ile Ser Pro Tyr Gly Gly Ser Thr Tyr Tyr
                50                  55                  60
Ala Asp Ser Val Lys Gly Arg Phe Thr Ile Ser Ala Asp Thr Ser
                65                  70                  75
Lys Asn Thr Ala Tyr Leu Gln Met Asn Ser Leu Arg Ala Glu Asp
                80                  85                  90
Thr Ala Val Tyr Tyr Cys Ala Arg Arg His Trp Pro Gly Gly Phe
                95                 100                 105
Asp Tyr Trp Gly Gln Gly Thr Leu Val Thr Val Ser Ser Ala Ser
               110                 115                 120
Thr Lys Gly Pro Ser Val Phe Pro Leu Ala Pro Ser Ser Lys Ser
               125                 130                 135
Thr Ser Gly Gly Thr Ala Ala Leu Gly Cys Leu Val Lys Asp Tyr
               140                 145                 150
Phe Pro Glu Pro Val Thr Val Ser Trp Asn Ser Gly Ala Leu Thr
               155                 160                 165
Ser Gly Val His Thr Phe Pro Ala Val Leu Gln Ser Ser Gly Leu
               170                 175                 180
Tyr Ser Leu Ser Ser Val Val Thr Val Pro Ser Ser Ser Leu Gly
               185                 190                 195
Thr Gln Thr Tyr Ile Cys Asn Val Asn His Lys Pro Ser Asn Thr
               200                 205                 210
Lys Val Asp Lys Lys Val Glu Pro Lys Ser Cys Asp Lys Thr His
               215                 220                 225
Thr Cys Pro Pro Cys Pro Ala Pro Glu Leu Leu Gly Gly Pro Ser
               230                 235                 240
Val Phe Leu Phe Pro Pro Lys Pro Lys Asp Thr Leu Met Ile Ser
               245                 250                 255
Arg Thr Pro Glu Val Thr Cys Val Val Val Asp Val Ser His Glu
               260                 265                 270
Asp Pro Glu Val Lys Phe Asn Trp Tyr Val Asp Gly Val Glu Val
               275                 280                 285
His Asn Ala Lys Thr Lys Pro Arg Glu Glu Gln Tyr Ala Ser Thr
               290                 295                 300
Tyr Arg Val Val Ser Val Leu Thr Val Leu His Gln Asp Trp Leu
               305                 310                 315
Asn Gly Lys Glu Tyr Lys Cys Lys Val Ser Asn Lys Ala Leu Pro
               320                 325                 330
Ala Pro Ile Glu Lys Thr Ile Ser Lys Ala Lys Gly Gln Pro Arg
               335                 340                 345
Glu Pro Gln Val Tyr Thr Leu Pro Pro Ser Arg Glu Glu Met Thr
               350                 355                 360
Lys Asn Gln Val Ser Leu Thr Cys Leu Val Lys Gly Phe Tyr Pro
               365                 370                 375
Ser Asp Ile Ala Val Glu Trp Glu Ser Asn Gly Gln Pro Glu Asn
               380                 385                 390
Asn Tyr Lys Thr Thr Pro Pro Val Leu Asp Ser Asp Gly Ser Phe
               395                 400                 405
Phe Leu Tyr Ser Lys Leu Thr Val Asp Lys Ser Arg Trp Gln Gln
               410                 415                 420
Gly Asn Val Phe Ser Cys Ser Val Met His Glu Ala Leu His Asn
               425                 430                 435
```

His Tyr Thr Gln Lys Ser Leu Ser Leu Ser Pro Gly Lys
            440                 445

<210> SEQ ID NO 23
<211> LENGTH: 214
<212> TYPE: PRT
<213> ORGANISM: Artificial sequence
<220> FEATURE:
<223> OTHER INFORMATION: sequence is synthesized

<400> SEQUENCE: 23

Asp Ile Gln Met Thr Gln Ser Pro Ser Ser Leu Ser Ala Ser Val
  1               5                  10                  15

Gly Asp Arg Val Thr Ile Thr Cys Arg Ala Ser Gln Asp Val Ser
                 20                  25                  30

Thr Ala Val Ala Trp Tyr Gln Gln Lys Pro Gly Lys Ala Pro Lys
             35                  40                  45

Leu Leu Ile Tyr Ser Ala Ser Phe Leu Tyr Ser Gly Val Pro Ser
         50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
             80                  85                  90

Tyr Leu Tyr His Pro Ala Thr Phe Gly Gln Gly Thr Lys Val Glu
             95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
            125                 130                 135

Leu Asn Asn Phe Tyr Pro Arg Glu Ala Lys Val Gln Trp Lys Val
            140                 145                 150

Asp Asn Ala Leu Gln Ser Gly Asn Ser Gln Glu Ser Val Thr Glu
            155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
            200                 205                 210

Arg Gly Glu Cys

<210> SEQ ID NO 24
<211> LENGTH: 453
<212> TYPE: PRT
<213> ORGANISM: Artificial sequence
<220> FEATURE:
<223> OTHER INFORMATION: sequence is synthesized

<400> SEQUENCE: 24

Glu Val Gln Leu Val Glu Ser Gly Gly Gly Leu Val Gln Pro Gly
  1               5                  10                  15

Gly Ser Leu Arg Leu Ser Cys Ala Ala Ser Gly Phe Thr Phe Ser
                 20                  25                  30

Ser Tyr Ala Met Ser Trp Val Arg Gln Ala Pro Gly Lys Gly Leu
             35                  40                  45

Glu Trp Val Ser Gln Ile Ser Pro Ala Gly Gly Tyr Thr Asn Tyr
         50                  55                  60

Ala Asp Ser Val Lys Gly Arg Phe Thr Ile Ser Ala Asp Thr Ser

```
                    65                  70                  75
Lys Asn Thr Ala Tyr Leu Gln Met Asn Ser Leu Arg Ala Glu Asp
                80                  85                  90
Thr Ala Val Tyr Tyr Cys Ala Arg Gly Glu Leu Pro Tyr Tyr Arg
                95                 100                 105
Met Ser Lys Val Met Asp Val Trp Gly Gln Gly Thr Leu Val Thr
               110                 115                 120
Val Ser Ser Ala Ser Thr Lys Gly Pro Ser Val Phe Pro Leu Ala
               125                 130                 135
Pro Ser Ser Lys Ser Thr Ser Gly Gly Thr Ala Ala Leu Gly Cys
               140                 145                 150
Leu Val Lys Asp Tyr Phe Pro Glu Pro Val Thr Val Ser Trp Asn
               155                 160                 165
Ser Gly Ala Leu Thr Ser Gly Val His Thr Phe Pro Ala Val Leu
               170                 175                 180
Gln Ser Ser Gly Leu Tyr Ser Leu Ser Ser Val Val Thr Val Pro
               185                 190                 195
Ser Ser Ser Leu Gly Thr Gln Thr Tyr Ile Cys Asn Val Asn His
               200                 205                 210
Lys Pro Ser Asn Thr Lys Val Asp Lys Lys Val Glu Pro Lys Ser
               215                 220                 225
Cys Asp Lys Thr His Thr Cys Pro Pro Cys Pro Ala Pro Glu Leu
               230                 235                 240
Leu Gly Gly Pro Ser Val Phe Leu Phe Pro Pro Lys Pro Lys Asp
               245                 250                 255
Thr Leu Met Ile Ser Arg Thr Pro Glu Val Thr Cys Val Val Val
               260                 265                 270
Asp Val Ser His Glu Asp Pro Glu Val Lys Phe Asn Trp Tyr Val
               275                 280                 285
Asp Gly Val Glu Val His Asn Ala Lys Thr Lys Pro Arg Glu Glu
               290                 295                 300
Gln Tyr Asn Ser Thr Tyr Arg Val Val Ser Val Leu Thr Val Leu
               305                 310                 315
His Gln Asp Trp Leu Asn Gly Lys Glu Tyr Lys Cys Lys Val Ser
               320                 325                 330
Asn Lys Ala Leu Pro Ala Pro Ile Glu Lys Thr Ile Ser Lys Ala
               335                 340                 345
Lys Gly Gln Pro Arg Glu Pro Gln Val Tyr Thr Leu Pro Pro Ser
               350                 355                 360
Arg Glu Glu Met Thr Lys Asn Gln Val Ser Leu Thr Cys Leu Val
               365                 370                 375
Lys Gly Phe Tyr Pro Ser Asp Ile Ala Val Glu Trp Glu Ser Asn
               380                 385                 390
Gly Gln Pro Glu Asn Asn Tyr Lys Thr Thr Pro Pro Val Leu Asp
               395                 400                 405
Ser Asp Gly Ser Phe Phe Leu Tyr Ser Lys Leu Thr Val Asp Lys
               410                 415                 420
Ser Arg Trp Gln Gln Gly Asn Val Phe Ser Cys Ser Val Met His
               425                 430                 435
Glu Ala Leu His Asn His Tyr Thr Gln Lys Ser Leu Ser Leu Ser
               440                 445                 450
Pro Gly Lys
```

```
<210> SEQ ID NO 25
<211> LENGTH: 214
<212> TYPE: PRT
<213> ORGANISM: Artificial sequence
<220> FEATURE:
<223> OTHER INFORMATION: sequence is synthesized

<400> SEQUENCE: 25

Asp Ile Gln Met Thr Gln Ser Pro Ser Ser Leu Ser Ala Ser Val
 1               5                  10                  15

Gly Asp Arg Val Thr Ile Thr Cys Arg Ala Ser Gln Tyr Phe Ser
                20                  25                  30

Ser Tyr Leu Ala Trp Tyr Gln Gln Lys Pro Gly Lys Ala Pro Lys
            35                  40                  45

Leu Leu Ile Tyr Gly Ala Ser Ser Arg Ala Ser Gly Val Pro Ser
        50                  55                  60

Arg Phe Ser Gly Ser Gly Ser Gly Thr Asp Phe Thr Leu Thr Ile
 65                  70                  75

Ser Ser Leu Gln Pro Glu Asp Phe Ala Thr Tyr Tyr Cys Gln Gln
                80                  85                  90

Tyr Leu Gly Ser Pro Pro Thr Phe Gly Gln Gly Thr Lys Val Glu
                95                 100                 105

Ile Lys Arg Thr Val Ala Ala Pro Ser Val Phe Ile Phe Pro Pro
            110                 115                 120

Ser Asp Glu Gln Leu Lys Ser Gly Thr Ala Ser Val Val Cys Leu
        125                 130                 135

Leu Asn Asn Phe Tyr Pro Arg Glu Ala Lys Val Gln Trp Lys Val
    140                 145                 150

Asp Asn Ala Leu Gln Ser Gly Asn Ser Gln Glu Ser Val Thr Glu
155                 160                 165

Gln Asp Ser Lys Asp Ser Thr Tyr Ser Leu Ser Ser Thr Leu Thr
                170                 175                 180

Leu Ser Lys Ala Asp Tyr Glu Lys His Lys Val Tyr Ala Cys Glu
            185                 190                 195

Val Thr His Gln Gly Leu Ser Ser Pro Val Thr Lys Ser Phe Asn
        200                 205                 210

Arg Gly Glu Cys

<210> SEQ ID NO 26
<211> LENGTH: 446
<212> TYPE: PRT
<213> ORGANISM: Artificial sequence
<220> FEATURE:
<223> OTHER INFORMATION: sequence is synthesized

<400> SEQUENCE: 26

Glu Val Gln Leu Val Glu Ser Gly Gly Gly Leu Val Gln Pro Gly
 1               5                  10                  15

Gly Ser Leu Arg Leu Ser Cys Ala Ala Ser Gly Tyr Ser Ile Thr
                20                  25                  30

Asn Asp Tyr Ala Trp Asn Trp Val Arg Gln Ala Pro Gly Lys Gly
            35                  40                  45

Leu Glu Trp Val Gly Tyr Ile Ser Tyr Ser Gly Tyr Thr Thr Tyr
        50                  55                  60

Asn Pro Ser Leu Lys Ser Arg Phe Thr Ile Ser Arg Asp Thr Ser
 65                  70                  75

Lys Asn Thr Leu Tyr Leu Gln Met Asn Ser Leu Arg Ala Glu Asp
                80                  85                  90
```

Thr Ala Val Tyr Tyr Cys Ala Arg Trp Thr Ser Gly Leu Asp Tyr
                95                 100                 105

Trp Gly Gln Gly Thr Leu Val Thr Val Ser Ser Cys Ser Thr Lys
           110                 115                 120

Gly Pro Ser Val Phe Pro Leu Ala Pro Ser Ser Lys Ser Thr Ser
           125                 130                 135

Gly Gly Thr Ala Ala Leu Gly Cys Leu Val Lys Asp Tyr Phe Pro
           140                 145                 150

Glu Pro Val Thr Val Ser Trp Asn Ser Gly Ala Leu Thr Ser Gly
           155                 160                 165

Val His Thr Phe Pro Ala Val Leu Gln Ser Ser Gly Leu Tyr Ser
           170                 175                 180

Leu Ser Ser Val Val Thr Val Pro Ser Ser Ser Leu Gly Thr Gln
           185                 190                 195

Thr Tyr Ile Cys Asn Val Asn His Lys Pro Ser Asn Thr Lys Val
           200                 205                 210

Asp Lys Lys Val Glu Pro Lys Ser Cys Asp Lys Thr His Thr Cys
           215                 220                 225

Pro Pro Cys Pro Ala Pro Glu Leu Leu Gly Gly Pro Ser Val Phe
           230                 235                 240

Leu Phe Pro Pro Lys Pro Lys Asp Thr Leu Met Ile Ser Arg Thr
           245                 250                 255

Pro Glu Val Thr Cys Val Val Val Asp Val Ser His Glu Asp Pro
           260                 265                 270

Glu Val Lys Phe Asn Trp Tyr Val Asp Gly Val Glu Val His Asn
           275                 280                 285

Ala Lys Thr Lys Pro Arg Glu Glu Gln Tyr Asn Ser Thr Tyr Arg
           290                 295                 300

Val Val Ser Val Leu Thr Val Leu His Gln Asp Trp Leu Asn Gly
           305                 310                 315

Lys Glu Tyr Lys Cys Lys Val Ser Asn Lys Ala Leu Pro Ala Pro
           320                 325                 330

Ile Glu Lys Thr Ile Ser Lys Ala Lys Gly Gln Pro Arg Glu Pro
           335                 340                 345

Gln Val Tyr Thr Leu Pro Pro Ser Arg Glu Glu Met Thr Lys Asn
           350                 355                 360

Gln Val Ser Leu Thr Cys Leu Val Lys Gly Phe Tyr Pro Ser Asp
           365                 370                 375

Ile Ala Val Glu Trp Glu Ser Asn Gly Gln Pro Glu Asn Asn Tyr
           380                 385                 390

Lys Thr Thr Pro Pro Val Leu Asp Ser Asp Gly Ser Phe Phe Leu
           395                 400                 405

Tyr Ser Lys Leu Thr Val Asp Lys Ser Arg Trp Gln Gln Gly Asn
           410                 415                 420

Val Phe Ser Cys Ser Val Met His Glu Ala Leu His Asn His Tyr
           425                 430                 435

Thr Gln Lys Ser Leu Ser Leu Ser Pro Gly Lys
           440                 445

```
<210> SEQ ID NO 27
<211> LENGTH: 214
<212> TYPE: PRT
<213> ORGANISM: Artificial sequence
<220> FEATURE:
<223> OTHER INFORMATION: sequence is synthesized
```

<400> SEQUENCE: 27

```
Asp Ile Gln Met Thr Gln Ser Pro Ser Ser Leu Ser Ala Ser Val
 1               5                  10                  15

Gly Asp Arg Val Thr Ile Thr Cys Lys Ala Ser Asp Leu Ile His
            20                  25                  30

Asn Trp Leu Ala Trp Tyr Gln Gln Lys Pro Gly Lys Ala Pro Lys
        35                  40                  45

Leu Leu Ile Tyr Gly Ala Thr Ser Leu Glu Thr Gly Val Pro Ser
    50                  55                  60

Arg Phe Ser Gly Ser Gly Ser Gly Thr Asp Phe Thr Leu Thr Ile
65                  70                  75

Ser Ser Leu Gln Pro Glu Asp Phe Ala Thr Tyr Tyr Cys Gln Gln
                80                  85                  90

Tyr Trp Thr Thr Pro Phe Thr Phe Gly Gln Gly Thr Lys Val Glu
            95                 100                 105

Ile Lys Arg Thr Val Ala Ala Pro Ser Val Phe Ile Phe Pro Pro
        110                 115                 120

Ser Asp Glu Gln Leu Lys Ser Gly Thr Ala Ser Val Val Cys Leu
    125                 130                 135

Leu Asn Asn Phe Tyr Pro Arg Glu Ala Lys Val Gln Trp Lys Val
140                 145                 150

Asp Asn Ala Leu Gln Ser Gly Asn Ser Gln Glu Ser Val Thr Glu
                155                 160                 165

Gln Asp Ser Lys Asp Ser Thr Tyr Ser Leu Ser Ser Thr Leu Thr
            170                 175                 180

Leu Ser Lys Ala Asp Tyr Glu Lys His Lys Val Tyr Ala Cys Glu
        185                 190                 195

Val Thr His Gln Gly Leu Ser Ser Pro Val Thr Lys Ser Phe Asn
    200                 205                 210

Arg Gly Glu Cys
```

<210> SEQ ID NO 28
<211> LENGTH: 451
<212> TYPE: PRT
<213> ORGANISM: Artificial sequence
<220> FEATURE:
<223> OTHER INFORMATION: sequence is synthesized

<400> SEQUENCE: 28

```
Gln Val Gln Leu Gln Gln Pro Gly Ala Glu Leu Val Lys Pro Gly
 1               5                  10                  15

Ala Ser Val Lys Met Ser Cys Lys Ala Ser Gly Tyr Thr Phe Thr
            20                  25                  30

Ser Tyr Asn Met His Trp Val Lys Gln Thr Pro Gly Arg Gly Leu
        35                  40                  45

Glu Trp Ile Gly Ala Ile Tyr Pro Gly Asn Gly Asp Thr Ser Tyr
    50                  55                  60

Asn Gln Lys Phe Lys Gly Lys Ala Thr Leu Thr Ala Asp Lys Ser
65                  70                  75

Ser Ser Thr Ala Tyr Met Gln Leu Ser Ser Leu Thr Ser Glu Asp
                80                  85                  90

Ser Ala Val Tyr Tyr Cys Ala Arg Ser Thr Tyr Tyr Gly Gly Asp
            95                 100                 105

Trp Tyr Phe Asn Val Trp Gly Ala Gly Thr Thr Val Thr Val Ser
        110                 115                 120
```

Ala Ala Ser Thr Lys Gly Pro Ser Val Phe Pro Leu Ala Pro Ser
            125                 130                 135

Ser Lys Ser Thr Ser Gly Gly Thr Ala Ala Leu Gly Cys Leu Val
            140                 145                 150

Lys Asp Tyr Phe Pro Glu Pro Val Thr Val Ser Trp Asn Ser Gly
            155                 160                 165

Ala Leu Thr Ser Gly Val His Thr Phe Pro Ala Val Leu Gln Ser
            170                 175                 180

Ser Gly Leu Tyr Ser Leu Ser Ser Val Val Thr Val Pro Ser Ser
            185                 190                 195

Ser Leu Gly Thr Gln Thr Tyr Ile Cys Asn Val Asn His Lys Pro
            200                 205                 210

Ser Asn Thr Lys Val Asp Lys Lys Ala Glu Pro Lys Ser Cys Asp
            215                 220                 225

Lys Thr His Thr Cys Pro Pro Cys Pro Ala Pro Glu Leu Leu Gly
            230                 235                 240

Gly Pro Ser Val Phe Leu Phe Pro Pro Lys Pro Lys Asp Thr Leu
            245                 250                 255

Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly
            275                 280                 285

Val Glu Val His Asn Ala Lys Thr Lys Pro Arg Glu Glu Gln Tyr
            290                 295                 300

Asn Ser Thr Tyr Arg Val Val Ser Val Leu Thr Val Leu His Gln
            305                 310                 315

Asp Trp Leu Asn Gly Lys Glu Tyr Lys Cys Lys Val Ser Asn Lys
            320                 325                 330

Ala Leu Pro Ala Pro Ile Glu Lys Thr Ile Ser Lys Ala Lys Gly
            335                 340                 345

Gln Pro Arg Glu Pro Gln Val Tyr Thr Leu Pro Pro Ser Arg Asp
            350                 355                 360

Glu Leu Thr Lys Asn Gln Val Ser Leu Thr Cys Leu Val Lys Gly
            365                 370                 375

Phe Tyr Pro Ser Asp Ile Ala Val Glu Trp Glu Ser Asn Gly Gln
            380                 385                 390

Pro Glu Asn Asn Tyr Lys Thr Thr Pro Pro Val Leu Asp Ser Asp
            395                 400                 405

Gly Ser Phe Phe Leu Tyr Ser Lys Leu Thr Val Asp Lys Ser Arg
            410                 415                 420

Trp Gln Gln Gly Asn Val Phe Ser Cys Ser Val Met His Glu Ala
            425                 430                 435

Leu His Asn His Tyr Thr Gln Lys Ser Leu Ser Leu Ser Pro Gly
            440                 445                 450

Lys

<210> SEQ ID NO 29
<211> LENGTH: 213
<212> TYPE: PRT
<213> ORGANISM: Artificial sequence
<220> FEATURE:
<223> OTHER INFORMATION: sequence is synthesized

<400> SEQUENCE: 29

Gln Ile Val Leu Ser Gln Ser Pro Ala Ile Leu Ser Ala Ser Pro

-continued

```
  1               5                   10                  15
Gly Glu Lys Val Thr Met Thr Cys Arg Ala Ser Ser Ser Val Ser
                20                  25                  30

Tyr Ile His Trp Phe Gln Gln Lys Pro Gly Ser Ser Pro Lys Pro
                35                  40                  45

Trp Ile Tyr Ala Thr Ser Asn Leu Ala Ser Gly Val Pro Val Arg
                50                  55                  60

Phe Ser Gly Ser Gly Ser Gly Thr Ser Tyr Ser Leu Thr Ile Ser
                65                  70                  75

Arg Val Glu Ala Glu Asp Ala Ala Thr Tyr Tyr Cys Gln Gln Trp
                80                  85                  90

Thr Ser Asn Pro Pro Thr Phe Gly Gly Gly Thr Lys Leu Glu Ile
                95                  100                 105

Lys Arg Thr Val Ala Ala Pro Ser Val Phe Ile Phe Pro Pro Ser
                110                 115                 120

Asp Glu Gln Leu Lys Ser Gly Thr Ala Ser Val Val Cys Leu Leu
                125                 130                 135

Asn Asn Phe Tyr Pro Arg Glu Ala Lys Val Gln Trp Lys Val Asp
                140                 145                 150

Asn Ala Leu Gln Ser Gly Asn Ser Gln Glu Ser Val Thr Glu Gln
                155                 160                 165

Asp Ser Lys Asp Ser Thr Tyr Ser Leu Ser Ser Thr Leu Thr Leu
                170                 175                 180

Ser Lys Ala Asp Tyr Glu Lys His Lys Val Tyr Ala Cys Glu Val
                185                 190                 195

Thr His Gln Gly Leu Ser Ser Pro Val Thr Lys Ser Phe Asn Arg
                200                 205                 210

Gly Glu Cys
```